(12) United States Patent
Bogash et al.

(10) Patent No.: US 8,019,471 B2
(45) Date of Patent: Sep. 13, 2011

(54) INTEGRATED, NON-SEQUENTIAL, REMOTE MEDICATION MANAGEMENT AND COMPLIANCE SYSTEM

(75) Inventors: Robert C. Bogash, Indiana Head Park, IL (US); Christopher E. Bossi, Altoona, PA (US); Christopher J. Vereb, Erie, PA (US); Harvey E. Downey, Fairview, PA (US); Gerald R. Grafius, Erie, PA (US); C. David Rogers, Erie, PA (US); Dennis Coon, Erie, PA (US); Mary Anne Papp, New Berlin, WI (US)

(73) Assignee: InRange Systems, Inc., Altoona, PA (US)

( * ) Notice: Subject to any disclaimer, the term of this patent is extended or adjusted under 35 U.S.C. 154(b) by 0 days.

(21) Appl. No.: 11/013,285

(22) Filed: Dec. 15, 2004

(65) Prior Publication Data
US 2005/0240305 A1  Oct. 27, 2005

Related U.S. Application Data

(60) Provisional application No. 60/565,221, filed on Apr. 24, 2004.

(51) Int. Cl.
*G06F 17/00* (2006.01)
(52) U.S. Cl. ........ 700/242; 700/232; 700/244; 700/243; 700/236
(58) Field of Classification Search .......... 221/1–312 C; 700/231–244
See application file for complete search history.

(56) References Cited

U.S. PATENT DOCUMENTS

| | | | |
|---|---|---|---|
| 2,771,214 | A | 9/1953 | LeFebvre |
| 3,143,207 | A | 8/1964 | Wagner |
| 3,673,885 | A | 8/1964 | Guglielmo |
| 3,329,080 | A | 7/1967 | Reach |
| 3,351,192 | A | 11/1967 | LaPlalnte |
| 3,390,766 | A | 7/1968 | Stockdale |
| 3,393,795 | A | 7/1968 | Covert, Jr. |
| 3,410,450 | A | 11/1968 | Fortenberry |
| 3,450,306 | A | 6/1969 | Gill |
| 3,482,733 | A | 12/1969 | Groves |
| 3,503,493 | A | 3/1970 | Nagy |
| 3,563,405 | A | 2/1971 | Zaremski |

(Continued)

FOREIGN PATENT DOCUMENTS
EP  0129785  6/1984
(Continued)

OTHER PUBLICATIONS

ADDS inc.: VA and DOD Clinic Dispensing System Software (1998).

(Continued)

*Primary Examiner* — Michael Collins
(74) *Attorney, Agent, or Firm* — Vedder Price PC

(57) ABSTRACT

An integrated medication management and compliance system for enabling a care provider to remotely manage and deliver individual doses of therapeutic products to a patient, in a non-sequential fashion. The system includes delivery apparatus remotely located from the care provider, wherein the apparatus stores a plurality of sealed unit dose packages that are delivered to a patient at a scheduled dosing time. The delivery apparatus is coupled to a control facility and to a computer terminal of the care provider by way of a secure communications network. The system enables the patient's medication regimen to be remotely tailored in real-time to accommodate fluid medical conditions.

19 Claims, 34 Drawing Sheets

U.S. PATENT DOCUMENTS

| | | | |
|---|---|---|---|
| 3,654,890 A | 4/1972 | Rigney et al. | |
| 3,773,250 A | 11/1973 | Phillips | |
| 3,831,006 A | 8/1974 | Chaffin, III et al. | |
| 3,848,112 A | 11/1974 | Weichselbaum et al. | |
| 3,876,268 A | 4/1975 | Colver | |
| 3,921,196 A | 11/1975 | Patterson | |
| 4,019,793 A | 4/1977 | Gerding | |
| 4,148,273 A | 4/1979 | Hollingsworth et al. | |
| 4,164,320 A | 8/1979 | Irazoqui et al. | |
| 4,165,709 A | 8/1979 | Studer | |
| 4,176,762 A | 12/1979 | Scalera | |
| 4,223,801 A | 9/1980 | Carlson | |
| 4,415,802 A | 11/1983 | Long | |
| 4,462,696 A | 7/1984 | Yung et al. | |
| 4,476,381 A | 10/1984 | Rubin | |
| 4,504,153 A | 3/1985 | Schollmeyer | |
| 4,572,403 A | 2/1986 | Benaroya | |
| 4,573,580 A | 3/1986 | Messer | |
| 4,616,316 A | 10/1986 | Hanpeter et al. | |
| 4,628,193 A | 12/1986 | Blum | |
| 4,655,026 A | 4/1987 | Wigoda | |
| 4,660,991 A | 4/1987 | Simon | |
| 4,704,517 A | 11/1987 | Campisi et al. | |
| 4,725,997 A | 2/1988 | Urquhart et al. | |
| 4,733,362 A | 3/1988 | Haraguchi | |
| 4,733,797 A | 3/1988 | Haber | |
| 4,748,600 A | 5/1988 | Urquhart | |
| 4,763,810 A | 8/1988 | Christiansen | |
| 4,768,177 A | 8/1988 | Kehr et al. | |
| 4,785,969 A | 11/1988 | McLaughlin | |
| 4,790,118 A | 12/1988 | Chilcoate | |
| 4,818,850 A | 4/1989 | Gombrich et al. | |
| 4,823,982 A | 4/1989 | Aten et al. | |
| 4,835,372 A | 5/1989 | Gombrich et al. | |
| 4,847,764 A | 7/1989 | Halvorson | |
| 4,853,521 A | 8/1989 | Claeys et al. | |
| 4,857,716 A | 8/1989 | Gambrich et al. | |
| 4,869,392 A | 9/1989 | Moulding, Jr. et al. | |
| 4,872,591 A | 10/1989 | Konopka | |
| 4,911,327 A | 3/1990 | Shepherd et al. | |
| 4,933,873 A | 6/1990 | Kaufman et al. | |
| 4,953,745 A | 9/1990 | Rowlett, Jr. | |
| 4,970,669 A | 11/1990 | McIntosh et al. | |
| 4,978,335 A | 12/1990 | Arthur | |
| 4,998,623 A | 3/1991 | Doull | |
| 5,006,699 A | 4/1991 | Felkner et al. | |
| 5,014,851 A | 5/1991 | Wick | |
| 5,014,875 A | 5/1991 | McLaughlin et al. | |
| 5,016,172 A | 5/1991 | Dessertine | |
| 5,020,037 A | 5/1991 | Raven | |
| 5,036,462 A | 7/1991 | Kaufman et al. | |
| 5,047,948 A | 9/1991 | Turner | |
| 5,065,655 A | 11/1991 | Haber | |
| 5,071,168 A | 12/1991 | Shamos | |
| 5,072,430 A * | 12/1991 | Eckernas et al. | 368/10 |
| 5,082,113 A | 1/1992 | Romick | |
| 5,084,828 A | 1/1992 | Kaufman et al. | |
| 5,102,008 A | 4/1992 | Kaufman et al. | |
| 5,109,984 A | 5/1992 | Romick | |
| 5,110,007 A | 5/1992 | Law et al. | |
| 5,119,969 A * | 6/1992 | Haber | 221/71 |
| 5,126,957 A | 6/1992 | Kaufman et al. | |
| 5,142,484 A | 8/1992 | Kaufman et al. | |
| 5,148,944 A | 9/1992 | Kaufman et al. | |
| 5,159,581 A | 10/1992 | Agans | |
| 5,163,559 A | 11/1992 | Bunin | |
| 5,176,285 A | 1/1993 | Shaw | |
| 5,180,518 A | 1/1993 | Sugihara et al. | |
| 5,181,189 A | 1/1993 | Hafner | |
| 5,197,632 A | 3/1993 | Kaufman et al. | |
| 5,230,441 A | 7/1993 | Kaufman et al. | |
| 5,244,091 A | 9/1993 | Tannenbaum | |
| 5,251,757 A | 10/1993 | Relyea et al. | |
| 5,263,596 A * | 11/1993 | Williams | 221/153 |
| 5,267,174 A | 11/1993 | Kaufman et al. | |
| 5,291,191 A | 3/1994 | Moore | |
| 5,299,122 A | 3/1994 | Wang et al. | |
| 5,314,243 A | 5/1994 | McDonald | |
| 5,323,920 A | 6/1994 | Harris et al. | |
| 5,329,459 A | 7/1994 | Kaufman et al. | |
| 5,335,816 A | 8/1994 | Kaufman et al. | |
| 5,337,919 A | 8/1994 | Spaulding et al. | |
| 5,347,453 A | 9/1994 | Maestre | |
| 5,368,187 A | 11/1994 | Poncetta et al. | |
| 5,377,839 A | 1/1995 | Relyea et al. | |
| 5,390,238 A | 2/1995 | Kirk et al. | |
| 5,392,952 A | 2/1995 | Bowden | |
| 5,405,011 A | 4/1995 | Haber et al. | |
| 5,408,443 A | 4/1995 | Weinberger | |
| 5,412,372 A | 5/1995 | Parkhurst et al. | |
| 5,429,761 A | 7/1995 | Havelka et al. | |
| 5,431,299 A | 7/1995 | Brewer et al. | |
| 5,439,648 A | 8/1995 | Balderson et al. | |
| 5,441,165 A | 8/1995 | Kemp et al. | |
| 5,442,728 A | 8/1995 | Kaufman et al. | |
| 5,454,900 A | 10/1995 | Han et al. | |
| 5,460,294 A * | 10/1995 | Williams | 221/2 |
| 5,468,110 A | 11/1995 | McDonald et al. | |
| 5,472,113 A | 12/1995 | Shaw | |
| 5,489,025 A | 2/1996 | Romick | |
| 5,508,499 A | 4/1996 | Ferrario | |
| 5,508,912 A | 4/1996 | Schneiderman | |
| 5,511,594 A | 4/1996 | Brennan et al. | |
| 5,529,188 A | 6/1996 | Coggswell | |
| 5,542,236 A | 8/1996 | Miller | |
| 4,614,366 A | 9/1996 | North et al. | |
| 5,564,593 A | 10/1996 | East, Sr. | |
| 5,566,829 A | 10/1996 | Cotilletta | |
| 5,570,810 A | 11/1996 | Lambelet, Jr. et al. | |
| 5,582,323 A | 12/1996 | Kurtenbach | |
| 5,582,593 A | 12/1996 | Hultman | |
| 5,583,831 A | 12/1996 | Churchill et al. | |
| 5,593,390 A | 1/1997 | Castellano et al. | |
| 5,597,495 A | 1/1997 | Keil et al. | |
| 5,597,995 A | 1/1997 | Williams et al. | |
| 5,609,258 A | 3/1997 | Shaw | |
| 5,623,242 A | 4/1997 | Dawson, Jr. et al. | |
| 5,630,347 A * | 5/1997 | Elvio | 83/210 |
| 5,642,731 A | 7/1997 | Kehr | |
| 5,646,912 A | 7/1997 | Cousin | |
| 5,651,775 A | 7/1997 | Walker et al. | |
| 5,657,236 A | 8/1997 | Conkright | |
| 5,703,786 A | 12/1997 | Conkright | |
| 5,710,551 A | 1/1998 | Ridgeway | |
| 5,713,856 A | 2/1998 | Eggers et al. | |
| 5,737,539 A | 4/1998 | Edelson et al. | |
| 5,752,235 A | 5/1998 | Kehr et al. | |
| 5,752,621 A | 5/1998 | Passamante | |
| 5,755,357 A | 5/1998 | Orkin et al. | |
| 5,771,657 A | 6/1998 | Lasher et al. | |
| 5,775,505 A | 7/1998 | Vasquez et al. | |
| 5,781,442 A | 7/1998 | Engleson et al. | |
| 5,791,478 A | 8/1998 | Kalvelage et al. | |
| 5,797,515 A | 8/1998 | Liff | |
| 4,695,954 A | 9/1998 | Rose et al. | |
| 5,833,071 A | 11/1998 | Ray | |
| 5,836,474 A | 11/1998 | Wessberg | |
| 5,850,344 A * | 12/1998 | Conkright | 700/231 |
| 5,852,408 A | 12/1998 | Christiansen et al. | |
| 5,852,590 A | 12/1998 | De la Huerga | |
| 5,860,419 A | 1/1999 | Davies et al. | |
| 5,868,135 A | 2/1999 | Kaufman et al. | |
| 5,878,885 A | 3/1999 | Wangu et al. | |
| 5,878,887 A | 3/1999 | Parker et al. | |
| 5,885,245 A | 3/1999 | Lynch et al. | |
| 5,898,586 A | 4/1999 | Jeatran et al. | |
| 5,904,249 A | 5/1999 | Roulin et al. | |
| 5,909,822 A | 6/1999 | George et al. | |
| 5,913,197 A | 6/1999 | Kameda | |
| 5,927,500 A | 7/1999 | Godfrey et al. | |
| 5,945,651 A * | 8/1999 | Chorosinski et al. | 235/375 |
| 5,954,641 A | 9/1999 | Kehr et al. | |
| 5,963,136 A | 10/1999 | O'Brien | |
| 5,971,594 A * | 10/1999 | Sahai et al. | 700/242 |
| 5,990,782 A | 11/1999 | Lee | |
| 6,000,828 A | 12/1999 | Leet | |
| 6,003,722 A | 12/1999 | Thurner | |

| | | | |
|---|---|---|---|
| 6,004,020 A | 12/1999 | Bartur | |
| 6,006,946 A | 12/1999 | Williams et al. | |
| 6,011,999 A * | 1/2000 | Holmes | 700/231 |
| 6,018,289 A | 1/2000 | Sekura et al. | |
| 6,021,392 A | 2/2000 | Lester et al. | |
| 6,021,918 A | 2/2000 | Dumont | |
| 6,024,699 A | 2/2000 | Surwit et al. | |
| 6,032,155 A * | 2/2000 | de la Huerga | 707/104.1 |
| 6,036,016 A | 3/2000 | Arnold | |
| 6,036,018 A | 3/2000 | Harrold | |
| 6,062,420 A | 5/2000 | Krouwel et al. | |
| 6,068,156 A | 5/2000 | Liff et al. | |
| 6,082,544 A * | 7/2000 | Romick | 206/531 |
| 6,085,752 A | 7/2000 | Kehr et al. | |
| 6,102,855 A | 8/2000 | Kehr et al. | |
| 6,112,502 A * | 9/2000 | Frederick et al. | 53/411 |
| 6,116,461 A * | 9/2000 | Broadfield et al. | 221/98 |
| 6,138,865 A | 10/2000 | Gilmore | |
| 6,150,942 A | 11/2000 | O'Brien | |
| 6,152,364 A | 11/2000 | Schoonen et al. | |
| 6,155,454 A | 12/2000 | George et al. | |
| 6,155,485 A | 12/2000 | Coughlin et al. | |
| 6,161,095 A | 12/2000 | Brown | |
| 6,161,699 A | 12/2000 | Gartland | |
| 6,168,563 B1 | 1/2001 | Brown | |
| 6,175,779 B1 * | 1/2001 | Barrett | 700/242 |
| 6,193,103 B1 | 2/2001 | Clarijs | |
| 6,198,383 B1 | 3/2001 | Sekura et al. | |
| 6,202,642 B1 | 3/2001 | McKinnon et al. | |
| 6,206,233 B1 | 3/2001 | Schulze | |
| 6,219,587 B1 | 4/2001 | Ahlin et al. | |
| 6,234,343 B1 | 5/2001 | Papp | |
| 6,263,259 B1 | 7/2001 | Bartur | |
| 6,270,455 B1 | 8/2001 | Brown | |
| 6,273,260 B1 | 8/2001 | ColDepietro et al. | |
| 6,294,999 B1 | 9/2001 | Yarin et al. | |
| 6,304,797 B1 | 10/2001 | Shusterman | |
| 6,314,384 B1 | 11/2001 | Goetz | |
| 6,330,957 B1 | 12/2001 | Bell-Greenstreet | |
| 6,332,100 B1 | 12/2001 | Sahai et al. | |
| 6,338,007 B1 | 1/2002 | Broadfield et al. | |
| 6,338,408 B1 | 1/2002 | Anderson | |
| 6,357,593 B1 | 3/2002 | Bolnick et al. | |
| 6,370,841 B1 * | 4/2002 | Chudy et al. | 53/411 |
| 6,373,787 B1 | 4/2002 | Breimesser et al. | |
| 6,375,225 B1 | 4/2002 | Lapsker | |
| 6,375,956 B1 | 4/2002 | Hermelin et al. | |
| 6,382,420 B1 | 5/2002 | Bouthiette | |
| 6,401,991 B1 | 6/2002 | Eannone | |
| 6,411,567 B1 | 6/2002 | Niemiec et al. | |
| 6,415,202 B1 | 7/2002 | Halfacre | |
| 6,415,916 B1 | 7/2002 | Rini | |
| 6,421,584 B1 | 7/2002 | Norberg et al. | |
| 6,439,422 B1 | 8/2002 | Papp et al. | |
| 6,464,142 B1 | 10/2002 | Denenberg et al. | |
| 6,471,087 B1 | 10/2002 | Shusterman | |
| 6,471,089 B2 | 10/2002 | Liff et al. | |
| 6,507,275 B2 | 1/2003 | Romano et al. | |
| 6,522,945 B2 | 2/2003 | Sleep et al. | |
| 6,527,138 B2 | 3/2003 | Pawlo et al. | |
| 6,529,446 B1 | 3/2003 | de la Huerga | |
| 6,529,801 B1 | 3/2003 | Rosenblum | |
| 6,532,399 B2 * | 3/2003 | Mase | 700/237 |
| 6,539,281 B2 * | 3/2003 | Wan et al. | 700/236 |
| 6,540,081 B2 | 4/2003 | Balz et al. | |
| 6,564,121 B1 * | 5/2003 | Wallace et al. | 700/231 |
| 6,574,166 B2 | 6/2003 | Niemiec | |
| 6,578,734 B1 | 6/2003 | Coughlin | |
| RE38,189 E | 7/2003 | Walker et al. | |
| 6,588,670 B2 | 7/2003 | Bukowski | |
| 6,589,787 B2 | 7/2003 | Dietrich et al. | |
| 6,594,549 B2 | 7/2003 | Siegel | |
| 6,601,729 B1 | 8/2003 | Papp | |
| 6,615,107 B2 | 9/2003 | Hubicki | |
| 6,625,518 B2 | 9/2003 | Depeursinge | |
| 6,636,780 B1 | 10/2003 | Haitin et al. | |
| 6,640,212 B1 | 10/2003 | Rosse | |
| 6,650,964 B2 | 11/2003 | Spano, Jr. et al. | |
| 6,655,545 B1 * | 12/2003 | Sonneborn | 221/7 |
| 6,681,935 B1 | 1/2004 | Lewis | |
| 6,689,091 B2 | 2/2004 | Bui et al. | |
| 6,697,704 B2 | 2/2004 | Rosenblum | |
| 6,697,783 B1 | 2/2004 | Brinkman et al. | |
| 6,702,146 B2 * | 3/2004 | Varis | 221/3 |
| 6,732,884 B2 | 5/2004 | Topliffe et al. | |
| 6,735,497 B2 * | 5/2004 | Wallace et al. | 700/231 |
| 6,735,551 B2 | 5/2004 | Voegeli et al. | |
| 6,766,218 B2 | 7/2004 | Rosenblum | |
| 6,766,219 B1 * | 7/2004 | Hasey | 700/242 |
| 6,783,492 B2 | 8/2004 | Dominguez et al. | |
| 6,785,589 B2 | 8/2004 | Eggenberger et al. | |
| 6,799,149 B2 | 9/2004 | Hartlaub | |
| 6,802,422 B2 | 10/2004 | Kalvelage et al. | |
| 6,822,554 B2 | 11/2004 | Vrijens et al. | |
| 6,832,200 B2 | 12/2004 | Greeven et al. | |
| 6,839,304 B2 | 1/2005 | Niemiec et al. | |
| 6,842,736 B1 | 1/2005 | Brzozowski | |
| 6,484,593 B2 | 2/2005 | Papp | |
| 6,848,593 B2 | 2/2005 | Papp | |
| 6,854,618 B2 | 2/2005 | Harrold | |
| 6,871,783 B2 | 3/2005 | Kaafarani et al. | |
| 6,892,512 B2 | 5/2005 | Rice et al. | |
| 6,892,941 B2 | 5/2005 | Rosenblum | |
| 6,909,359 B1 | 6/2005 | McGovern | |
| 6,910,601 B2 * | 6/2005 | Thomas et al. | 221/119 |
| 6,913,149 B2 | 7/2005 | Gelardi et al. | |
| 6,928,338 B1 | 8/2005 | Buchser et al. | |
| 6,935,560 B2 | 8/2005 | Andreasson et al. | |
| 6,951,282 B2 | 10/2005 | Jones | |
| 6,951,353 B2 | 10/2005 | Kozlowski et al. | |
| 6,973,371 B1 | 12/2005 | Benouali | |
| 6,978,286 B2 | 12/2005 | Francis et al. | |
| 6,981,609 B2 * | 1/2006 | Yuyama et al. | 221/15 |
| 6,985,846 B1 | 1/2006 | Dunlavey | |
| 6,985,869 B1 | 1/2006 | Stoll et al. | |
| 6,994,249 B2 | 2/2006 | Peterka et al. | |
| 7,000,769 B2 | 2/2006 | Killinger | |
| 7,002,476 B2 | 2/2006 | Rapchak | |
| 7,006,893 B2 * | 2/2006 | Hart et al. | 700/235 |
| 7,010,431 B2 | 3/2006 | Boucher | |
| 7,040,504 B2 | 5/2006 | Broadfield et al. | |
| 7,044,302 B2 | 5/2006 | Conley | |
| 7,048,141 B2 | 5/2006 | Abdulhay et al. | |
| 7,055,294 B1 | 6/2006 | Lewis | |
| 7,069,226 B1 | 6/2006 | Kleinfelter | |
| 7,080,755 B2 | 7/2006 | Handfield et al. | |
| 7,093,716 B2 | 8/2006 | Intini | |
| 7,107,122 B1 | 9/2006 | Whyte | |
| 7,111,780 B2 | 9/2006 | Broussard et al. | |
| 7,113,101 B2 | 9/2006 | Petersen et al. | |
| 7,122,005 B2 | 10/2006 | Shusterman | |
| 7,123,989 B2 | 10/2006 | Pinney et al. | |
| 7,126,879 B2 | 10/2006 | Snyder | |
| 7,162,437 B2 | 1/2007 | Shaak et al. | |
| 7,165,077 B2 | 1/2007 | Kalies | |
| 7,171,371 B2 | 1/2007 | Goldstein | |
| 7,178,688 B2 * | 2/2007 | Naufel et al. | 221/28 |
| 7,188,082 B2 | 3/2007 | Keane et al. | |
| 7,210,598 B2 | 5/2007 | Gerold et | |
| 7,213,721 B2 | 5/2007 | Abdulhay et al. | |
| 7,223,235 B2 | 5/2007 | Brown | |
| 7,228,198 B2 | 6/2007 | Vollm et al. | |
| 7,260,402 B1 | 8/2007 | Ahmed | |
| 7,263,411 B2 | 8/2007 | Shows et al. | |
| 7,264,136 B2 * | 9/2007 | Willoughby et al. | 221/3 |
| 7,269,476 B2 | 9/2007 | Ratnakar | |
| 7,286,996 B1 | 10/2007 | Fiedotin et al. | |
| 7,286,997 B2 | 10/2007 | Spector et al. | |
| 7,295,890 B2 | 11/2007 | Jean-Pierre | |
| 7,304,582 B2 | 12/2007 | Kerr, II et al. | |
| 7,328,802 B2 | 2/2008 | Killinger | |
| 7,330,101 B2 | 2/2008 | Sekura | |
| 7,336,564 B2 | 2/2008 | Feodoroff | |
| 7,366,675 B1 | 4/2008 | Walker et al. | |
| 7,395,214 B2 | 7/2008 | Shillingburg | |
| 7,419,056 B2 | 9/2008 | Gattefosse et al. | |
| 7,422,110 B2 | 9/2008 | Zanden et al. | |
| 7,440,817 B2 | 10/2008 | Fu | |

| | | | |
|---|---|---|---|
| 7,444,203 B2 | 10/2008 | Rosenblum | |
| 7,451,876 B2 * | 11/2008 | Bossi et al. | 206/534 |
| 7,454,880 B1 | 11/2008 | Austin et al. | |
| 7,502,666 B2 | 3/2009 | Siegel et al. | |
| 2001/0028308 A1 | 10/2001 | De La Huerga | |
| 2002/0104773 A1 | 8/2002 | Kalvelage et al. | |
| 2002/0147526 A1 | 10/2002 | Siegel | |
| 2002/0173875 A1 | 11/2002 | Wallace et al. | |
| 2003/0042167 A1 | 3/2003 | Balz et al. | |
| 2003/0057230 A1 | 3/2003 | Stevens et al. | |
| 2003/0102247 A1 | 6/2003 | Inoue et al. | |
| 2003/0209558 A1 | 11/2003 | Cross | |
| 2004/0133305 A1 | 7/2004 | Jean-Pierre | |
| 2004/0133705 A1 | 7/2004 | Broussard | |
| 2004/0149135 A1 | 8/2004 | Cai | |
| 2004/0254676 A1 | 12/2004 | Blust | |
| 2005/0049747 A1 * | 3/2005 | Willoughby et al. | 700/232 |
| 2005/0087473 A1 | 4/2005 | Fabricius et al. | |
| 2005/0145644 A1 | 7/2005 | Mori et al. | |
| 2005/0150897 A1 | 7/2005 | Fabricius et al. | |
| 2005/0216120 A1 | 9/2005 | Rosenberg | |
| 2005/0237222 A1 | 10/2005 | Bossi | |
| 2005/0240305 A1 | 10/2005 | Bogash | |
| 2005/0256830 A1 | 11/2005 | Siegel et al. | |
| 2005/0274643 A1 | 12/2005 | Arnold | |
| 2006/0058917 A1 | 3/2006 | Vonk et al. | |
| 2006/0249421 A1 | 11/2006 | Pham | |
| 2008/0119958 A1 | 5/2008 | Bear et al. | |

FOREIGN PATENT DOCUMENTS

| | | |
|---|---|---|
| EP | 0852208 | 6/1996 |
| EP | 119501 A1 | 6/1998 |
| EP | 1263579 | 11/2003 |
| EP | 1401729 | 3/2004 |
| FR | 2611671 | 9/1988 |
| GB | 2343440 | 10/2000 |
| JP | 10-201827 | 4/1998 |
| JP | 2001-101144 | 4/2001 |
| JP | 2002279068 | 9/2002 |
| JP | 2003002361 | 1/2003 |
| WO | WO 99/17218 A1 | 4/1999 |
| WO | WO 99/43283 A3 | 9/1999 |
| WO | 9960982 | 12/1999 |
| WO | WO 00/07538 | 2/2000 |
| WO | WO 00/25720 A2 | 5/2000 |
| WO | WO 01/08106 | 2/2001 |
| WO | 01/47466 AQ | 7/2001 |
| WO | WO 02/24141 A1 | 3/2002 |
| WO | 02078595 A2 | 10/2002 |
| WO | 02091987 A2 | 11/2002 |
| WO | WO 03/003970 B1 | 1/2003 |
| WO | WO 03/073977 A1 | 9/2003 |
| WO | WO 03/079959 B1 | 10/2003 |
| WO | WO 2004/002396 A1 | 1/2004 |
| WO | WO 2005/009326 A2 | 2/2005 |
| WO | WO 2005/065628 A1 | 7/2005 |
| WO | 2005/109119 A2 | 11/2005 |

OTHER PUBLICATIONS

Telepharmacy: VA Pharmacy Finds Convenience in Vending Machines, Veterans Health System Journal, Sep. 1998, pp. 74-75.
Written Opinion for PCT/US04/42187, dated Nov. 9, 2006.
Modified Abstract, Search Report and Modified Search Report to Application No. 01301108.5-2308 (European Patent Office) dated Nov. 7, 2001.
European Search Report for European Patent Application EP 0030 2342.
Annex to European Search Report for EP 00 20 2342, including Abstract.
Carrier Tape by Advantek Inc. (Mar. 2000), pp. 1-2.
Cover tapes by Advantek Inc. (Mar. 2000), pp. 1-2.
Lokreel packaging reels by Advantek Inc. (Mar. 2000), pp. 1-2.
ATR-1000 content, Advantek Inc., (Mar. 2000), p. 1.
3M production information: component handling & materials (Feb. 2000), pp. 1-4.
International Search Report for PCT/US04/42187, dated Nov. 9, 2006.
International Preliminary Report on Patentability for PCT/US04/42187, dated Aug. 20, 2007.
Communication Relating to the Results of the Partial International Search for PCT/US2008/070305 dated Dec. 3, 2008.
Examination Report for European Application Serial No. 98731955.4 issued Jan. 22, 2010.
English Translation of Japanese Office Action entitled "Notice of Reasons for Refusal" in Japanese Patent Application 2007-509452 prepared on Jan. 25, 2011.
Examiner's First Report on Patent Application No. 2004319508 by InRange Systems, Inc. issued by the Australian Patent Office on Mar. 4, 2010.
Office Action of Mar. 3, 2010 in U.S. Appl. No. 12/244,504.

* cited by examiner

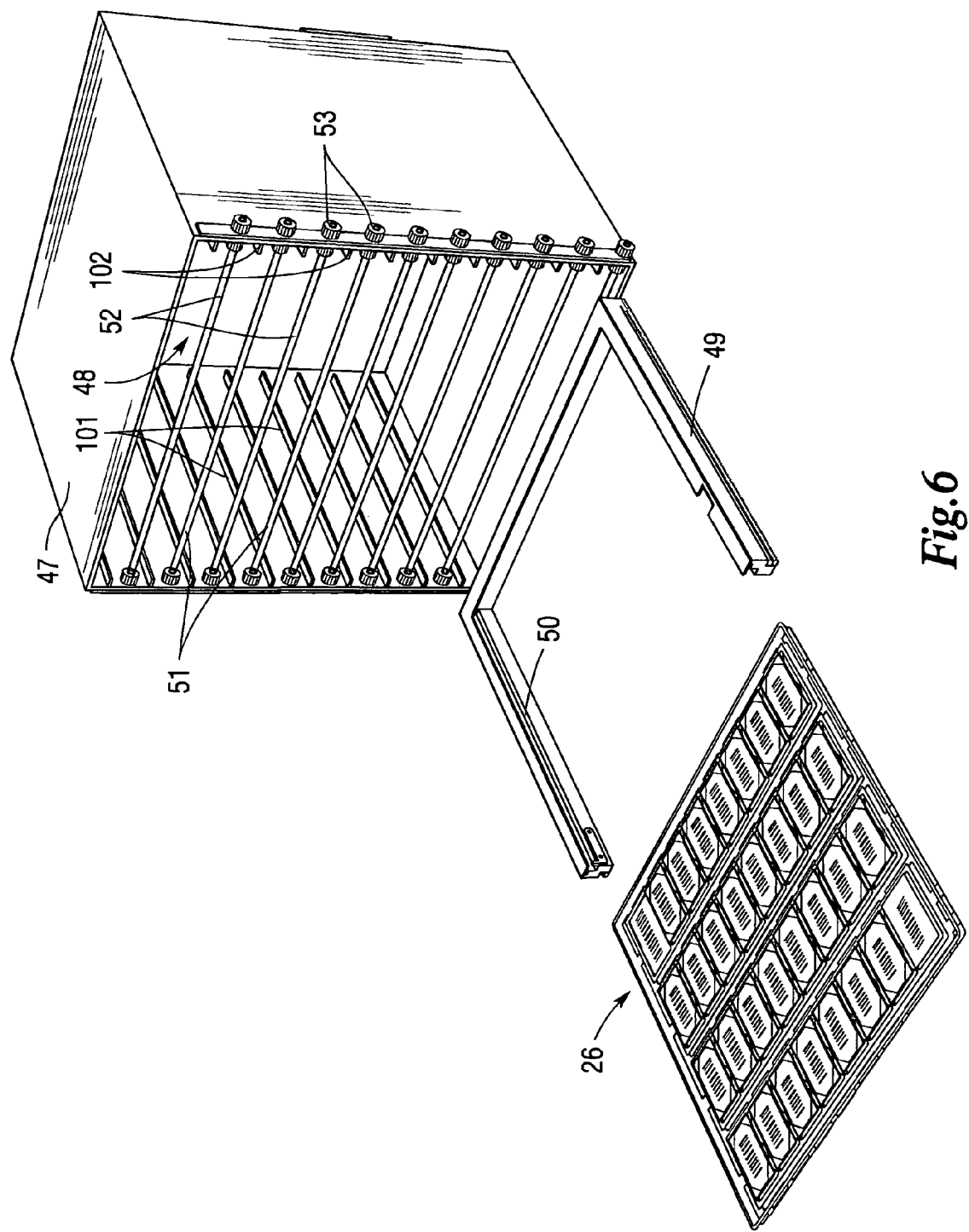

Rx Management System
File Edit Tools Help

Patient List

User rbogash
5/5/2004

Actions
- To Do List
- Patients
- Reports
- New Patients

Edit Selected | Refresh All | Search For [ Last Name ▼ ] | Search

Search By

Display for Provider: Robert Bogash ▼

| ID | Last Name | First Name | Address | City | St | Zip | Provider |
|---|---|---|---|---|---|---|---|
| 1 | Johnson | Rebecca | 1331 Mockingbird Lane | Indian Head Park | IL | 12345 | Robert Bogash |
| mya | Collins | Melinda | 77 West Lane | Chicago | IL | 88845 | Robert Bogash |
| A | Davenport | Joseph | 1308 Pinewood Dr | Sarasota | FL | 55555 | Robert Bogash |
| bb | Franklin | Todd | 428 Liles Rd | Lagrange | IL | 77777 | Robert Bogash |
| k3 | Franklin | Sandra | 428 Liles Rd | Lagrange | IL | 77777 | Robert Bogash |
| 211d | Smith | Al | 33 Concord Ave | Chicago | IL | 88825 | Robert Bogash |
| 12d | Manchester | Linda | 44 daniels Ct | Lagrange | IL | 99999 | Robert Bogash |
| 000123 | Powell | David | 4 Louis St | Chicago | IL | 88822 | Robert Bogash |
| Hk123 | Williams | Agnes | 72 daniels Ct | Afton | MO | 33333 | Robert Bogash |
| 7223 | Smith | Ray | 14 West Lindly Ave | Indian Head Park | IL | 12345 | Robert Bogash |
| 555 | Sanderson | William | 183 East Ln | Chicago | IL | 88822 | Robert Bogash |
| sssg4 | Smith | Doug | 20 1010 Hwy | Indian Head Park | IL | 12345 | Robert Bogash |
| 4ddff | Hall | Tiffany | | Chicago | IL | 88829 | Robert Bogash |

Logoff | Close

*Fig. 28*

Rebecca Johnson - Therapy Schedule

User: rbogash
5/5/2004

[Edit Selected]

| Drug Name | Mean Dosage | Start Date | Duration | Remaining Days | Days Taken |
|---|---|---|---|---|---|
| Coumadin / Warfarin | 8 | 4/26/2004 | 30 | 22 | SMTWHFS |
| Coumadin / Warfarin | 8 | 4/6/2004 | 30 | 2 | SMTWHFS |

Coumadin (Warfarin) 8 mg

| Sun | Mon | Tue | Wed | Thu | Fri | Sat |
|---|---|---|---|---|---|---|
| Apr 4 | 5 | 6 4 mg | 7 8 mg | 8 4 mg | 9 8 mg | 10 4 mg |
| 11 8 mg | 12 4 mg | 13 8 mg | 14 4 mg | 15 8 mg | 16 4 mg | 17 8 mg |
| 18 4 mg | 19 8 mg | 20 4 mg | 21 8 mg | 22 4 mg | 23 8 mg | 24 4 mg |
| 15 4 mg | 16 8 mg | 27 4 mg | 28 8 mg | 29 4 mg | 30 8 mg | May 1 4 mg |
| 2 4 mg | 3 8 mg | 4 4 mg | 5 8 mg | 6 | 7 | 8 |

Display By
○ by factor
● by strength

Medication taken at the following times:
7:00 pm

Patient Actions
- To Do List
- Save All

Therapy
- View Therapy
- New Therapy
- Print Therapy

History
- Therapy History
- Delivery History
- To Do History

Patient Information
- Basic
- Providers
- Allowed Times
- Contacts

No Picture Available

Screen 2 - Patient List - Paint

INTEGRATED, NON-SEQUENTIAL, REMOTE MEDICATION MANAGEMENT AND COMPLIANCE SYSTEM

REFERENCE TO RELATED APPLICATIONS

This application claims the benefit of U.S. Provisional Patent Application No. 60/565,221 filed Apr. 24, 2004.

FIELD OF THE INVENTION

The invention relates generally to systems for facilitating patient medication compliance, and more particularly to apparatus and methods for remotely delivering individual doses of therapeutic products to a patient in a non-sequential fashion. The invention allows dosage amounts to be remotely tailored in real-time to accommodate fluid medical conditions.

BACKGROUND OF THE INVENTION

Patient non-adherence to prescribed medication regimens is a significant problem which undermines efforts to manage chronic illnesses. Factors such as an overall increase in outpatient medical procedures have contributed to an increased level of responsibility being placed upon patients and caregivers in the administration of prescription drugs. While estimates of medication non-adherence in remote, residential settings typically range from 30-60%, depending on the disease state, elderly patients average a rate of more than 45% due in part to visual, auditory, and cognitive impairments. Drugs not taken, or taken incorrectly, incur the same health care costs as fully adherent regimens, but without the expected medical outcome. The consequences of non-adherence can be significant, resulting in emergency room visits, extended hospitalizations, long-term care facility admissions, and death.

The ability to comply with a medication regimen is complicated in situations where dosing amounts change over time. For instance, prescribed dosing amounts are frequently a function of ongoing laboratory tests that determine the patient's status. Likewise, appropriate dosage amounts are determined in accordance with a patient's health condition and must reflect unexpected changes in such condition. In these situations, healthcare practitioners such as physicians, pharmacists, and nurses need to be able to adjust a patient's dosage as quickly as possible. Medication compliance is particularly important when narrow therapeutic index drugs are prescribed, as over-medicating or under-medicating a patient can cause serious side effects, illness and even death.

A fairly large number of devices have been developed for prompting a patient to take a prescribed dose of medication at the correct times. Existing devices function primarily to remind patients when to take a particular medication and to sequentially deliver that medication in accordance with a predetermined schedule. Many of these devices are designed to expel medication automatically, in accordance with a predetermined schedule. In this regard, the devices do not provide adequate protection against both under-dosage and over-dosage. If the patient fails to take the medication according to schedule, the devices continue to expel medication at set intervals based on the premise that the patient took all previous medications appropriately. Such a situation greatly enhances the risk of non-compliance, wherein a patient takes less medication than is prescribed. Conversely, if the patient does not take the medication according to schedule, but too close to the time for taking subsequent medication, the patient faces the risk of over-dosage.

Certain devices incorporate means for retrieving pills which are discharged but not removed from the device. Some of these devices provide notification to caregivers of a patient's failure to take medication according to schedule. Other devices have been integrated into comprehensive medication management and delivery systems in which a healthcare practitioner remotely monitors information regarding patient compliance and non-compliance with a medication regimen. While these systems enhance patient compliance with a prescribed treatment regimen, they are deficient in one notable respect, that is, they do not provide a mechanism by which a patient's failure to take a scheduled dose of medication can be rectified in minutes. As such, the systems do not overcome the problem of patient under-dosage and over-dosage. This drawback is particularly significant with respect to high risk patient populations, where patients frequently suffer from cognitive, visual and/or auditory impairments which contribute to non-adherence.

An additional shortcoming of the existing systems is that they fail to provide a mechanism by which a prescribed dosage can be remotely adjusted in minutes, in response to an unexpected change in a patient's health condition. Although the systems allow a healthcare practitioner to communicate a change in dosing amount to the patient, they do not enable the practitioner to immediately and remotely change, adjust or discontinue a prescribed dosage. There is often a delay of several hours, and in some cases, several days, before a patient is able to procure the new dosage. During this period, the patient may be confused as to the correct regimen and continue to take the discontinued dosage. In addition, because a new prescription is required every time a dose is adjusted, the patient is must travel to a physician's office and/or a pharmacy. Although this may pose an inconvenience to some patients, this is particularly disadvantageous to mobility-impaired patients and is a major contributor to drug non-compliance. Frequently the patient's condition deteriorates, as the patient is unable to continue the correct course of treatment.

A further drawback of the conventional systems is that prescriptions are filled in either standard thirty day or sixty day allotments. With such means, there is no accurate way to inventory pharmaceuticals and/or to audit patient compliance or consumption of the product. This is due in part to the fact that the pharmaceuticals are dispensed in a lot, and not every pill or dose is separately bar coded and traceable.

The above-described medication management and delivery systems suffer from a still further limitation, namely, they fail to establish a secure data communication process to deploy communications to and from a remote medication delivery device based in a patient's home while protecting patient privacy. Maintaining patient privacy in the data communication process has to date been a formidable challenge. Moreover, an increasing number of regulations regarding the maintenance and storage of patient data have been enacted in response to the Health Insurance Portability Accountability Act. Accordingly, there is a need and a desire for a cost-effective system that quickly addresses a patient's non-compliance with a prescribed drug regimen in real time and minimizes disruptions to a patient's course of treatment while protecting patient information.

SUMMARY OF THE INVENTION

The present invention comprises a medication management and compliance system for enabling a healthcare practitioner to remotely manage and deliver sealed unit dose packages of prescription and non-prescription therapeutic products to a patient, on a dose by dose basis, and in a manner that provides immediate confirmation that a dose has been delivered. Clinical software is used for storing patient prescription and dosing regimen information, enabling authorized healthcare personnel to remotely deliver a unit dose therapy to a patient and monitor patient compliance with a dosing regimen, without violating patient privacy. The system includes delivery apparatus located in proximity to the patient, wherein the delivery apparatus is remotely coupled to the clinical software and to a control center by means of a data communications network.

The delivery apparatus features a controller for executing command signals received from the control center and clinical software, as well as a storage area for storing unit dose packages. The apparatus delivers a sealed, unit dose package to the patient at a scheduled dosing time, in response to a command signal. The present system enables the healthcare practitioner to remotely deliver any unit dose package stored within the delivery apparatus to a patient, in non-consecutive fashion, without being limited by a predetermined sequence. In this way, medication dosage amounts can be instantaneously tailored to adapt to fluid medical conditions. The present invention provides a fully integrated, real-time, non-sequential, comprehensive medication management and compliance system that is the first to ensure accurate delivery of both custom packaged and commercially available sealed unit dose and unit-of-issue therapeutic products to patients.

BRIEF DESCRIPTION OF THE DRAWINGS

FIG. 6 is a perspective view depicting the storage apparatus in accordance with the present invention.

Figure 30:
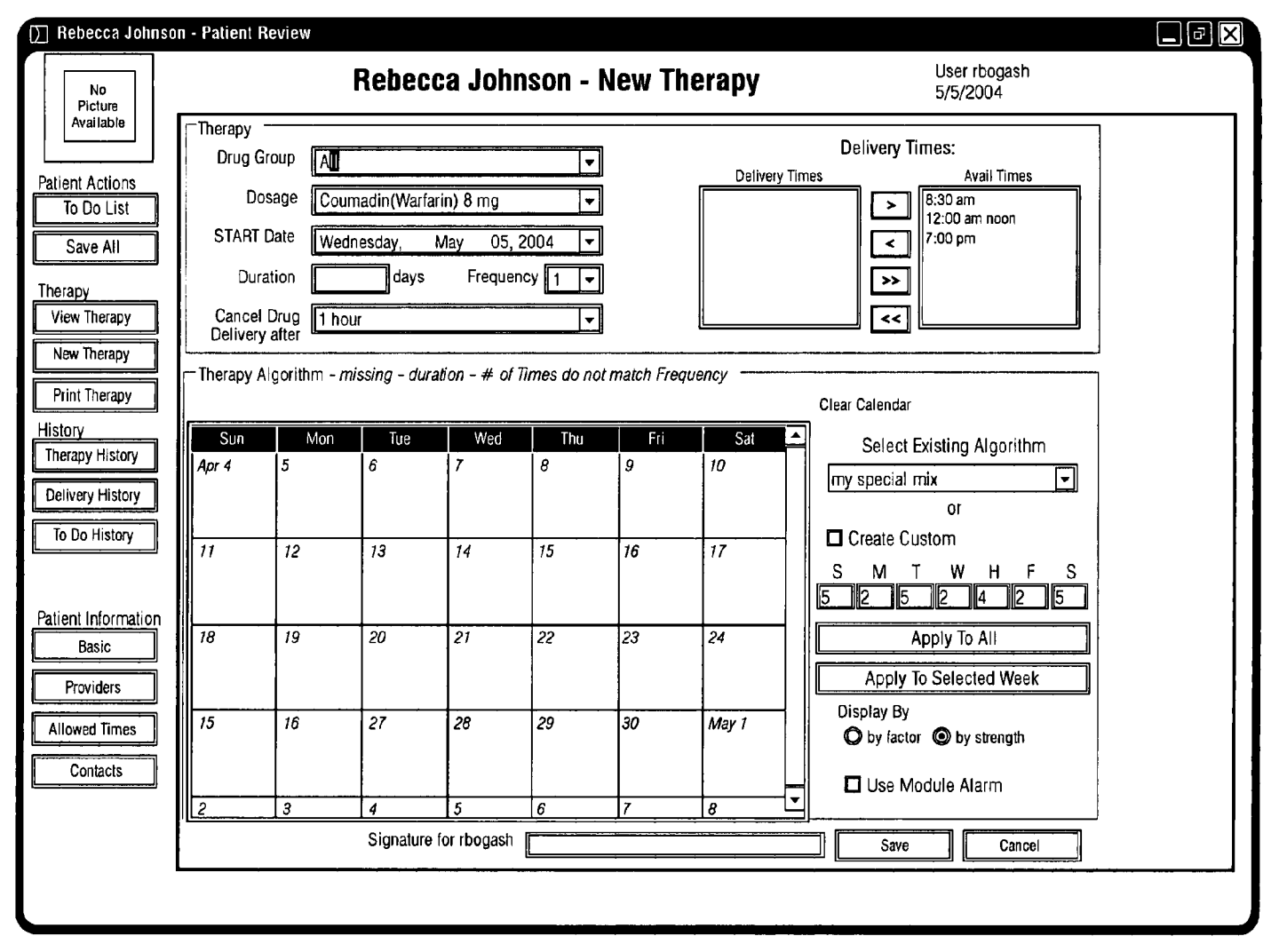
Figure 31:
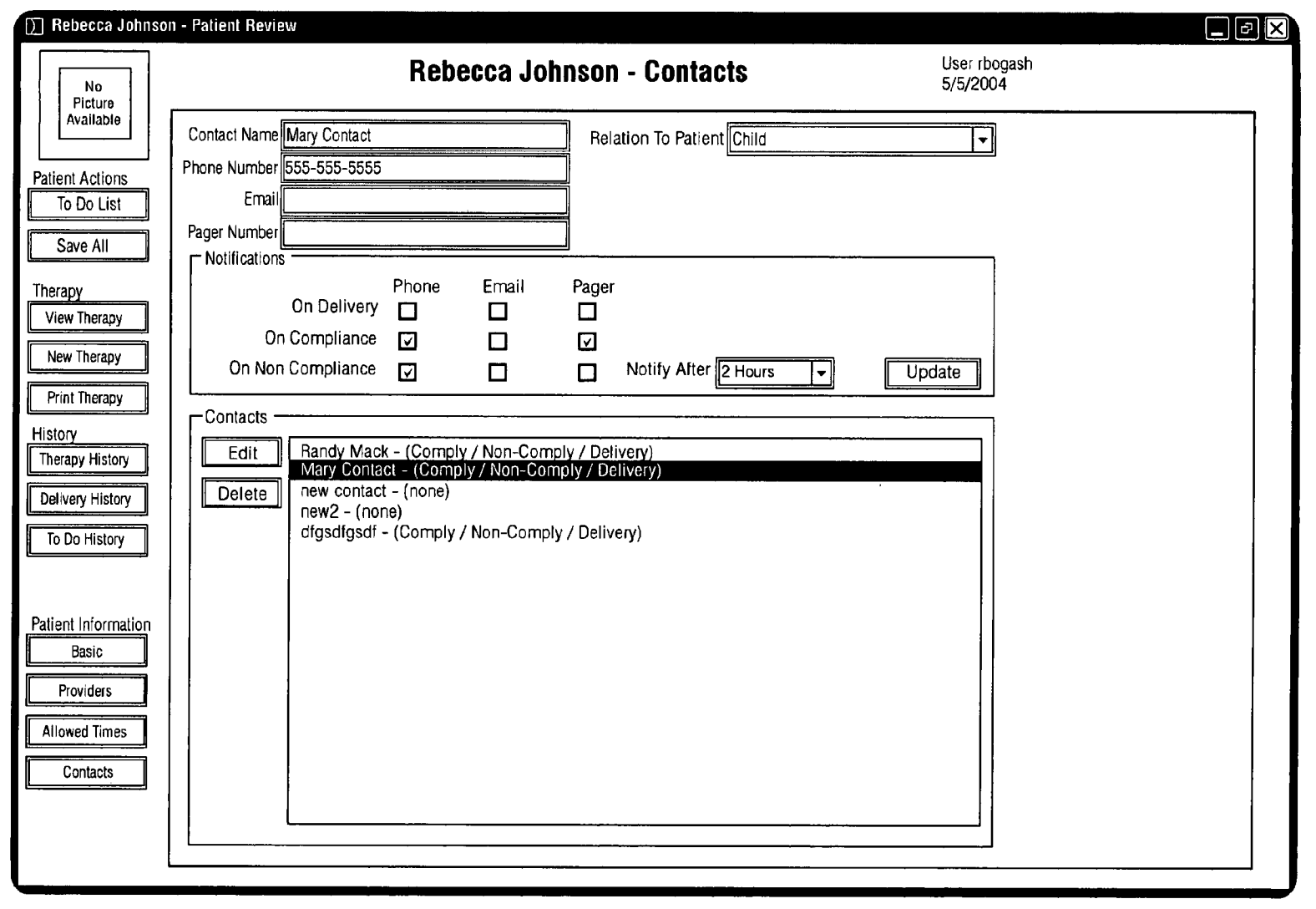

FIGS. 27-31 are examples of worksheets that appear on the computer monitor of healthcare personnel.

DETAILED DESCRIPTION OF THE INVENTION

The present invention provides a fully integrated, real-time, non-sequential medication management and compliance system for prompting a patient remote from a clinical environment to take medication in accordance with a prescribed schedule. A principal advantage of the delivery module of the present invention is that it implements a prescribed medication regimen by delivering a selected unit dose package of medication to a patient upon receipt of an encrypted command signal and patient confirmation. These multiple safeguards ensure that the patient receives the prescribed medication at the correct dosing times. In this manner, the invention enhances patient compliance and allows for chronotherapeutic applications that maximize medication benefits and minimize medication side effects. Also significant is the fact that command signals are securely transmitted to and from the delivery module without compromising patient privacy in any way.

A further advantage of the present invention is that it enables a healthcare practitioner to remotely monitor patient compliance with a prescribed medication regimen and receive rapid notification of non-compliance. Most notably, the healthcare practitioner can promptly adjust the patient's treatment plan to accommodate a missed dosage or to reflect other fluid medical conditions, such as an unexpected change in the health status of the patient. Where necessary, dosage adjustments can be made immediately, without the need for a new prescription. As such, the invention minimizes any loss of time which may complicate non-compliance and reduces medication waste by eliminating the need for a patient to discard remaining doses in the event of a dose adjustment.

A still further advantage of the invention is that it protects the patient from adverse drug reactions and related consequences of over- and under-medicating by ensuring that the patient remains within recommended therapeutic levels. The patient receives a required dosage at the proper time, thereby reducing the incidence of emergency room visits and hospital admissions occasioned by non-adherence to a prescribed drug regimen or other delays in the administration of prescribed medication. In addition, unanticipated visits to health care providers are reduced, thereby reducing overall health care costs. This cost-effective system can be used by healthcare practitioners operating in a variety of settings.

Figure 2:
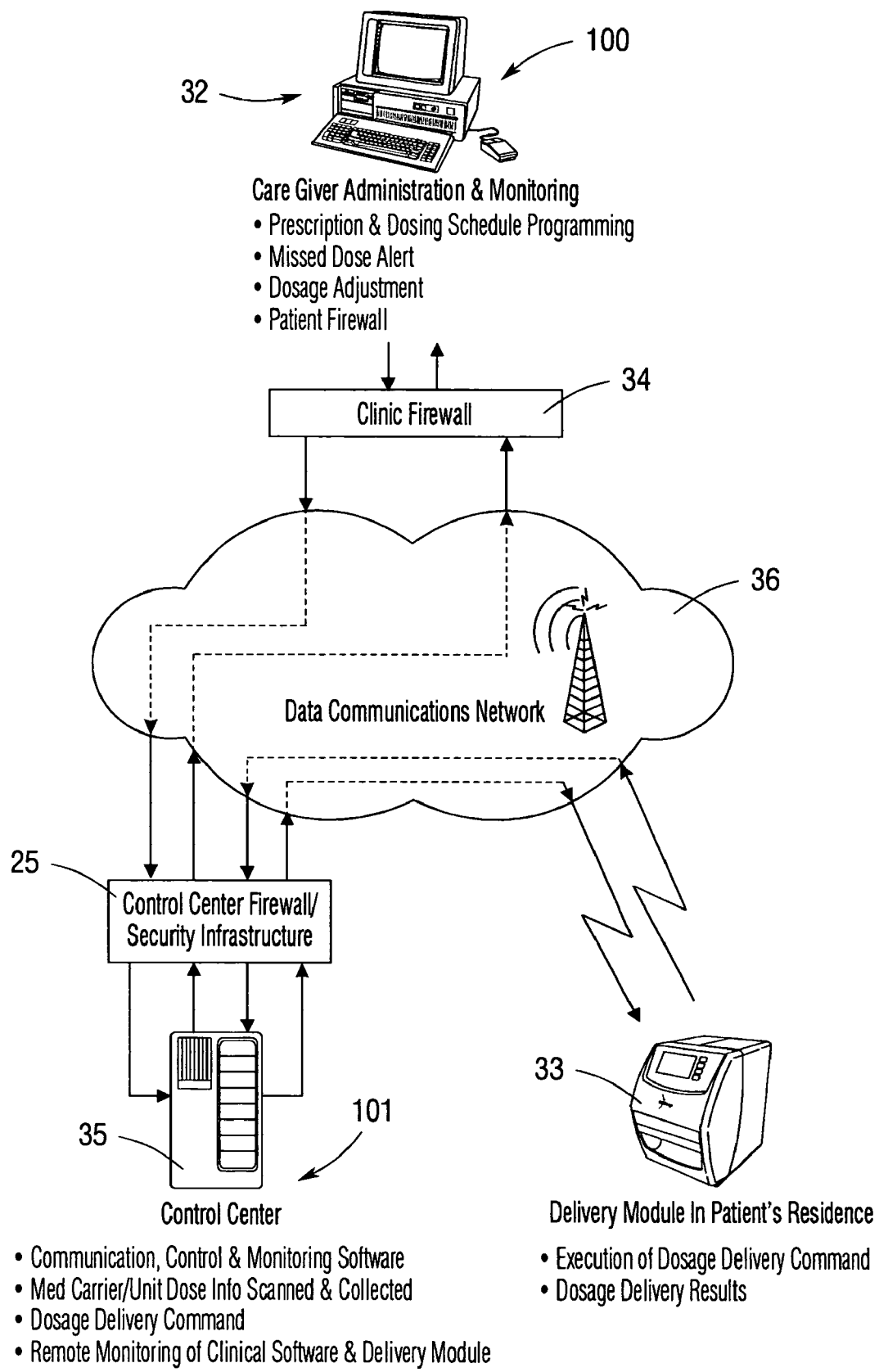
FIG. 2 is a block diagram showing a non-sequential medication delivery module with remote monitoring and access control in accordance with an embodiment of the invention.

Referring now to the Figures, there is shown in FIG. 2 an overview of the system of the present invention. A control center 101, such as a facility operated by INRange Systems, Inc., stocks custom packaged and prepackaged, unit dose prescription and non-prescription medical products, pharmaceuticals and nutraceuticals from various drug manufacturers and suppliers. Such therapeutic products include, but are not limited to, solid orally consumed doses, liquid orally consumed dosages, and injection devices that contain doses that are delivered or administered at the point of care. It will be understood that the term "medication" as used herein is intended to include individual, unit-of-issue doses of prescription and non-prescription medications, medical supplies, pharmaceuticals and nutraceuticals, in a variety of dosage forms and strengths, including single and multiple compound medications. Specific examples include pills, tablets, capsules, suppositories, inhalers, lotions, prefilled syringes, powders, suspensions, and diagnostic materials such as blood testing strips. At the control center 101, the typically foil-wrapped or blister-packed unit dose packages 27 are inserted into individual stalls 28 of one of several different medication carriers 26, each carrier being designed and sized to accommodate almost any commercially available unit dose package 27.

Exterior dimensions of the medication carrier 26 can be slightly varied, but must be configured to allow the carrier 26 to easily fit within the delivery module 33. An electronic code 29, such as a bar code or radio frequency identification tag, is affixed to each medication carrier 26. The electronic code 29 identifies the carrier type and configuration and provides medication related information, based on a unique identifier such as a serial number. The encoded data is programmed into the control center 101 computer database 35, enabling the control center 101 to accurately track and account for each unit dose package 27 at all times, in conjunction with the delivery module 33, as described below.

Figure 15:
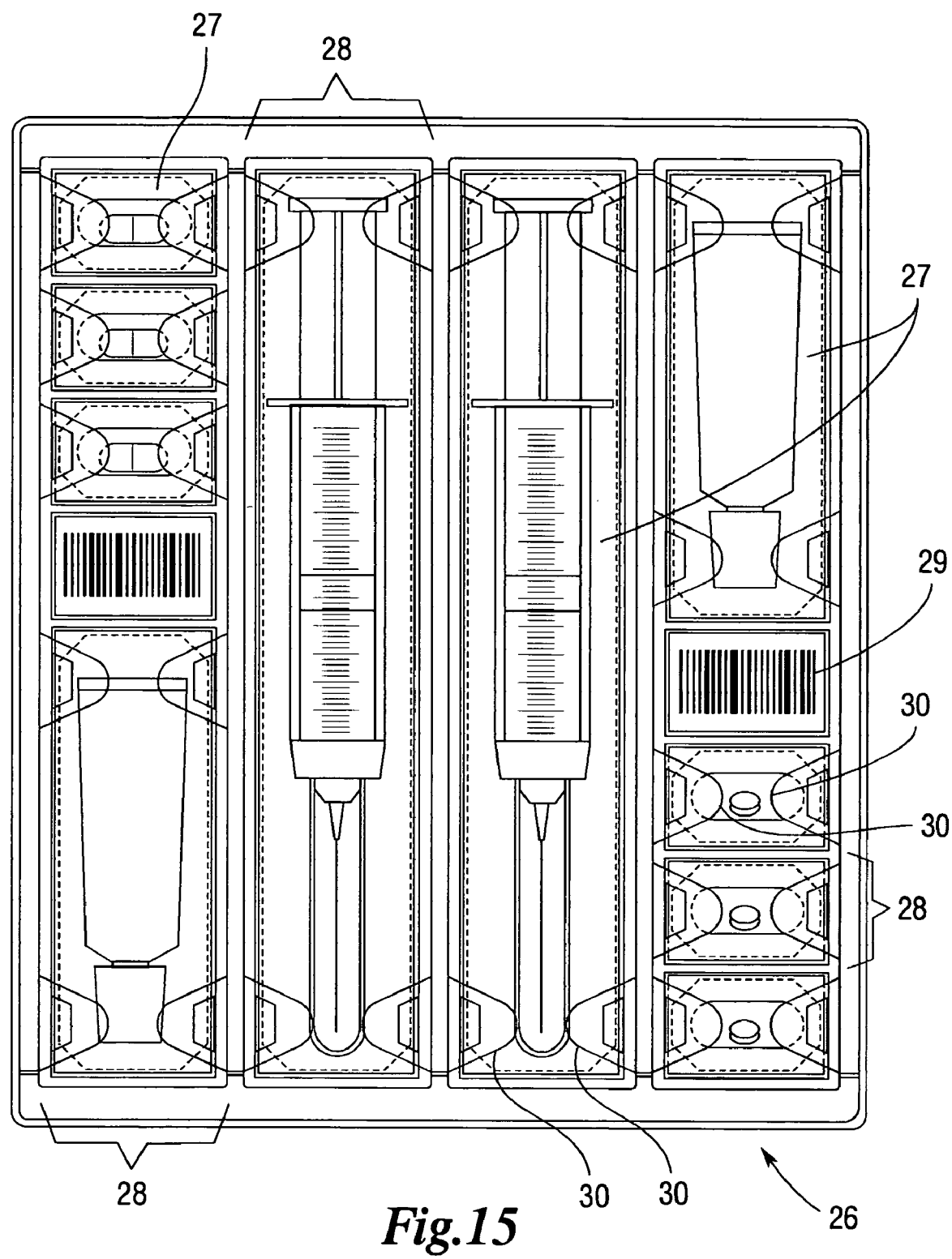
Figure 16:
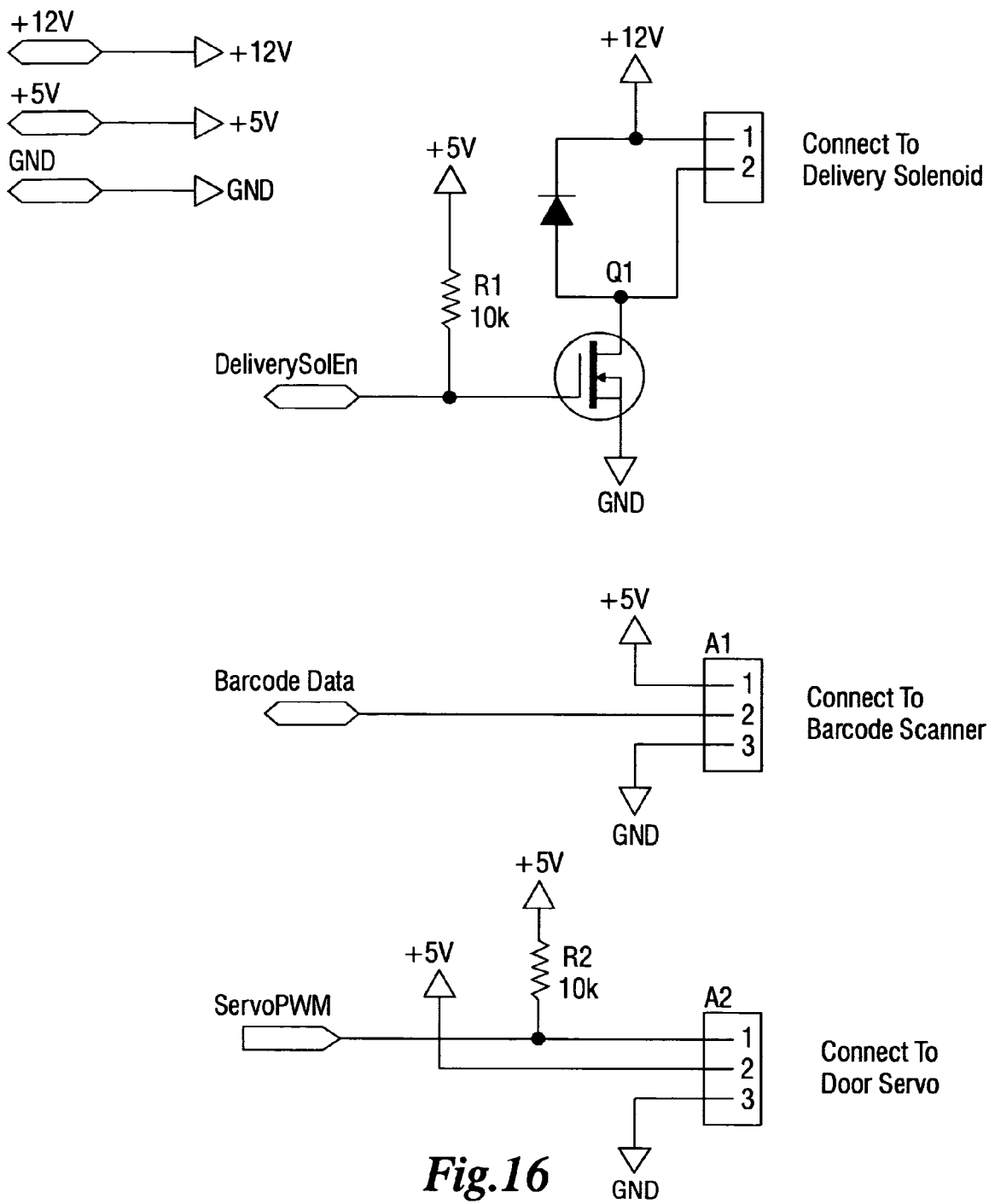
FIGS. 16-20 are electrical schematics illustrating various operations of the non-sequential medication delivery module in accordance with the present invention.
Figure 17:
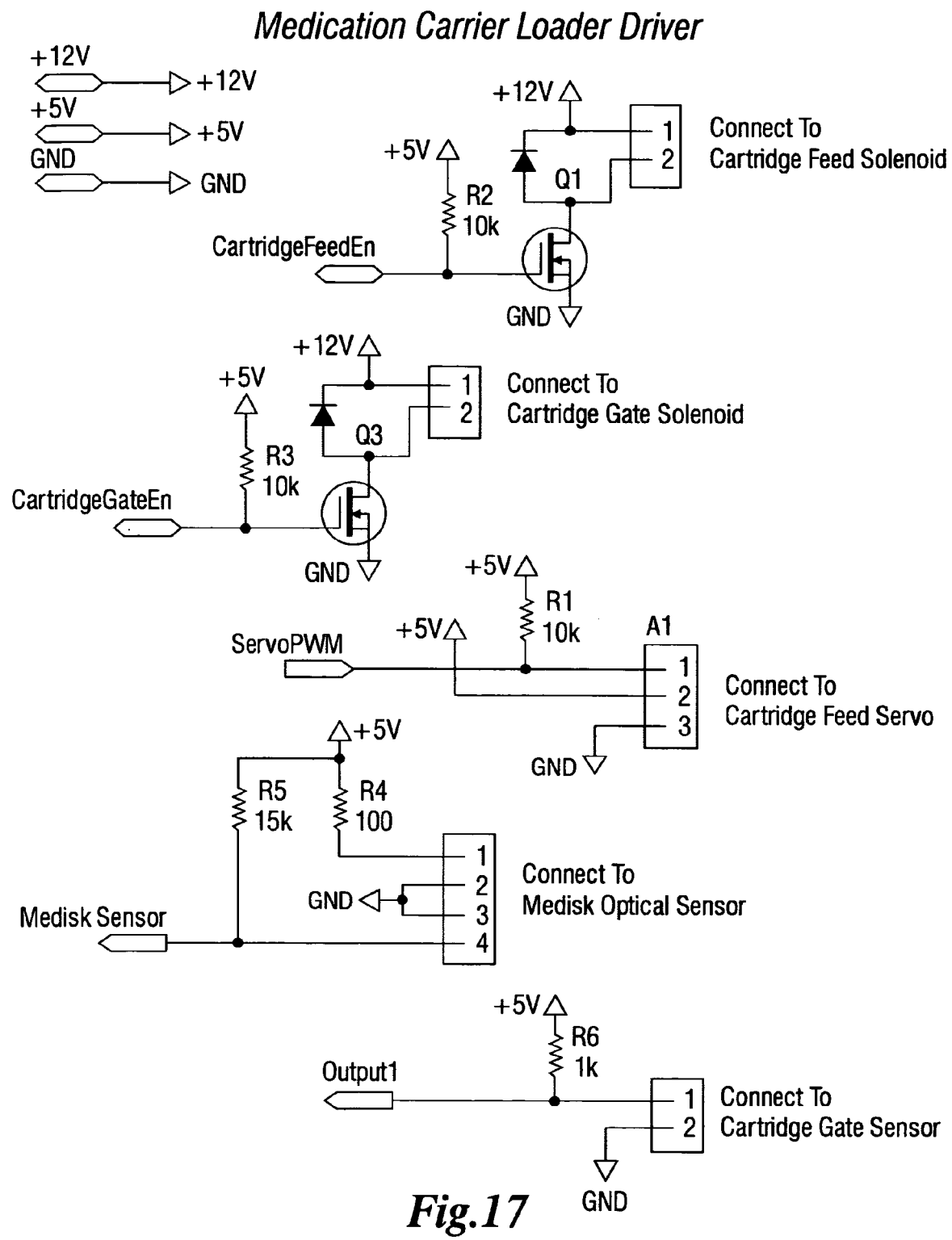

Referring to FIG. 15, the medication carrier 26 comprises a receptacle for holding individual, unit dose packages 27 in a non-sequential fashion. Standard unit dose packages 28 normally include a plastic bubble for holding the unit dose therapy and a seal fabricated from paper or foil laminate for retaining the unit dose within the plastic bubble. "Identifying indicia" 31 such as, for example, an electronic code and human readable information, is imprinted on the seal of the unit dose package 27 to denote the medication contained in such package. The medication carrier 26 is designed to permit the identifying indicia 31 to be electronically read by a bar code scanner 98, optical recognition scanner, radio frequency scanner or other such device, without removing the unit dose packages 27 from the medication carrier 26. The medication carrier 26 allows an individual, unit dose package 27 to be remotely and non-consecutively accessed and discharged from the carrier 26 without disrupting the other unit dose packages 27 contained therein.

Figure 21A:
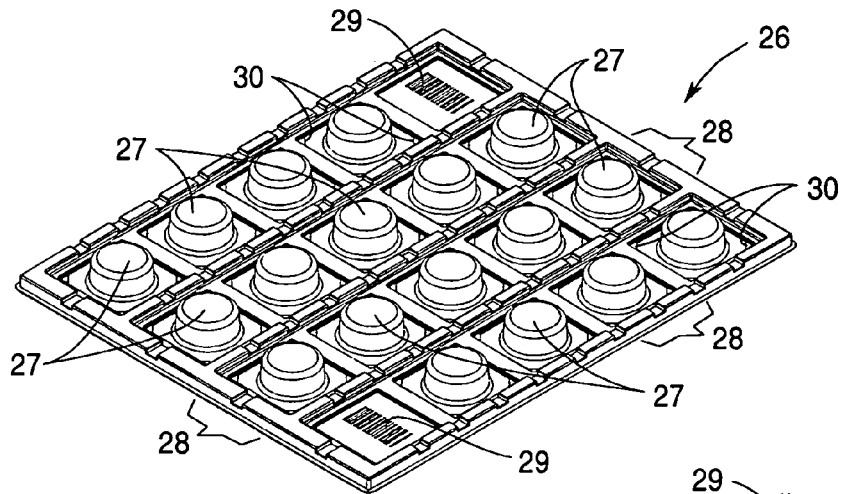
FIGS. 21a, b and c are perspective views of medication carriers containing 32, 20 and 16 stalls, respectively, for accommodating different sized unit dose packages.
Figure 21B:
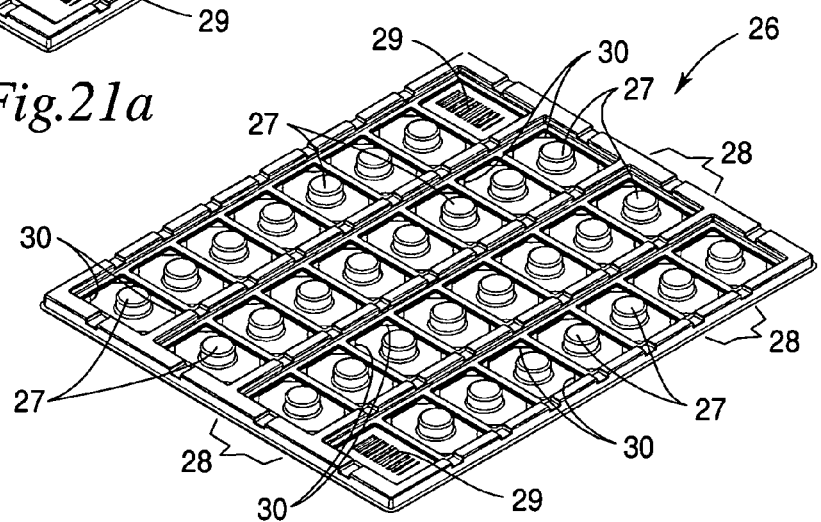
Figure 21C:
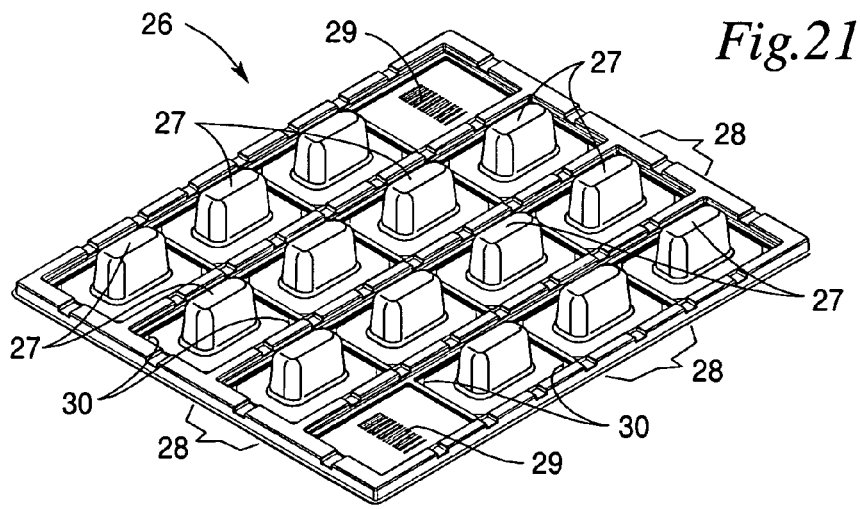

As shown in FIG. 21b, the medication carrier 26 may include 32 stalls arranged in four rows of eight stalls 28. In this arrangement, the carrier 26 stores medication for up to 30 calendar days and provides additional surfaces for affixing a label containing a unique electronic identifier 29. FIGS. 21a and 21c illustrate medication carriers 26 having 20 and 16 stalls, respectively, sized and shaped to accommodate larger unit dose packages 27. Each stall 28 of the medication carrier 26 includes retaining means 30 for holding the sealed, unit dose package 27 within the stall 28 until a scheduled dosing time. At such time, the unit dose package 27 is expelled through an aperture in said stall 28.

A printable surface containing identifying indicia is provided on the upper surface of the medication carrier 26, along its peripheral edges. The printable surface features location markers such as, for example, infrared absorbent ink dots which indicate certain points of interest on the carrier 26.

Normally, the delivery module 33 is remotely located from a clinical facility where healthcare personnel are based such as, for example, a physician's office, pharmacy, pharmacy benefit manager (PBM), hospital, outpatient clinic, nursing station, assisted living facility or long-term care facility. Each clinical facility is equipped with a computer that includes, for example, a standard microprocessor, input-output circuits, a memory for storing patient records including prescription and dosing schedules, a ROM for storing the operating program and other system information, and a monitor for receiving visual feedback. Software 32 such as the Fulfillment, Adjustment and Compliance Tracking System (FACT™), commercially available from INRange Systems, Inc., operates on computer servers at the clinical facility. Patient information is accessed by way of the software's 32 user interface 100, which features a complement of menu-driven worksheets that appear on the monitor of a designated healthcare practitioner (FIGS. 27-31).

The user interface 100 enables the healthcare practitioner to remotely and actively treat a patient by entering appropriate instructions into his/her computer terminal using a keyboard, mouse or other input device. The healthcare practitioner may, for example, input or retrieve prescription information, configure formularies or therapeutic regimens, remotely schedule a new regimen, monitor patient compliance with a dosing regimen, or modify the dosage amounts of an existing regimen. The entered instructions are transmitted to the control center 101, where the instructions are interpreted and routed to the appropriate delivery module 33 based on a unique identifier assigned thereto. The user interface 100 also displays real-time notification of dosage delivery results communicated to the clinical software 32, enabling the healthcare practitioner to take immediate action, if necessary.

The clinical software 32 is securely installed within the confines of each clinical facility and utilizes the facility's network security 34 policies and procedures to authenticate users and network access to patient data. As described below, the control center 101 has no access to patient identifiable information and cannot in any way determine the identity or location of any patient utilizing the delivery module 33. This secure technical and physical information infrastructure is in accord with the Health Insurance Portability and Accountability Act (HIPAA).

Control software 35 programmed to constantly monitor for signals from both the clinical software 32 and delivery module 33 is installed on computer servers based at the control center 101. The control software 35 administers the various treatment instructions entered by the healthcare practitioner, but does not implicate patient information stored within the software database 32 of the clinical facility. In general, the control software 32 records and stores information related to the operation and contents of the delivery module 33, such as the types and locations of medication carriers 26 stored within the module 33, a complete inventory of the unit dose packages 27 contained within each medication carrier 26, and a history of all dose administration operations over a set time period. This record keeping and inventorying function is achieved, in part, through the use of electronic coding and other identifiers which are assigned to the delivery module 33, medication carriers 26 and unit dose packages 27, respectively. The identifiers enable the control center 101 to correlate a particular medication carrier 26 to the inventory of unit dose packages 27 contained therein, with the assistance of electronic code scanners 92, 98 located within the delivery module 33 for imaging and transmitting encoded information to the controller.

A unique identifier such as a serial number (Unit Identification Number) is typically programmed into the delivery module 33 at the time of manufacture. Similarly, identifying indicia 31 (FIG. 14), including an electronic code and human readable information, is imprinted on the seal of each unit dose package 27 by the drug manufacturers or repackagers. The electronic code 31 identifies the package 27 contents, including, for example, the medication name, dosage strength, lot number, expiration date, national drug code number (NDC) and/or unique package serial number. A plurality of unit dose packages 27 representing a prescribed course of medication are placed into the stalls 28 of a medication carrier 26, in any order. The unit dose packages 27 need not be organized chronologically, as is required in the existing dosage delivery systems, since each package 27 is randomly accessed and retrieved. The identifying indicia 31 on the seal of each unit dose package is scanned into the control center computer so that an audit trail of each package 27 is maintained.

The control software 35 assigns a unique identifier 29, such as a serial number, to the medication carrier 26. The identifier 29 correlates the medication carrier 26 to the inventory of unit dose packages 27 contained therein and denotes the contents and location of each unit dose package 27. The carrier identifier 29 is reflected within one or more electronic codes which are printed onto a label and affixed to separate locations on the medication carrier 26. This redundancy ensures that at least one electronic identifier 29 is accessible to a code reader 92, 98. This information is stored within the control software database 35.

As discussed above, the unit dose packages 27 are placed into one of several different medication carriers 26, according to the size and configuration of the package 27. For instance, packages containing syringes are typically placed in a medication carrier 26 having longer and wider cells, while packages of oral solid doses are normally placed in a carrier 26 containing smaller cells. Position coordinates, based on the internal geometry of the medication carrier 26, are stored in the control software database 35 to pinpoint the location of each unit dose package 27 within the carrier 26. These coordinates are also reflected in the electronic identifier label 29 that is affixed to the medication carrier 26. The carrier 26 can be inserted into the delivery module 33 in more than one way. Therefore the control software 35 also generates a set of location markers such as, for example, infrared absorbent ink dots or lines which indicate certain points of interest on the carrier 26, which are included on a printable surface (e.g. cardboard) preferably disposed on the upper surface of the medication carrier 26. This redundancy ensures that at least one location marker can be imaged by an optical recognition reader or other electronic scanner 98.

Communication between the delivery module 33 and a healthcare practitioner is accomplished through the control software layer 35. Contained within this layer are the communication protocols for each delivery module 33, which correspond to the type of communication link that is selected for a particular module. Suitable communications media 36 include radio frequency, internet, modem, telephone line, land line, wireless network, pager network or other transmission means that enables control and data signals to be exchanged with the delivery module 33. Preferred communications media include dedicated Local Area Network and/or existing Local Area Networks (e.g. copper, fiber or wireless). The control software 35 communication protocols enable alert signals to be conveyed from the delivery module 33 to the clinical facility 32 to notify appropriate medical personnel of patient non-compliance actions or other urgent conditions. The control software 35 protocols also enable the control center 101 to accurately monitor each unit dose package 27 contained within a particular delivery module 33 and update the database inventory records as each unit dose package 27 is delivered to a patient.

In order to ensure the security of patient information transmitted through the control software layer 35, a preferred embodiment of the present invention utilizes a secure, encrypted connection 25 which maintains the confidentiality and integrity of patient information. The data communication process ensures that the only record correlating a delivery module 33 to a particular patient is contained within the clinical software database 32. This process is described in detail below.

As previously discussed, the clinical software 32 enables a healthcare practitioner to remotely manage and monitor a patient's drug therapy and compliance. All patient information is stored in the clinical software database 32 and utilizes the clinical facility's network security 34 policies and procedures to authenticate users and network access to patient data (FIG. 2). Contained within the clinical software 32 are three key data elements that correlate the delivery module 33 to a particular patient. These include: 1) the delivery module serial number; 2) a randomly generated registration number (used in the initial setup of the module), and 3) a randomly generated Unit Identification Number (UIN).

To communicate with a delivery module 33, the clinical software 32 sends an encrypted signal using a Secure Socket Layer ("SSL") to the URL of the control center 101 computer servers. This signal is the same protocol used in processing credit card payments via the internet and operates on Port 443 of the clinical facility's firewall 34. The signal is an XML instruction set that contains the UIN, identifiers required for authentication by the control center 101 servers, and a command instruction set. Neither the patient's name nor any information identifying the patient are transmitted beyond the clinical facility's firewall 34.

This encrypted signal is sent to the control software layer 35, which is designed to authenticate signals from only the clinical software 32 and delivery module 33. Once a command set is authenticated by the control center 101 servers, utilizing the UIN, the command set references the control software database 35 to determine the data communications method 36 to the particular delivery module 33 (e.g. pager network, wireless network, IP address) and obtains its address information. The signal is reformatted into a proprietary protocol, assigned a randomly generated communication's token and transmitted to the delivery module 33 to be activated.

Once the signal is received by the delivery module 33, the signal is decoded and verified. If authentic, the delivery module 33 transmits a signal back to the control center 101 servers confirming receipt of the command instruction. This confirmation contains the communications token for verification by the control center 101 servers. Certain commands, such as the dosage delivery command, require a reconfirmation from the control center 101 servers to engage the command. This verification process prevents the delivery module 33 from processing any unauthorized commands.

The data communication process 36, as described above, ensures that only the clinical software 32 can correlate data contained on the control center 101 servers to a particular patient, or correlate the delivery module's serial number to a particular patient. In this manner, patient identifiable health information is retained securely within the confines of the clinical facility 34. A principal advantage of the present invention, therefore, is that it enables bidirectional communication between the delivery module 33 and a healthcare practitioner to be conducted using a secure, encrypted connection 25 that maintains the integrity of HIPAA protected patient information.

It will be understood that the present invention may be employed in connection with "non-HIPAA compliant" applications. Stated otherwise, the secure, encrypted data transmission protocol 25 provided herein is not necessary for remote actuation of the delivery module 33. For example, the invention may be used independently of the secure data transmission feature 25 to document various drug consumption events that occur during the course of a clinical research trial or drug detoxification program. In this way, the invention provides a means of capturing longitudinal healthcare outcomes associated with drug and nutritional interventions. Similarly, the delivery module 33 may be employed in connection with a home telemetry unit for remote monitoring of a patient's position, blood pressure, pulse, oxygen level, temperature, respiration, serum glucose etc., or for remote monitoring of environmental conditions such as, for example, temperature, humidity, pressure, smoke and carbon dioxide.

The non-sequential delivery module 33 features a microprocessor-based controller having standard digital data storage features both for data and for the microprocessor programs. The controller receives command signals related to the patient's prescribed medication regimen. These signals, initiated at the clinical software layer 32, are authenticated and transmitted through the control layer 35 by way of a suitable data communications link 36. The controller then executes the entered dosage delivery command by alerting the patient through visual, audible or other means, at each of the programmed dosing times. The controller concurrently establishes a window of time, relative to the alerting signal, during which the patient can input a delivery signal via, for example, a verbal command or an appropriate confirmation key 43. The duration of the time window is set by the entered program or by a default value.

If the patient input signal is received before expiration of the time window, a fully sealed unit dose or unit-of-issue package 27 is ejected from the medication carrier 26 and discharged from the delivery module 33 as described in further detail below. If the patient has not responded, e.g., pressed the "drop" key 43 of the delivery module 33 at the end of the time window, the module automatically transmits an alert, via a suitable data communications link 36, to designated medical personnel. In this manner, the instant invention ensures that medication is not administered until confirmation is received from the patient. This overcomes a significant deficiency of existing medication delivery systems, in which medication is expelled automatically in accordance with a predetermined schedule, increasing the risk of patient under-dosage and over-dosage.

The present invention includes a unique delivery scheme through which a healthcare practitioner, by entering appropriate commands into the user interface, can instantaneously select, modify, queue, change or discontinue any of 300 unit dose packages 27 of prescription or non-prescription medications, pharmaceuticals or nutraceuticals stored within the delivery module 33 of a particular patient. The commands also specify the specific dosage form and strength of the unit dose package 27 to be delivered. The commands are received and interpreted by the control center computer servers, which correlate the instruction to a particular delivery module 33 and medication carrier 26. In this manner, the invention provides the flexible and convenient dosage administration that is required for situations where a patient's regimen is the subject of frequent dosage adjustments or where the patient is prescribed more than one therapy to be administered at varying times over the course of a day, a week or several months.

The present invention enables the healthcare practitioner to remotely and non-consecutively access and deliver any of the unit dose packages 27 contained within the delivery module 33 to a patient, in any order, without being limited by a predetermined sequence or serial delivery restriction. Unlike existing systems, the system of the present invention is capable of delivering diverse types of unit dose and unit-of-issue therapeutic products out of sequence, and in minutes, enabling the patient's medication regimen to be appropriately tailored to adapt to fluid medical conditions. An example circumstance requiring modification of the patient's regimen is where there is an unexpected change in the patient's health condition. Notably, the invention ensures that any change in patient medication ordered by a doctor is effective immediately. This is a tremendous advantage over existing systems, which take at least several hours, and in some cases, several days for new medication orders to be filled.

Figure 26:
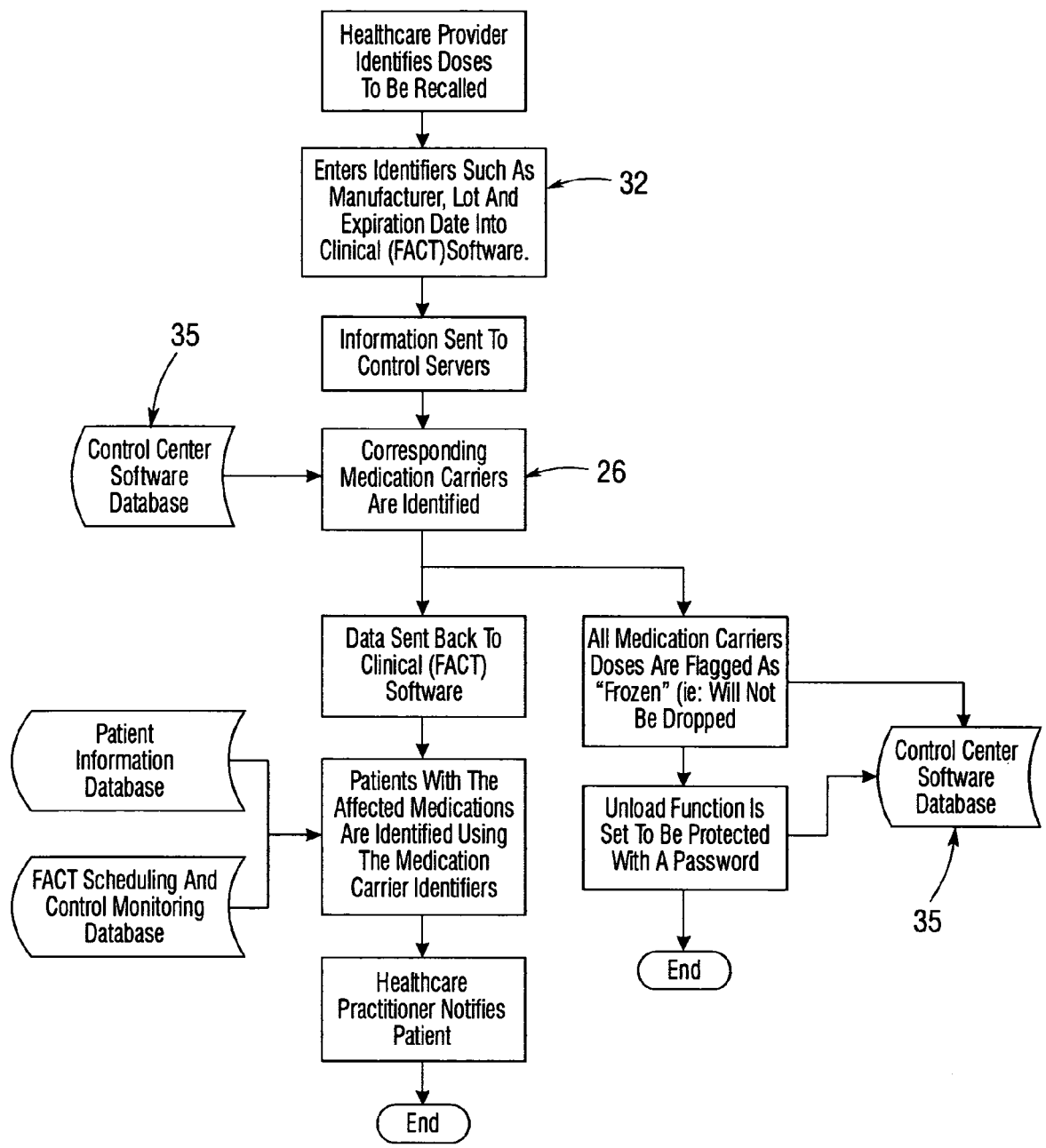
Figure 27:
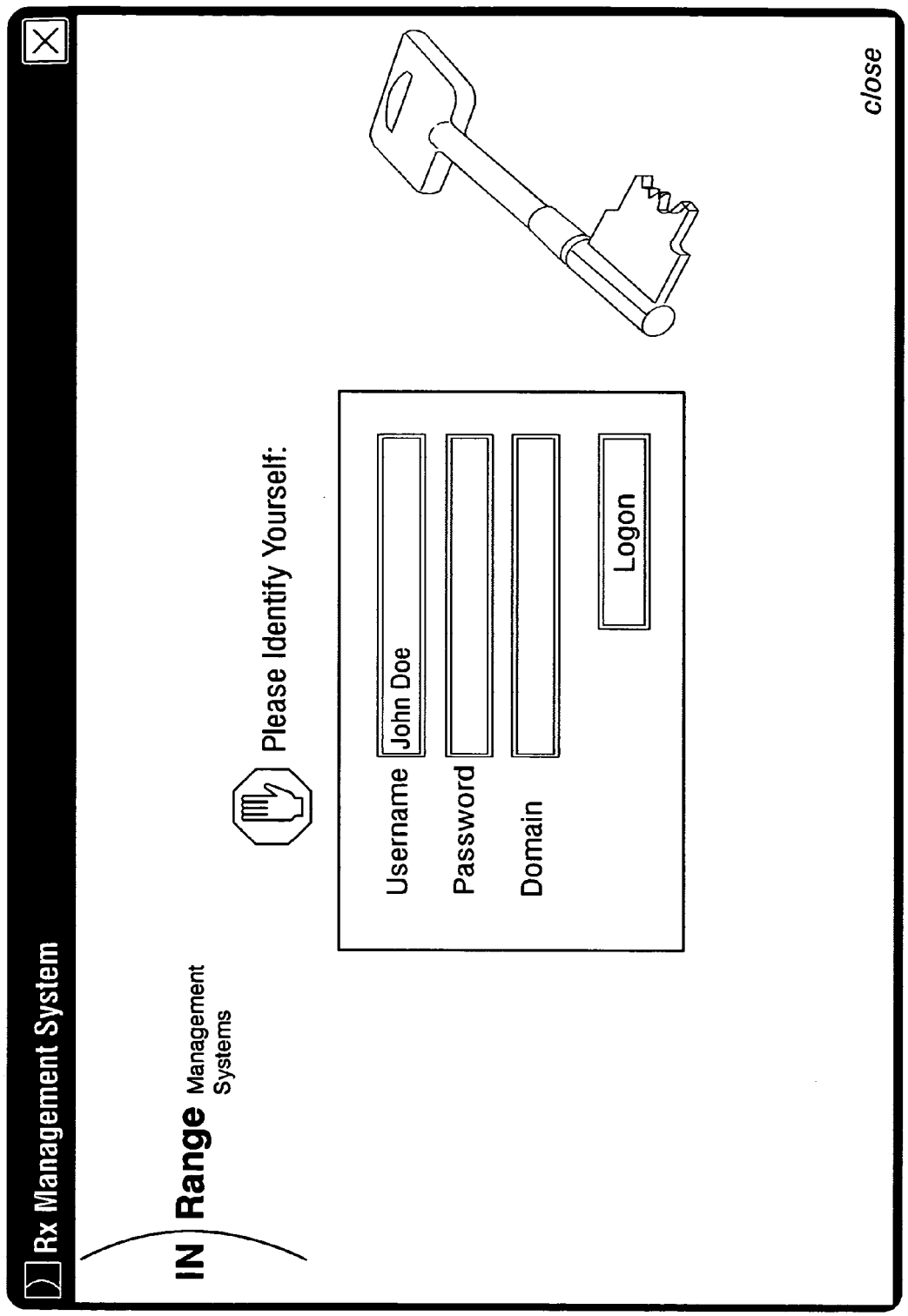

The subject invention is particularly useful in situations where it is necessary to immediately discontinue or recall a therapy prescribed as part of a clinical research trial, a frequent occurrence (FIG. 26). In such instances, the clinical software initiates a lock-out procedure to prevent delivery of any of the unit dose packages that have been recalled. To the inventors' knowledge, the present system is the only technology platform that enables real-time quarantine of remotely located products/lots. In this way, the invention provides a unique safeguard that protects patients in the event of a drug recall. This feature is particularly important with respect to narrow therapeutic index drugs that are mislabeled, subpotent or superpotent.

The delivery module 33 is designed so that each unit dose and unit-of-issue package 27 ejected from the medication carrier 26 remains fully sealed until the point of delivery to a patient. Therefore, the present invention avoids the medication contamination and degradation problems common to medication delivery systems known in the art.

A further embodiment of the invention combines an early dosing capability with the programmed regimen delivery described above. In this embodiment, the delivery module 33 has an added programmability feature by which a designated healthcare practitioner, by entering appropriate commands into the user interface 100, can obtain an early delivery of one or more unit dose packages 27 of the patient's medication. An example circumstance requiring this would be where the patient intends to temporarily leave his/her residence, during which time medication would still be needed, regardless of the patient being remote from the delivery module 33. In emergency situations, the medication carrier 26 may be removed from the delivery module 33 for out-of-system use. In such situations, access to the delivery module 33 may be granted to the patient or other authorized personnel by means of a security code, video/smart card or other appropriate safeguard.

As described above, the control center 101 server is connected to the non-sequential delivery module 33 via, for example, a radio frequency connection 36, wherein the control center 101 is provided with a record keeping and inventorying function. In addition to one or more clinical facilities receiving alerts from the delivery module 33, information regarding the module's 33 operation, status and unit dose/ unit-of-issue package 27 inventory is automatically transmitted to the control center 101 server. This information includes, for example, a history of all delivery operations over a set time period. Reporting to the control center 101 is achieved, in part, through the use of electronic codes 29, 31 imprinted on each medication carrier 26 and on each unit dose package 27 contained therein. The electronic code 29 contains identifying information, such as, for example, the serial number, lot number, and expiration date of an individual unit dose package 27. In this way, the invention permits a continuously updated, complete inventory of each medication carrier 26 and unit dose package 27 stored within the module 33 to be maintained, and simultaneously provides a complete audit trail of each unit dose package 27 from its manufacture to delivery to a patient.

Although the control center 101 maintains a record of the encoded information 29, 31 in its computer server, patient identifiable information is inaccessible to the control center 101 and is securely maintained within data servers physically located within the confines of each clinical facility 34. The electronic identifiers 29, 31 imprinted on the medication carrier 26 and unit dose/unit-of-issue packages 27 do not include patient identification information. Instead, the medication carrier 26 is identified according to its uniquely assigned serial number 29, while each unit dose package 27 is identified according to serial number and/or national drug code number (NDC) 31. As such, the present system is compliant with the Health Insurance Portability and Accountability Act (HIPAA).

In a further embodiment, which may be combined with the above-described reporting function, the control center 101 sends queries to the delivery module 33, e.g. via radio frequency transmission 36, requesting inventory status information. The specific apparatus and details of operation of the delivery module 33 are described further below.

Figure 1:
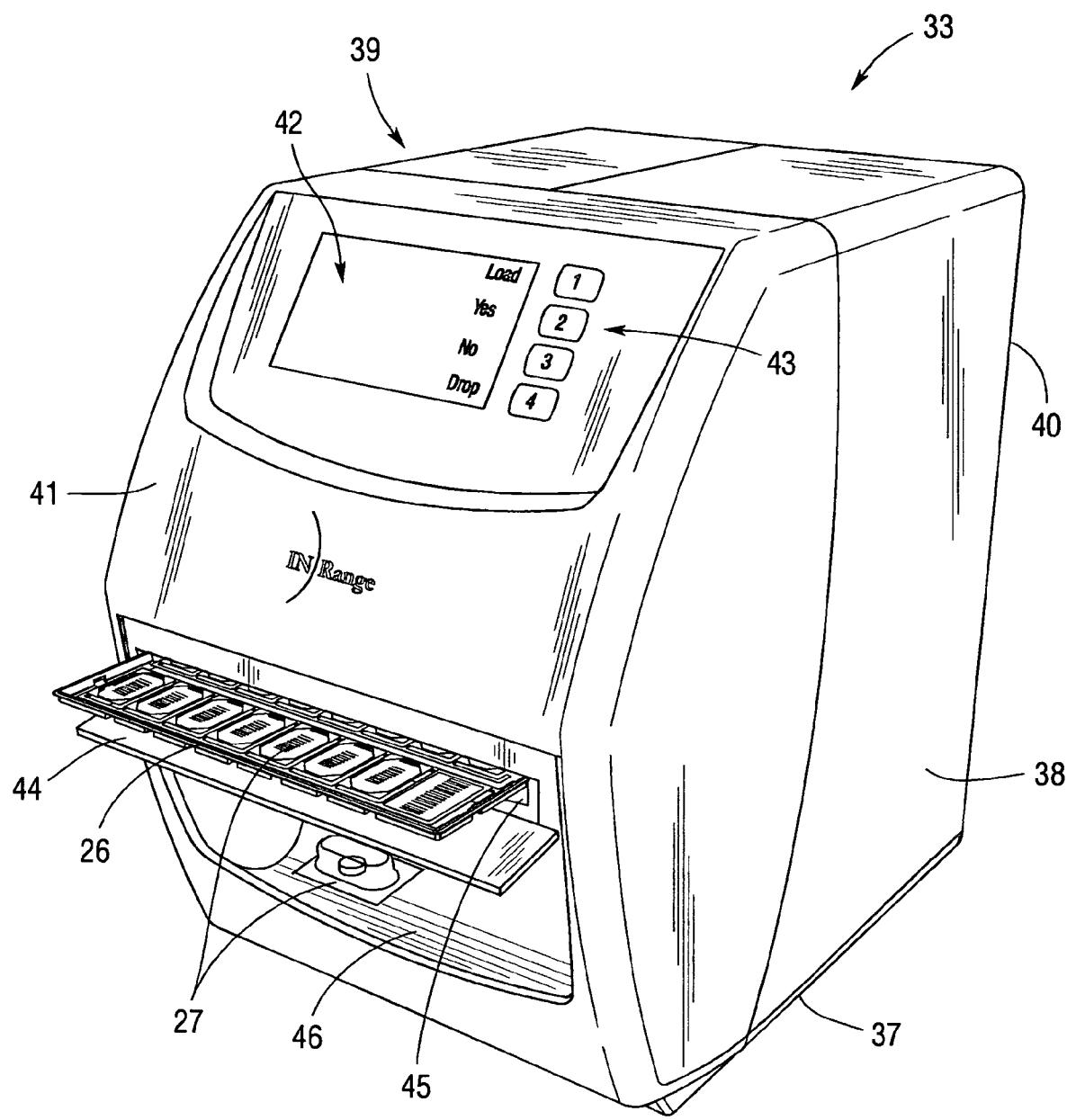
FIG. 1 is a perspective view of a non-sequential medication delivery module in accordance with one embodiment of the invention.

There is shown in FIG. 1, a delivery module 33 comprising a preferably plastic, box-like housing adapted to rest upon a surface and having a base 37 which supports top, side 38, 39, front 41 and rear 40 panels. The front panel 41 features an electronic display 42 on which alphanumeric information and instructions related to a particular unit dose are communicated to the patient. The electronic display 42 may comprise, for example, a liquid crystal display, digital display or other suitable communication means. Portions of the front panel 41 are also configured with an audible alarm to alert the patient of the need to take a prescribed unit dose package 27. To allow for patient input, the front panel 41 of the housing includes control keys 43 that function as confirmation keys in accordance with the audible alarm and electronic display 42 to enable the patient to take delivery of a prescribed dosage. An audio speaker and remote communication interface may optionally be incorporated within the housing for providing additional instructions to or receiving feedback information from the patient. An alternative embodiment of the invention includes temperature control means (e.g. refrigeration means) for regulating the temperature of the module 33 as may be required for certain medications. A power outlet allows the delivery module 33 to be connected to an external AC power source.

In a further embodiment, the invention includes a wireless communication device worn by the patient which is communicatively linked with the delivery module 33 to provide an additional alert to some patients. The wireless communication device may be, for example, a wrist watch, pager or pendant. Alternatively, a patient may be alerted via telephone or email.

Access to the medication carriers 26 and internal hardware of the delivery module 33 is provided when the side panels 38, 39 are unlocked and open. In order to prevent unwanted access to the medication carriers 26, the side panels 38, 39 may remain locked at all times unless actuated by the controller in response to a command originating from the control center or clinical facility. Alternatively, access to the interior of the module 33 can be granted to a patient, designated caregiver or other authorized personnel by way of a smart card or security access password. The smart card or restrictive password must typically be entered prior to interacting with the delivery module in instances where one or more unit dose packages have been quarantined or recalled. In a further embodiment, the delivery module 33 includes speech recognition means for receiving and interpreting prescribed verbal commands made by the patient or other authorized personnel.

In a manner well known in the art, each constituent of the delivery module 33 is operatively coupled to and controlled by the controller, through control signals, in response to a command instruction set received from a computer server based at the control center 101. The controller transmits verification to the control center 101 that information has been received and instructions have been carried out. The controller is programmed to activate the dosage "drop" function at appropriate times based on information remotely communicated from the control center 101. In particular, the controller activates the alarm, key pad 43, wireless communication circuitry, electronic display 42, sensors, scanners 92, 98, actuators 60, 72, 91, motors 54, 73, 80, 87 and other electronic devices.

The controller can be one of several standard microprocessor-based controllers having standard type actuator or servo drive interfaces and detector inputs, or other suitable circuitry capable of employing software control, hardware control or a combination thereof. Internal memory is used to store, for example, dosage delivery instructions and logic programs. The controller runs the programs stored in internal memory. Control signals travel by way of a distribution panel to and from the various components configured within the delivery module 33. FIGS. 16-20 further illustrates the controller's mode of communicating with electronic architecture of the delivery module 33.

Figure 14:
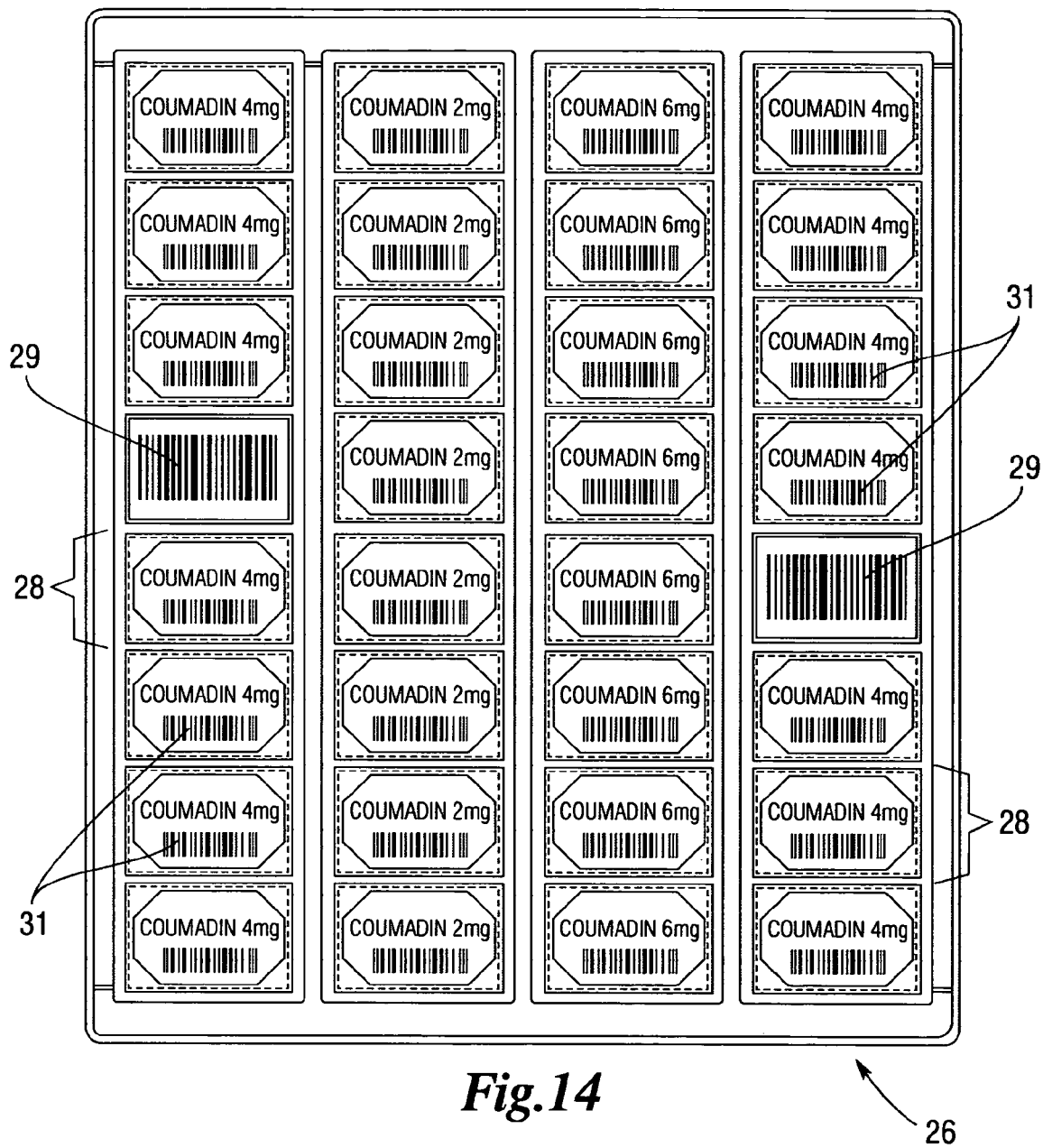
FIGS. 14 and 15 depict medication carriers containing unit dose packages of varying strengths in accordance with the present invention.

In the exemplary embodiment shown in FIG. 6, a storage elevator 47 is designed to accommodate up to ten medication carriers 26, each containing a thirty day supply of different therapeutic agents in a variety of dosage forms and strengths. The delivery module 33 is therefore capable of storing approximately three hundred unit dose and unit-of-issue packages 27 of medication. As shown in FIG. 14, each carrier 26 may include different dosage strengths for a single medication. This allows different dosage strengths to be combined to obtain a desired dosage amount. While the instant design is appropriate for use in a home, assisted living facility, long-term care facility or other residential setting, a delivery module 33 having a storage elevator 47 that can accommodate, for example, up to three hundred medication carriers 26 is preferable for use in an institutional environment (e.g. a correctional institution).

The location of each unit dose package 27 and medication carrier 26 within the delivery module 33 is determined, in part, through the use of electronic identifier codes 29, 31 or other inventory code systems. The electronic codes 29, 31 imprinted on the medication carriers 26 and individual unit dose packages 27 are scanned by an electronic code reader 98 as each medication carrier 26 is loaded into the delivery module 33. The encoded information is transmitted to the control center 101 computer server, where it is associated with a stored database record by the control software 35. This information allows a healthcare practitioner to actively treat a patient remotely located from a clinical facility.

The healthcare practitioner, by way of the menu-driven user interface 100, simply retrieves and reviews the inventory of unit dose and unit-of-issue packages 27 stored within the patient's delivery module 33 and selects an appropriate dosage within the parameters prescribed for the patient. Upon receipt of a command signal from the control center 101 computer server, the patient's delivery module 33 expels the selected dosage based on the electronic identifiers 29, 31 and position coordinates of such dosage within the delivery module 33.

As shown in FIG. 6, the storage elevator 47 includes a cavity which is partitioned into multiple storage bays 48 disposed on separate levels of the elevator 47. Each storage bay 48 has a horizontal opening of a sufficient size to provide the range of motion necessary to allow a transport carriage 49 stored within the bay 48 to be moved in both forward and rearward directions. The transport carriage 49 comprises an open-ended frame that defines a fluting 50 disposed along the length of said frame, such that peripheral edges of the medication carrier 26 can be readily fitted within said fluting 50. The carriage 49 is supported by a horizontal railing 51 which extends along the interior surfaces of the storage bay 48. Ends of the railing 51 terminate about a concentric shaft 52 that is generally flush with the opening of the bay 48.

Rotatable spur gears or sprocket drives 53 are mounted at both ends of the shaft 52 so as to come into contact with and suitably engage corresponding stationary gears that protrude from peripheral edges of the carriage 49 for effecting forward and rearward movement of the transport carriage 49. The spur gears 53 are rotated by a drive motor (e.g. a servo motor) 54 in a controlled fashion, in response to signals from the controller. While a gear assembly is described herein for moving the transport carriage 49 in both forward and rearward directions, it should be understood that any suitable drive assembly may be employed. Location markers are provided along an outer edge of the transport carriage, which indicate the exact horizontal position ("y-axis") of the carriage 49 and integral medication carrier 26. This information is monitored by the controller through a feedback loop arrangement. Once the controller determines that an appropriate number of markers have been scanned by an electronic code reader 98 mounted within the storage elevator, the drive motor 54 is disengaged. The transport carriage 49 normally resides within the storage bay 48 (the "home position" 99) until a prescribed dosage is to be taken or a medication carrier 26 is to be replenished.

Figure 9:
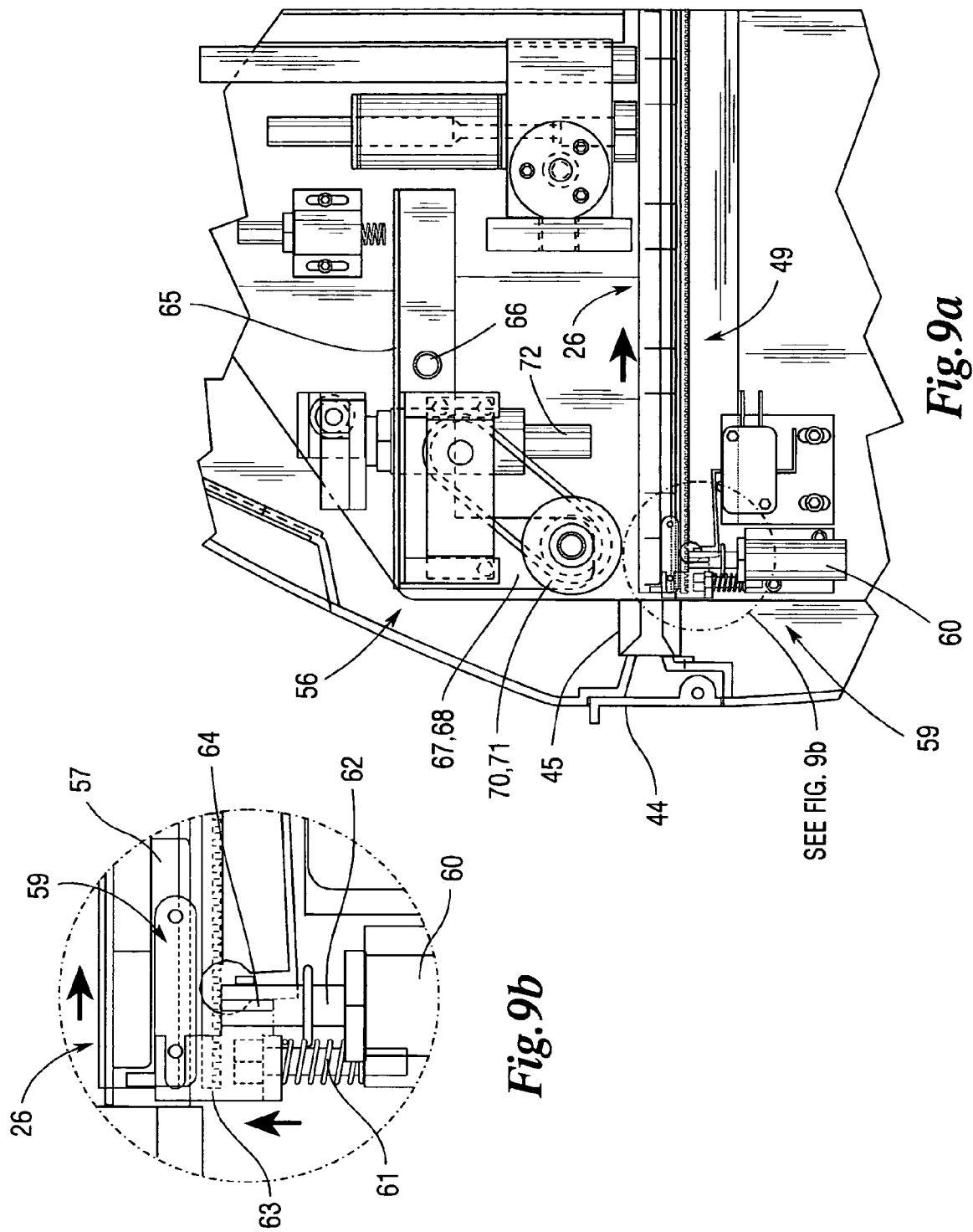
FIG. 9a is a cross-sectional view of a medication carrier fully inserted into the delivery module.
FIG. 9b is an exploded view of the latch apparatus in a locked position.
Figure 10:
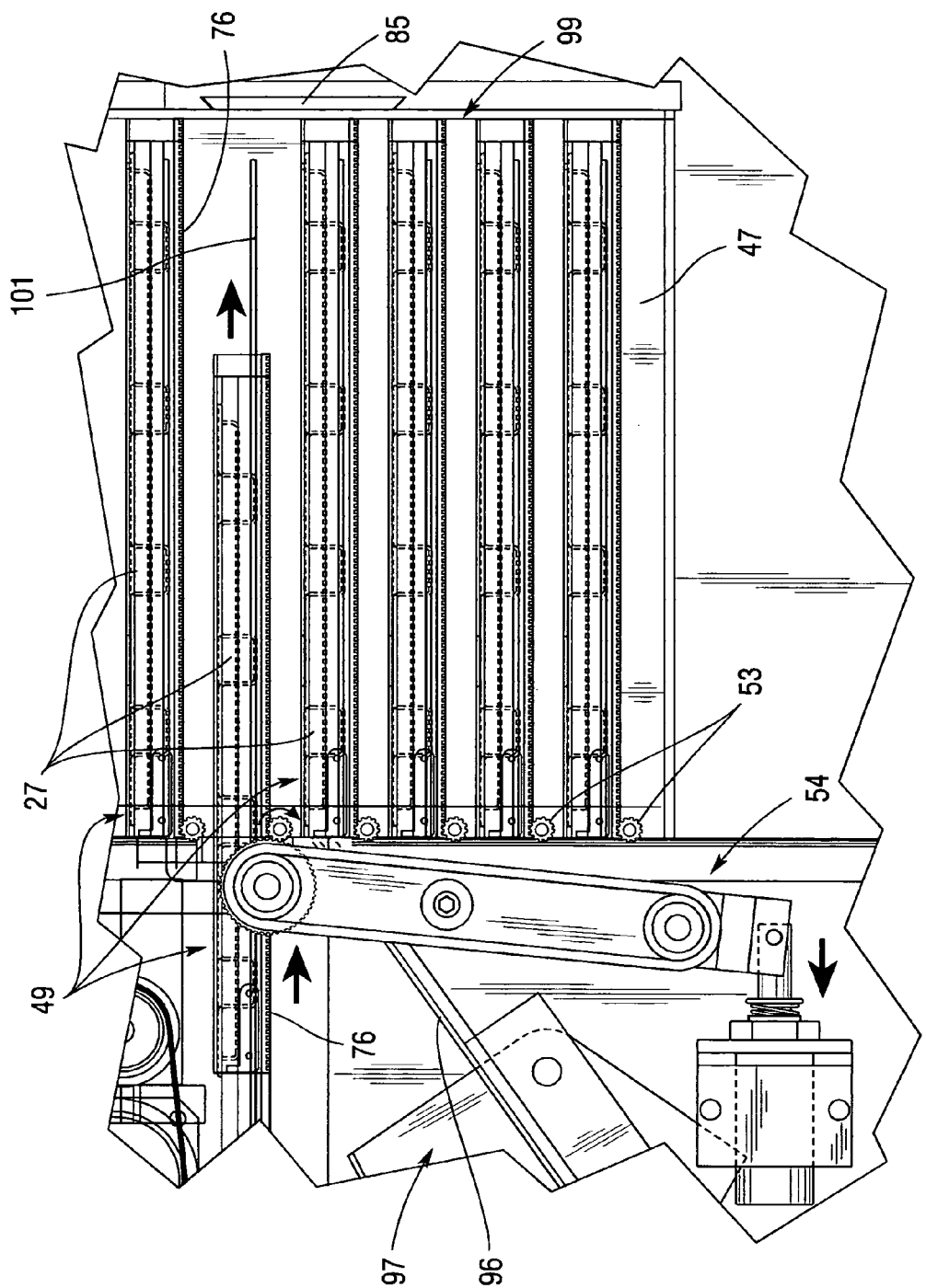
FIG. 10 is a cross-sectional view illustrating the mechanism of operation of the carriage drive assembly in accordance with one embodiment of the invention.

As discussed above, the transport carriage 49 is adapted for horizontal (x-axis) movement between rear and forward positions (FIGS. 9 and 10). Upon receiving a "dose delivery" signal from the controller, the drive motor 54 rotates spur gears 53 of the desired storage bay 48, such that the carriage 49 and integral medication carrier 26 are moved in a forward direction, sufficiently to clear the opening of the storage bay 48, and achieve a "delivery ready" position in proximity to a vertically disposed plunger 93. Likewise, during a carrier 26 unloading operation, the drive motor 54 advances the transport carriage 49 to a forward position in which a portion of the carriage extends beyond the opening of the storage bay 48. At such point, additional forward movement of the carriage 49 is accomplished through the action of a friction drive assembly 56. Sensors are located to monitor the movement and alignment of the transport carriage 49 as it is moved in both forward and rearward directions.

Referring now to FIG. 1, a handle equipped loading door 44 and insertion/retrieval slot 45 are provided in the front panel 41 of the housing. When the door 44 is open, the slot 45 is accessible for inserting a medication carrier 26 filled with unit dose packages 27 of prescription or non-prescription medications and supplies. Adjoining the interior surface of the front panel 41 is a loading area with components for receiving the medication carrier 26 into the delivery module 33. Each of these components will be described in detail below in reference to FIGS. 7-10 and 17.

A sensor is located in the loading area to detect the presence of an incoming medication carrier 26. The sensor is, for example, a micro-switch, optical eye or other electrical contact suitable for monitoring the orientation of the medication carrier 26 relative to a limit switch embedded within the loading area. When the sensor detects that the medication carrier 26 has been fully inserted, through activation of the limit switch, a friction drive assembly 56 is immediately actuated.

A pair of parallel guide rails 57, 58 are horizontally mounted to the side panels 38, 39 to enable the transport carriage 49 and an incoming medication carrier 26 to be properly aligned and dispatched through the loading area of the housing to the storage elevator 47. One end of each of the guide rails 57, 58 abuts the interior surface of the front panel 41 such that the guide rails 57, 58 at that point intersect the insertion/retrieval slot 45 configured in the front panel. The guide rails 57, 58 extend through the midsection of the housing and terminate in front of the storage elevator 47.

Latch apparatus 59 is configured to allow the incoming medication carrier 26 to be secured onto the transport carriage 49 and dispatched through the loading area. The latch apparatus is 59 operatively coupled to a solenoid 60, or other electromechanical actuator, which is mounted to a side panel 38 of the housing by a bracket and screws, or similar hardware. A retractable spring 61 and plunger 62 are provided at the upper end of the solenoid 60, the plunger 62 including a groove 64 in a top portion thereof which supports one end of the latch apparatus 59. An opposite end of the latch apparatus 59 features an angle 63 that abuts peripheral edges of the guide rail 57 and vertically protrudes above the guide rail 57 so as to obstruct the loading pathway.

Upon actuation by the controller, the solenoid 60 biases the spring 61 and plunger 62 downward. This, in turn, lowers the latch apparatus 59 to a position below the guide rail 57 so that the transport carriage 49 can be positioned on the exposed, upper surface of the guide rails 57, 58 for movement beyond the storage bay 48 to a "prime" position, planate with the front panel 41 of the housing. The solenoid 60 retains the latch apparatus 59 in this suppressed orientation while the medication carrier 26 is loaded into the delivery module 33, through the insertion/retrieval slot 45. As the incoming medication carrier 26 enters the loading area, the carrier's 26 peripheral edges automatically slot into the carriage fluting 50 so as to form an integral unit therewith for transport to a storage bay 48. At such time, the latch apparatus 59 is returned to its initial, indexed position against the peripheral edges of the guide rail 57 under the force of the solenoid 60.

A short distance above the guide rails 57, 58 is a swivel bracket 65 which is mounted to and pivots about a horizontal rod 66 attached to the side panels 38, 39 of the housing. The bracket 65 is configured for mounting a friction drive assembly 56 that controls movement of the transport carriage 49 and medication carrier 26 through the loading area. The bracket 65 forms an arch about its anterior, peripheral edges which features opposing vertical flanges 67, 68. The flanges permit a drive shaft 69 and a pair of drive wheels 70, 71, spaced substantially equally apart, to be conveniently attached to the bracket 65. It should be noted that the drive wheels 70, 71 are preferably made of rubber, soft, compressible polyurethane foam or other material that is capable of gripping a medication carrier 26 containing individual unit dose packages 27 without breaking or damaging the medication contained therein. Vertically suspended from an opening in a top surface of the bracket 65, directly above a guide rail 57, is an electromechanical actuator 72 which distends to mate with and exert pressure on an upper surface of the medication carrier 26, in response to a control signal. This action causes the bracket 65 to pivot downwardly, so as to assume an angled position and lower the drive wheels 70, 71 onto the upper surface of the transport carriage 49.

A drive motor 73 such as, for example, a servo motor, is secured to the swivel bracket 65 and operatively coupled to a pulley system 74. The pulley 74 is mounted in perpendicular relation to the drive shaft 69 and is moveable relative thereto by means of the motor 73. Upon actuation, the motor 73 rotates the pulley 74, which in turn, rotates the drive wheels 70, 71. The rotary motion of the drive wheels 70, 71 directs the medication carrier 26 and transport carriage 49 inwardly, toward the storage elevator 47. Once the transport carriage 49 and carrier 26 reach the opening of the vacant storage bay 48, the carriage's 49 protruding gear elements engage rotatable spur gears or sprocket drives 53 mounted about the opening of the storage bay 48, moving the carriage 49 and medication carrier 26 toward the rear of the storage bay 48. When the sensor detects that the medication carrier 26 and transport carriage 49 have arrived at their home position 99, the controller disengages the motor 73 and drive wheels 70, 71.

Figure 3:
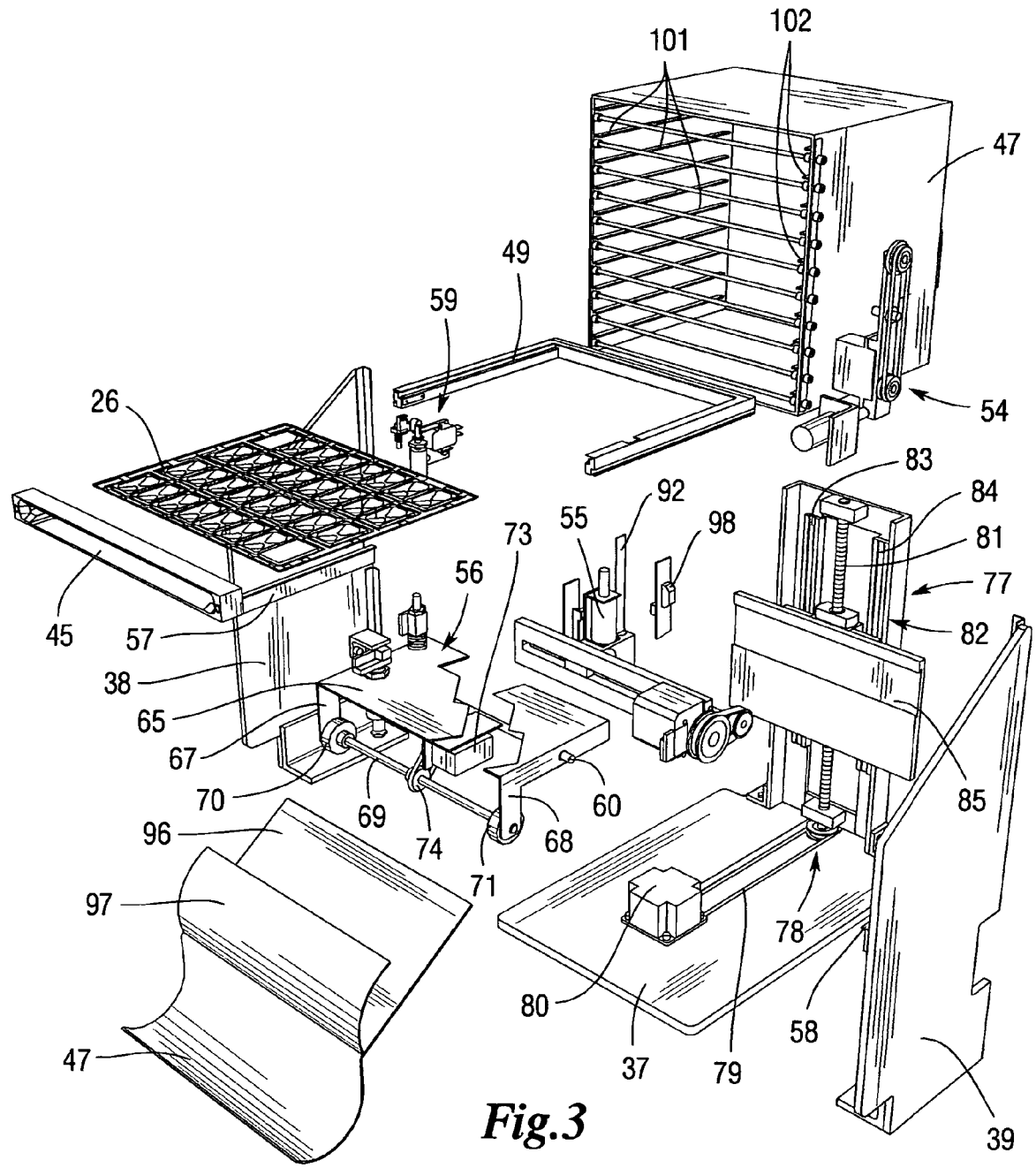
FIG. 3 is an assembly view of one example of a non-sequential medication delivery module in accordance with an embodiment of the invention.
Figure 4:
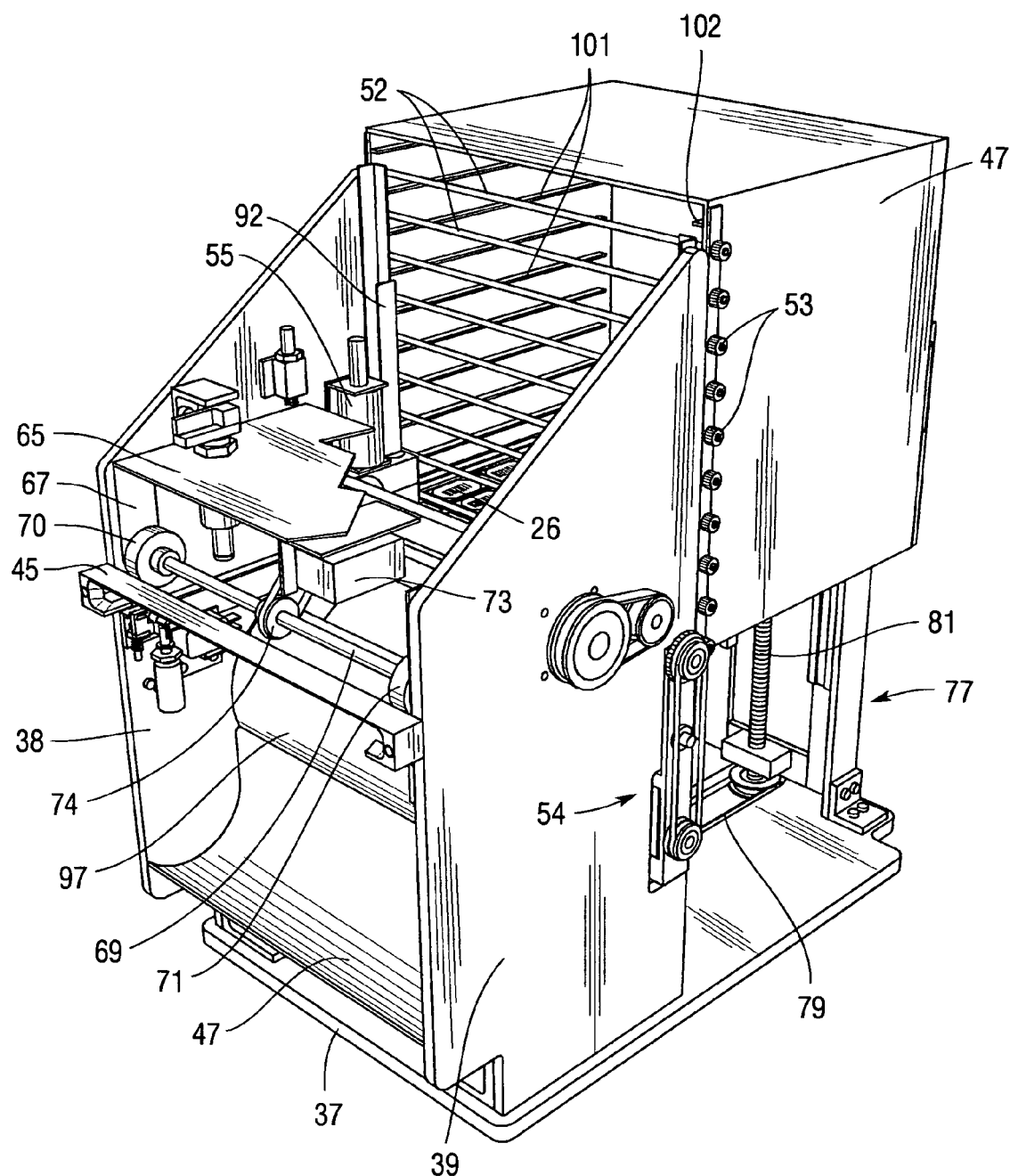
FIGS. 4 and 5 are cutaway views showing the friction drive assembly and storage elevator in accordance with one embodiment of the invention.
Figure 5:
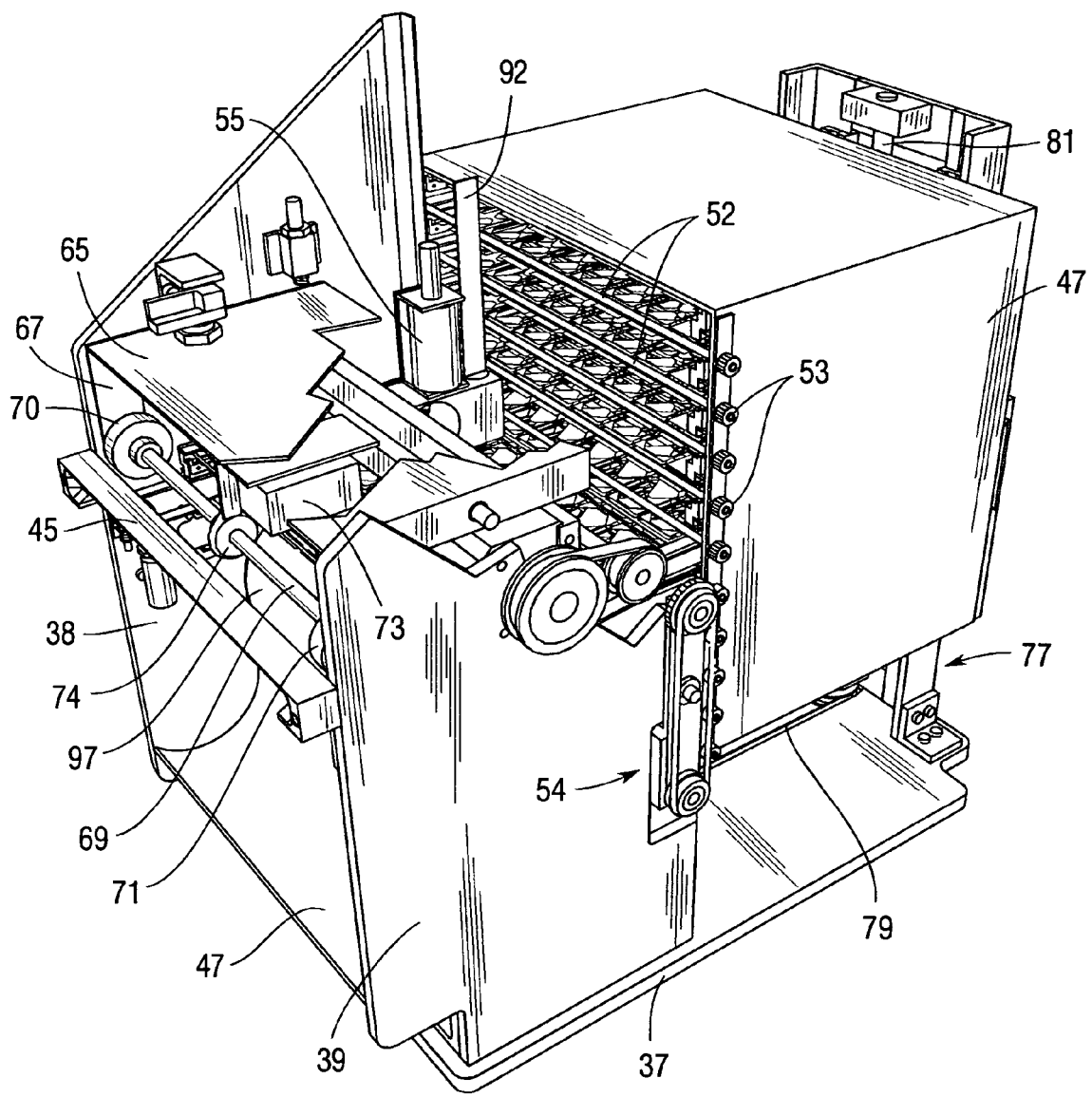
Figures 7A, 7B:
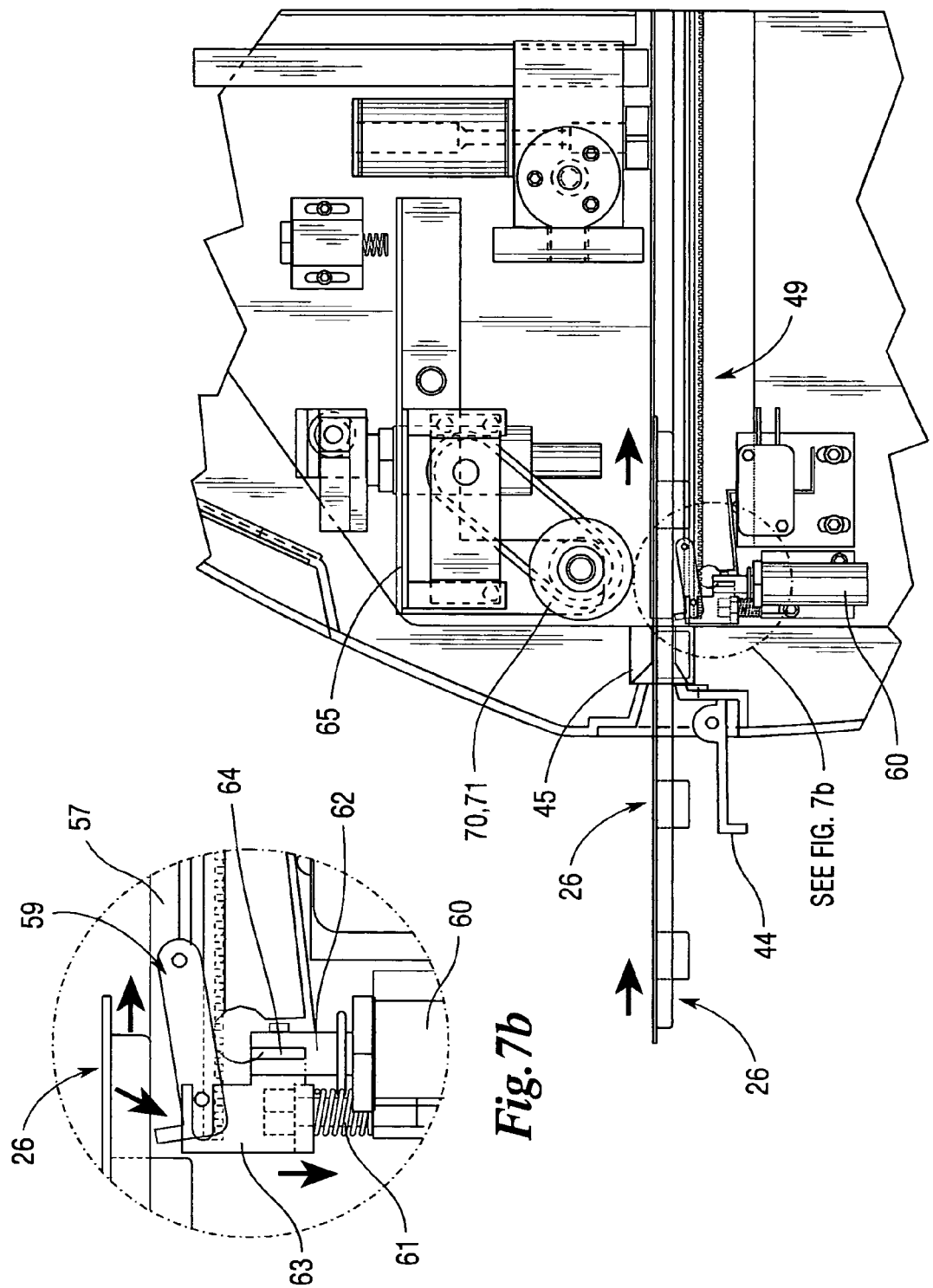
FIG. 7a is a cross-sectional view illustrating the mechanism of operation of the latch apparatus.
FIG. 7b is an exploded view of the latch apparatus in an unlocked position.
Figure 8:
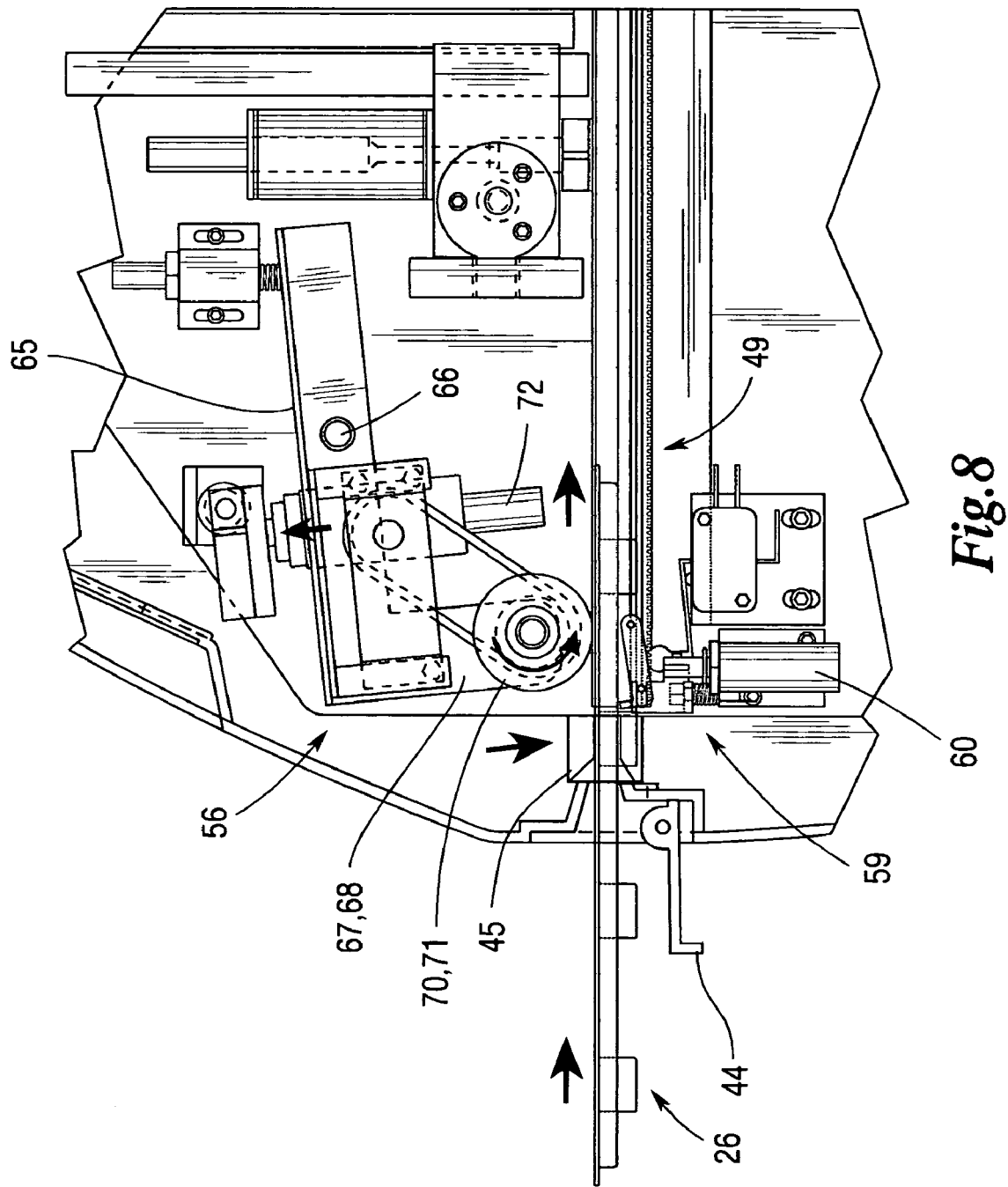
FIG. 8 is a cross-sectional view illustrating the mechanism of operation of the friction drive assembly with respect to an incoming medication carrier in accordance with an embodiment of the invention.
Figure 11:
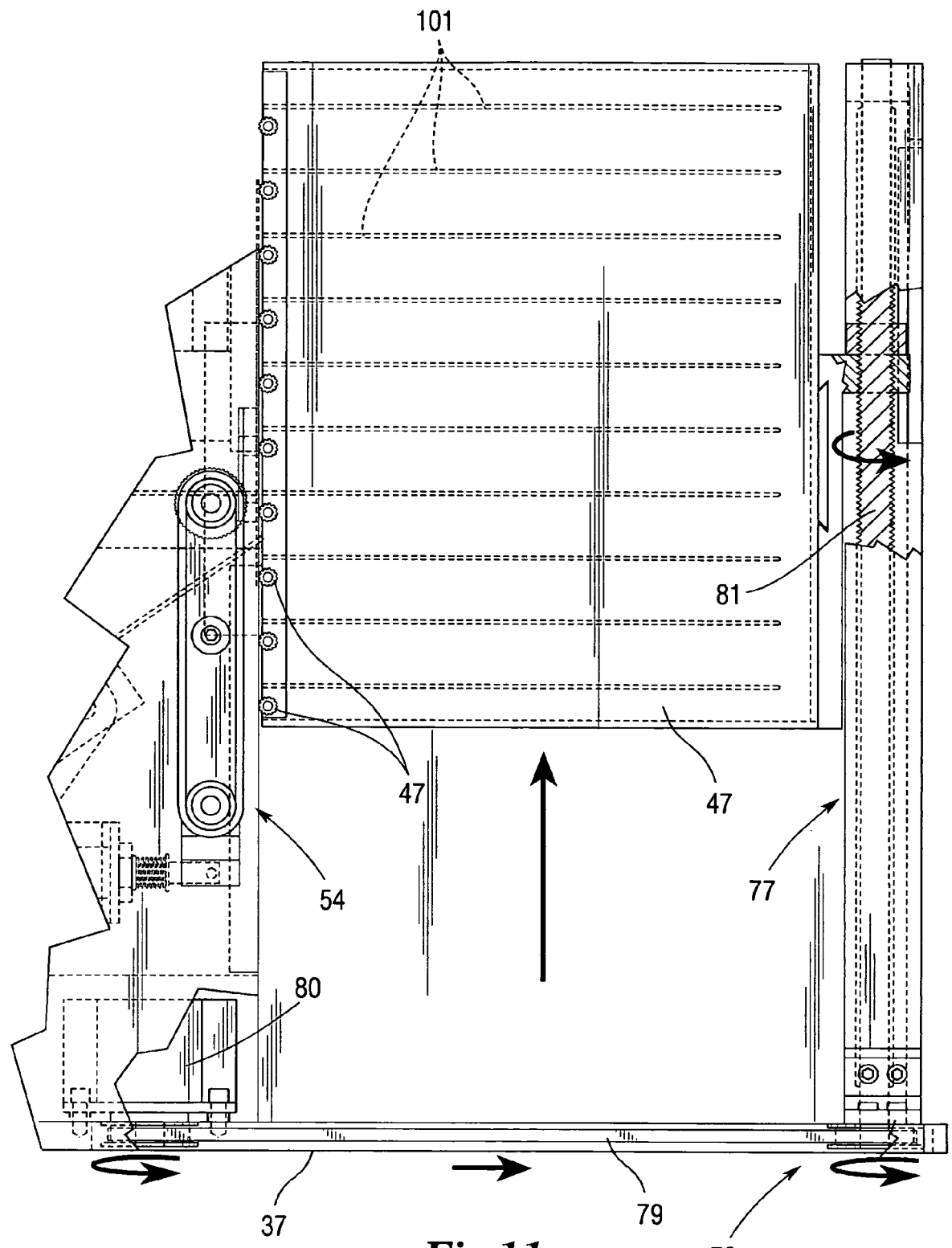
FIG. 11 is a cross-sectional view illustrating the operation of the storage elevator and associated linear motion assembly in accordance with an embodiment of the invention.
Figure 18:
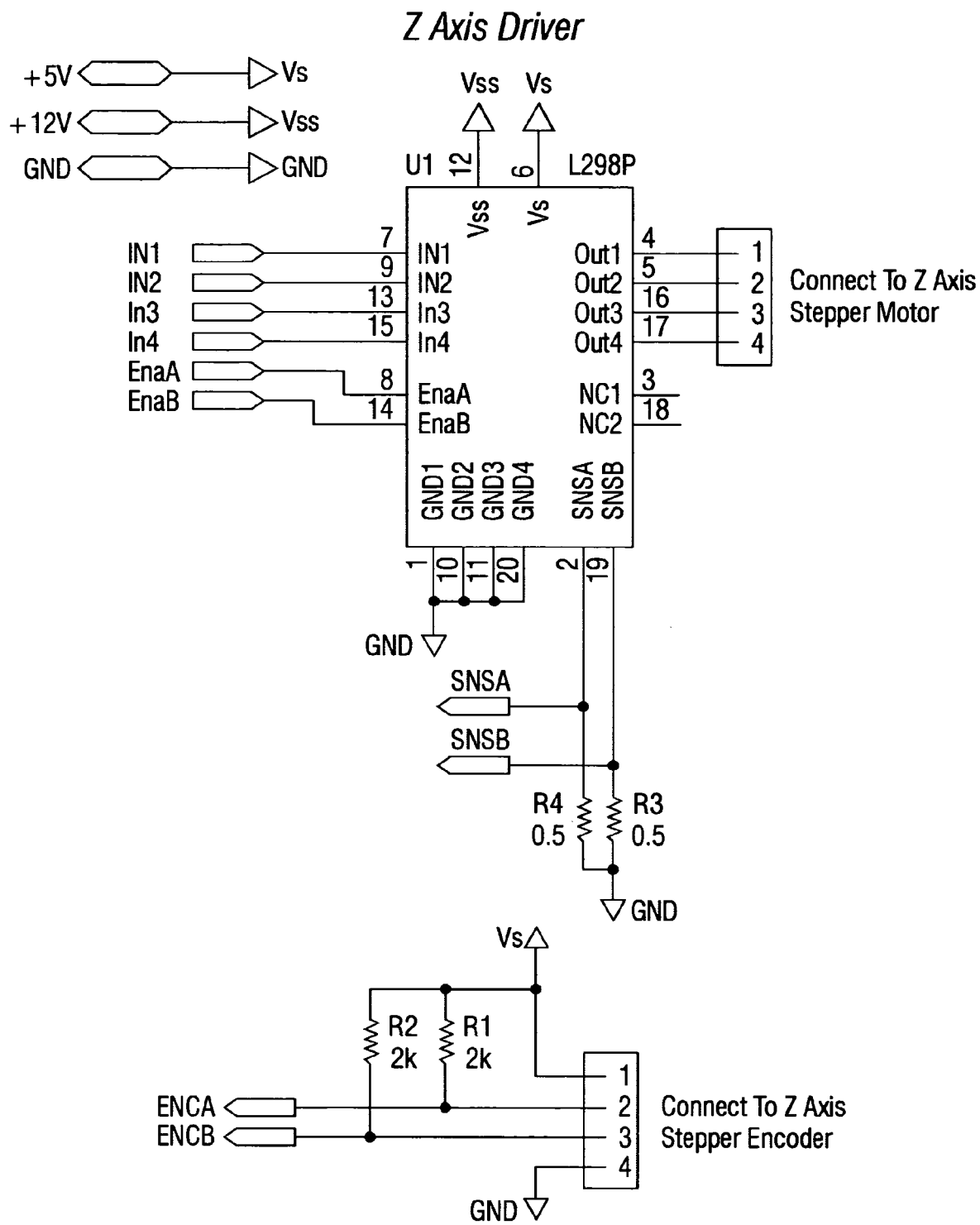
Figure 19:
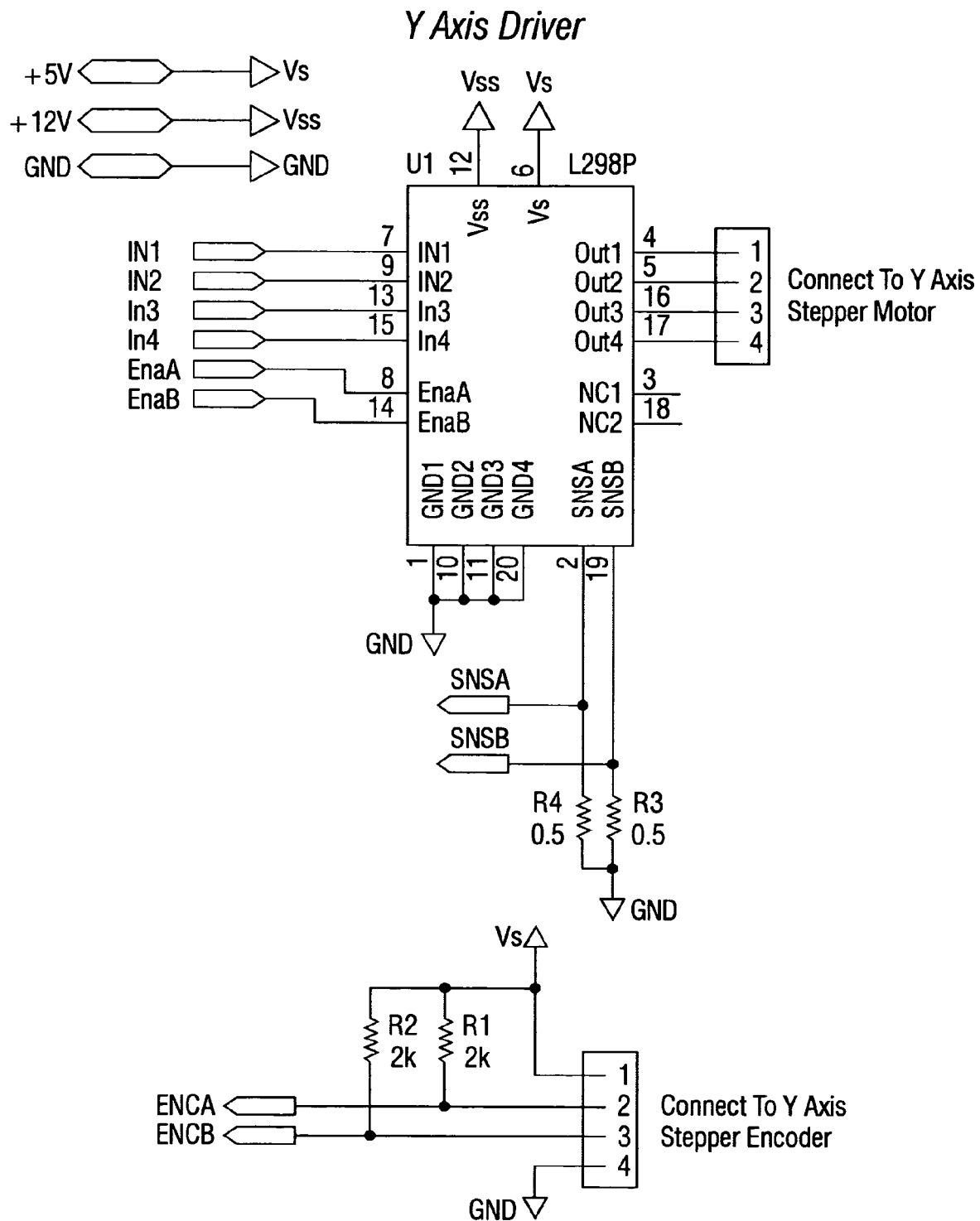
Figure 20:
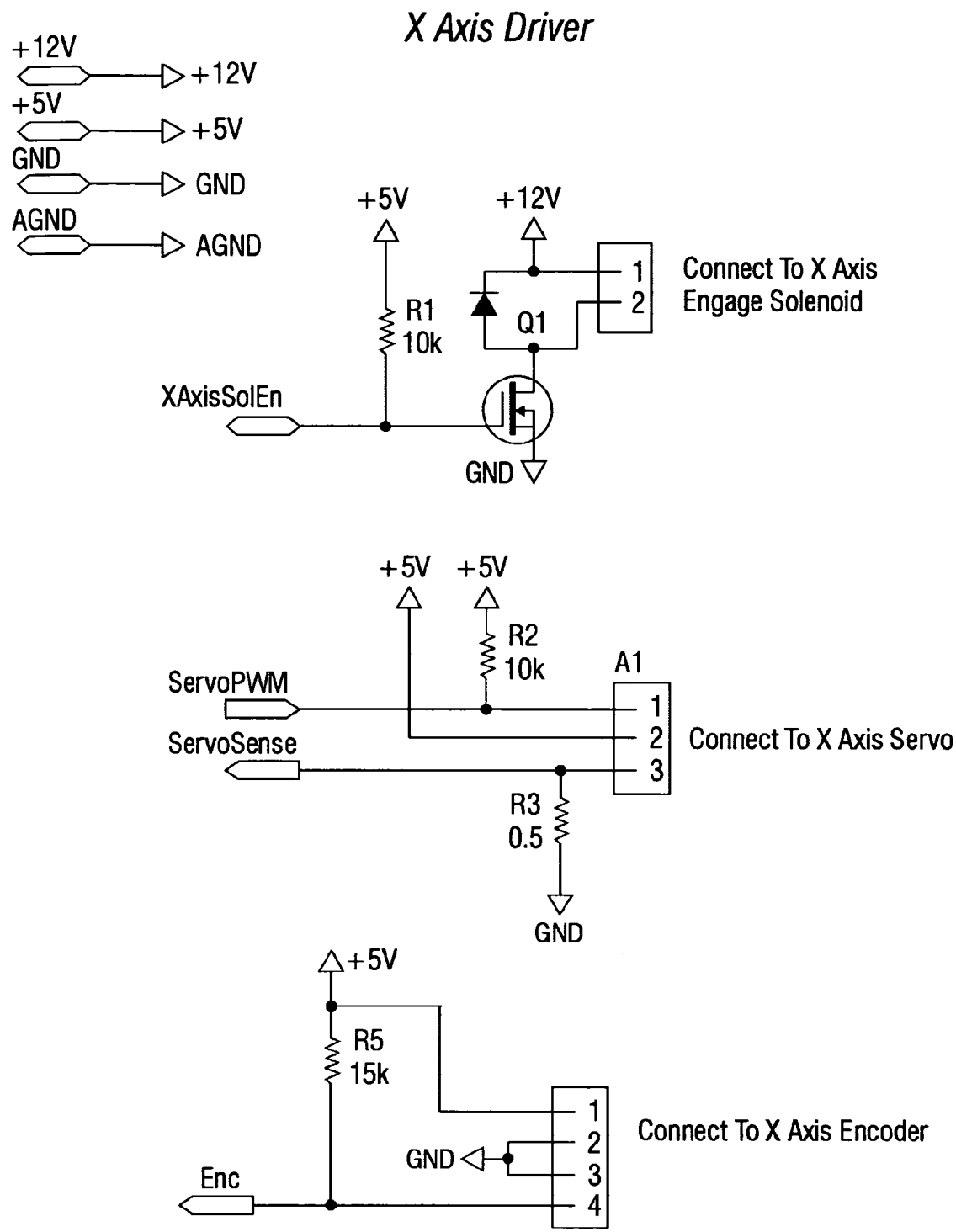

Referring now to FIGS. 3 and 11, the storage elevator 47 is operably connected to an elevator bracket 77 which moves the elevator 47 from a rest position, in the lower section of the housing, to an operative position, adjacent the delivery area, along a vertical ("z") axis. Vertical movement is achieved by means of a linear motion assembly 78 such as a gear belt and lead screw 81, pulley, or other standard drive component capable of converting rotary motion from a drive motor to linear motion. In the exemplary embodiment, a timing belt and lead screw 81 are rotated by a stepper motor 80 mounted to the base 37 of the housing. The motor 80 is actuated in accordance with electrical signals received from the controller (FIG. 18). The base 37 also accommodates the controller and a battery pack (not shown).

The elevator bracket 77 generally spans the length of the delivery module 33 so as to allow the storage elevator 47 to be raised and lowered to a desired level for accessing a medication carrier 26 stored within a particular storage bay 48. The elevator bracket 77 includes a channel housing 82 having a hollow portion in the center thereof and corresponding openings in upper and lower surfaces through which the lead screw 81 and one or more guide rods 83, 84 vertically extend. In general, the channel housing 82 serves as a frame for supporting the various components of the elevator bracket 77 and imparting stability to the guide rods 83, 84, or other suitable vertical shaft, such as, for example, an adjustable slide and block assembly. The channel housing 82 is vertically mounted to the base 37 of the delivery module 33, adjacent the rear panel 40, and is secured in place by bolts, casters or other suitable hardware.

Also featured in the hollow portion of the channel housing 82 are upper and lower cross members 102, 26, mounted in horizontal relation to the guide rods 83, 84 and lead screw 81, and interpolated by through holes in which the guide rods 83, 84 and lead screw 81, respectively, are slidably disposed. The cross members 102, 26 move along the perpendicular guide rods 83, 84 by operation of the motor 80 and lead screw assembly 81. This configuration permits a carrier plate 85 attached to the anterior surface of the cross members 102, 26 to be raised and lowered, in accordance with the direction of motion of the lead screw 81. The carrier plate 85 generally extends across the width of the housing and serves as a platform for attachment and support of the storage elevator 47. The storage elevator 47 includes a metal protrusion that projects outwardly from the rear wall of the elevator. The protrusion is suitably shaped to conform to a corresponding depression in the carrier plate 85 so that the carrier plate and storage elevator 47 can be conveniently and securely attached thereby.

The position of the storage elevator 47 within the housing is determined by means of an encoder located in the drive motor 80 which relays positional information to the controller in the form of electrical pulses as the motor 80 rotates (FIG. 11). Once the appropriate number of pulses is emitted by the encoder, signaling that the storage elevator 47 has attained the correct position for accessing a desired medication carrier 26, the controller disengages the motor 80. In this manner, the storage elevator 47 can be raised or lowered to an appropriate level within the housing.

Figure 12A:
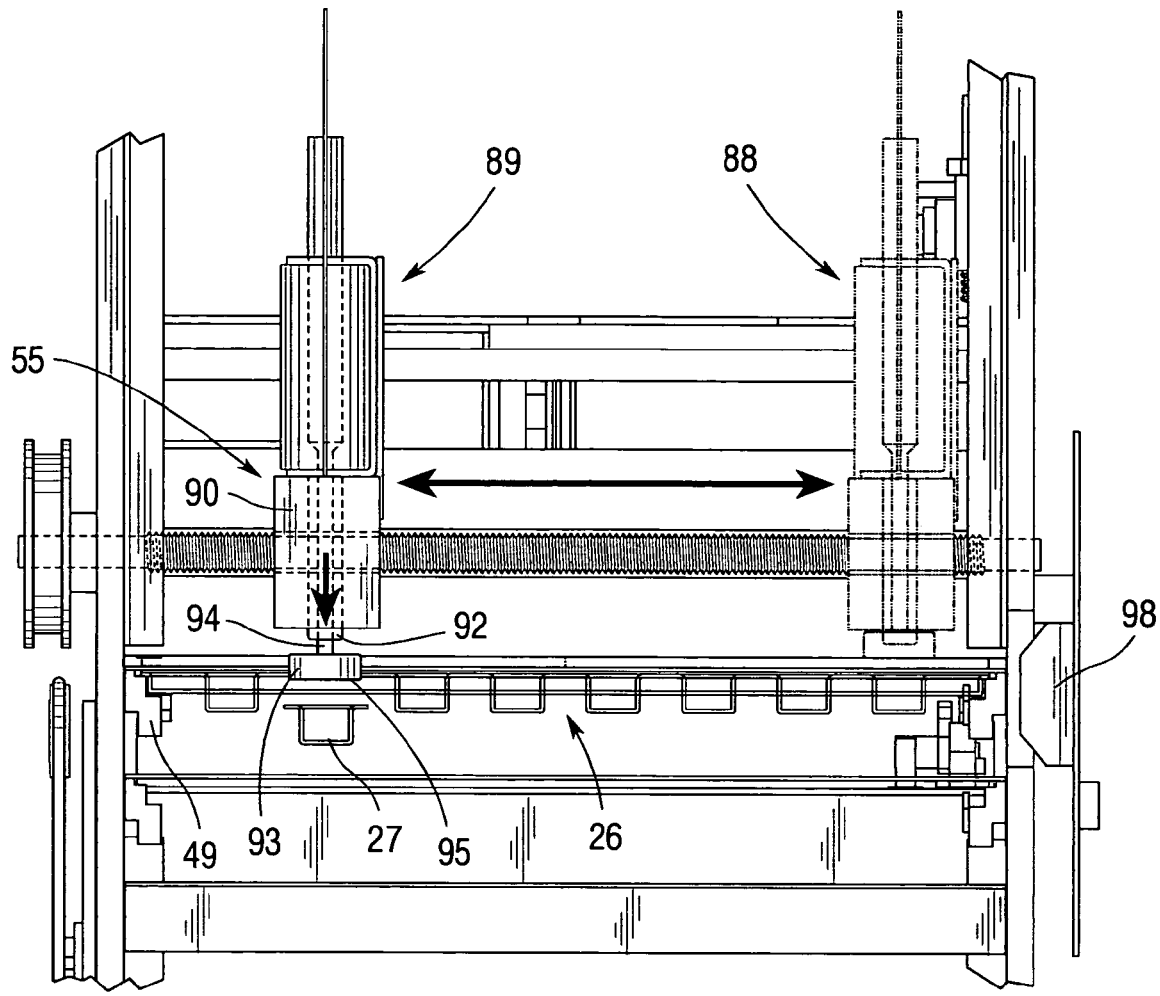
FIG. 12a is a cross-sectional view showing the ejector assembly in a rest position and operative position for ejecting a unit dose package from a medication carrier in accordance with one embodiment of the invention.
Figure 12B:
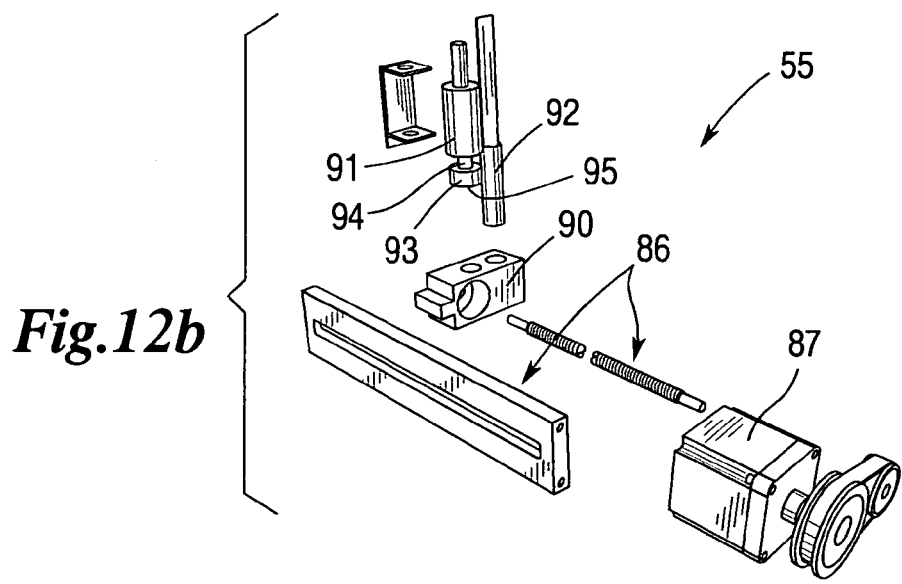
FIG. 12b is an assembly view of the ejector assembly shown in FIG. 12a in accordance with an embodiment of the invention.
Figure 13:
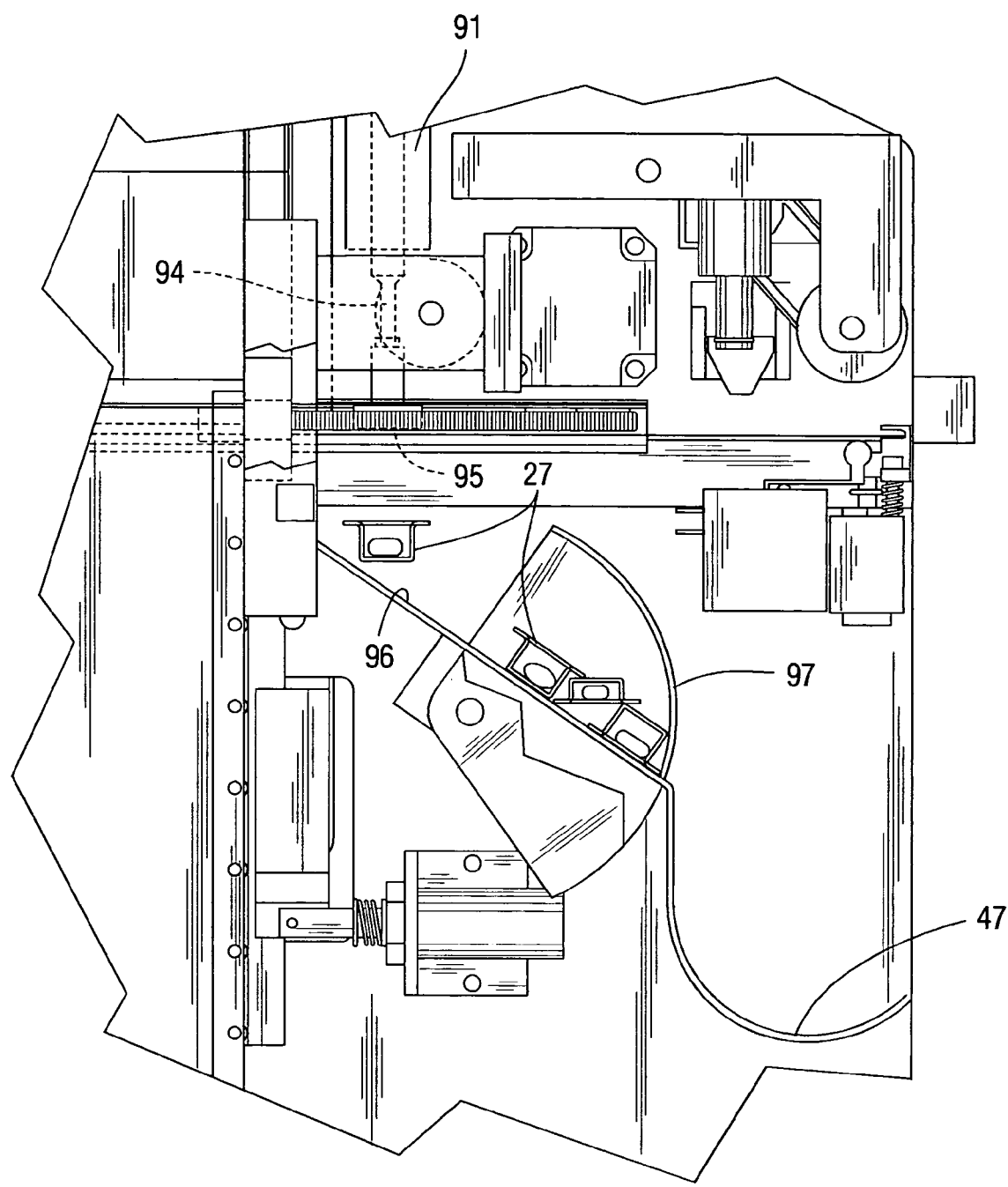
FIG. 13 is a cross-sectional view showing the ejected unit dose package of FIG. 12a along with previously ejected unit dose packages.

Referring now to FIG. 12, an ejector assembly 55 is provided for releasing a prescribed unit dose/unit-of-issue therapy 27 to a patient at a predetermined time, in accordance with a drop command originating from the clinical software 32. The ejector assembly 55 is mounted on and moves along a horizontal slide ("x-axis") 86 which extends across the width of the delivery module 33, between the storage elevator 47 and loading area. During dose delivery, the ejector assembly 55 is moved from a rest position 88 into an operative position 89 suitable for achieving contact with a desired unit dose package 27. Identification of the correct unit dose package 27 is determined by the control software 35, which correlates each instruction from a healthcare practitioner with a specific unit dose package 27. The ejector assembly 55 includes a sensor, electronic code scanner 92, electromechanical actuator 91, and a plunger 93, wherein each component is vertically positioned within and supported by a receptacle 90 that is slidably attached to the horizontal slide 86. The ejector assembly 55 is moved in the x-direction by means of a motor 87 operatively coupled to and under the control of the controller. The electromechanical drives on the ejector/reader (y-axis), elevator (z-axis), and carriage (x-axis) are specifically designed for non-slip reliability.

A sensor (not shown), such as an optical sensor, is located to sense the movement and alignment of the ejector assembly 55 as it is moved into an operative position 89 in proximity to the desired unit dose package 27. The sensor ensures that such operative position 89 corresponds to the designated position coordinates of the selected therapy. This is accomplished by means of a feedback loop arrangement with the controller.

An electronic code scanner 92, such as a bar code reader, optical recognition reader, radio frequency identification tag reader or other similar device, is operatively coupled to and suspended from a lower end of the actuator 91 so that the head of the scanner is positioned in proximity to upwardly facing electronic identifier codes 29, 31 imprinted on the medication carrier 26 and seal of the desired unit dose package 27. The scanner 92 detects removal of a unit dose package 27 from a stall 28 of the medication carrier 26, through interruption of a light beam emitted therefrom, and thereafter, transmits a signal to the controller confirming such removal. An electronic imaging device (e.g. a camera) may also be incorporated to provide visual feedback that the desired medication is suitably discharged from the medication carrier 26.

A plunger 93, having an elongated shaft 94, is mounted for vertical movement between raised and lowered positions by means of a linear actuator 91 attached to the shaft 94 thereof. The lowermost end of the shaft 94 terminates in a flat, compacting edge 95 which is suspended directly above the stall 28 of the medication carrier 26 containing the desired unit dose package 27. Upon receipt of a control signal, the actuator 91 forces the plunger 93 downward such that the plunger 93 achieves contact with the encoded surface of the unit dose package 27, pushing the package 27 through the opening of the stall 28.

A ramp 96 or chute is mounted to the side panels 38, 39 of the housing beneath the ejector assembly 55. The ramp 96 is generally a flat surface which extends across the width of the delivery module 33 and slopes downwardly so as to channel the ejected unit dose package 27 to a rotatable guard 97 located at the end of the ramp 96. The guard 97 is used for temporarily retaining an ejected unit dose package 27 until each of the medications within the patient's regimen is expelled. Once each of the prescribed medications is expelled, the guard 97 is rotated away from its initial position by a servo motor, releasing the ejected unit dose packages 27 into a receiving area 47 for collection by the patient.

The receiving area 47 is an open section configured in the front panel 41 of the housing where the medication is retrieved by a patient for consumption. Medication related information, such as the type, quantity and dosage of the discharged unit dose packages 27, appears on the electronic display 42. Alternatively, or in addition, a healthcare practitioner may communicate directly with the patient by providing instructions, additional information, or receiving feedback from the patient through the remote communication interface and display 42, keypad 43 or speaker.

Figure 23:
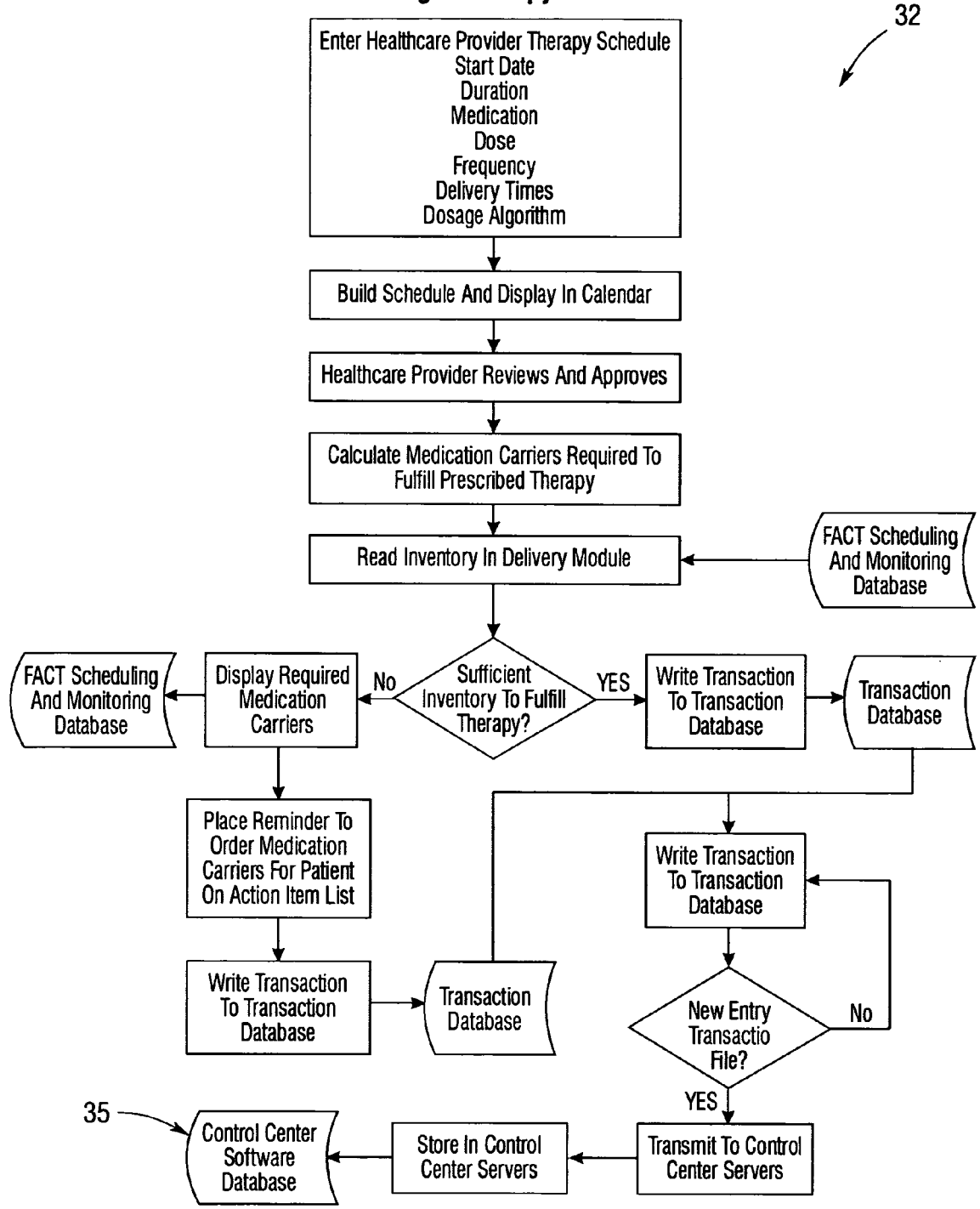
Figure 24A:
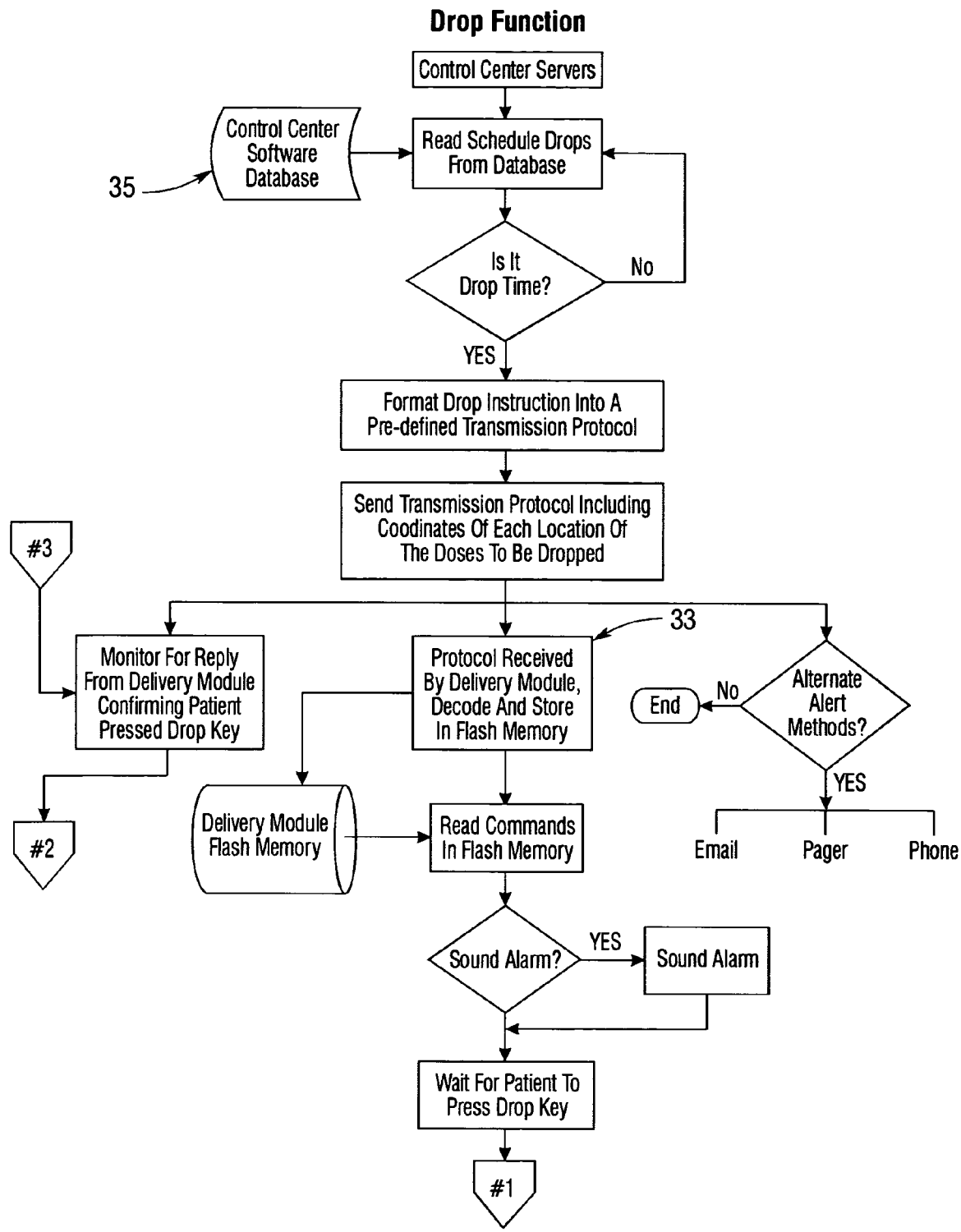
FIG. 24 is a flow chart illustrating the process that may take place to suitably deliver a prescribed dosage to a patient in accordance with an embodiment of the invention.
Figure 24B:
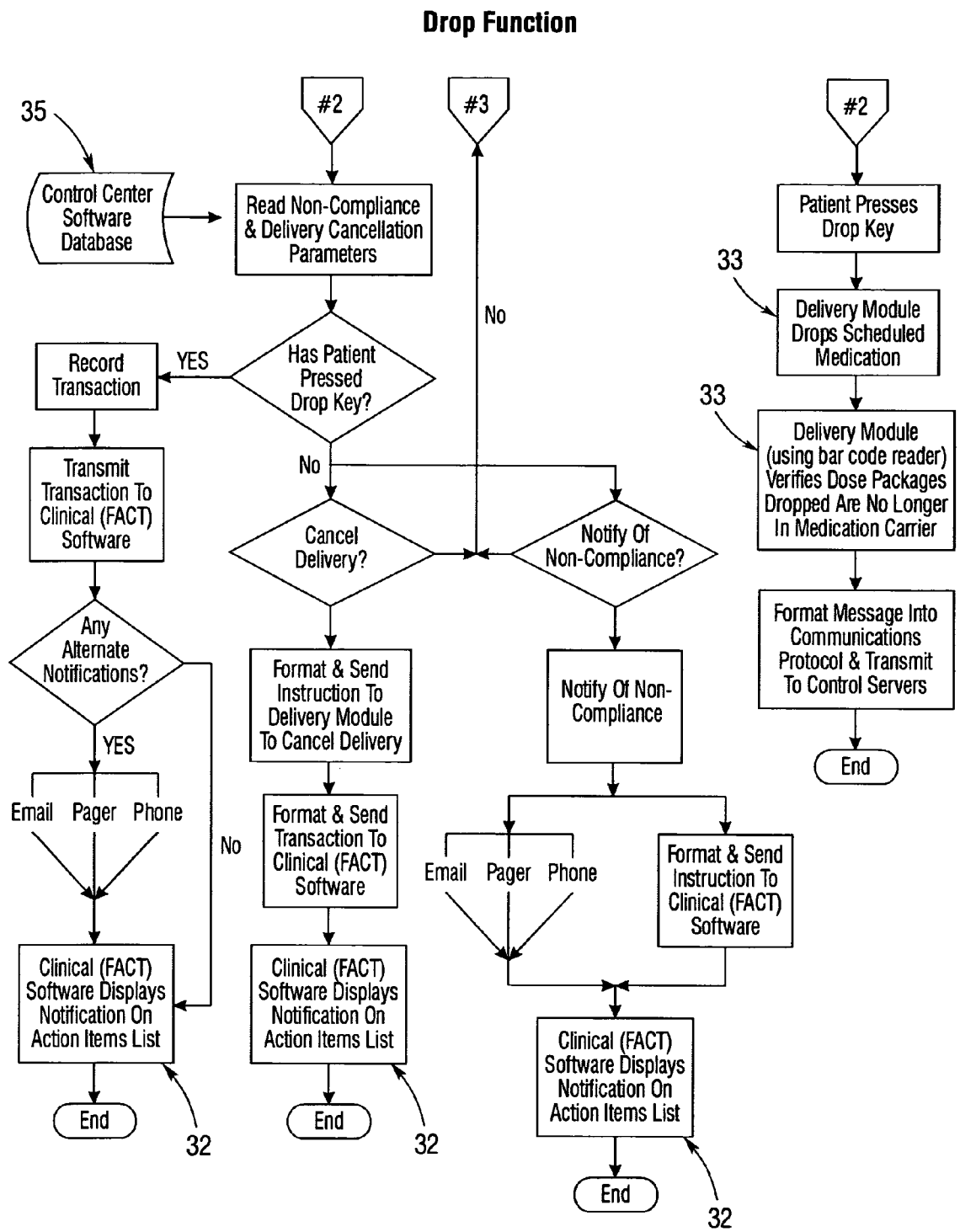

FIGS. 23 and 24 are flowcharts of the functional steps employed in the non-sequential delivery sequence of the present invention to deliver a desired therapeutic dosage to a patient as part of the same prescription period.

As mentioned above, a significant aspect of the instant invention is that it enables a physician, pharmacist, nurse or other healthcare practitioner remotely located from a patient to deliver any of the unit dose and unit-of-issue packages 27 stored within the delivery module 33 to the patient, in non-consecutive order, without being limited by a predetermined sequence. This unique delivery scheme allows the healthcare practitioner to instantaneously modify, queue, change, or discontinue a prescribed dosage in response to fluid medical conditions. Therefore, the precise location and contents of each unit dose package 27 contained within the delivery module 33 must be known at all times, both prior to and during the dose delivery process. The present system uses a feedback loop arrangement to manage this flow of data.

Figure 22:
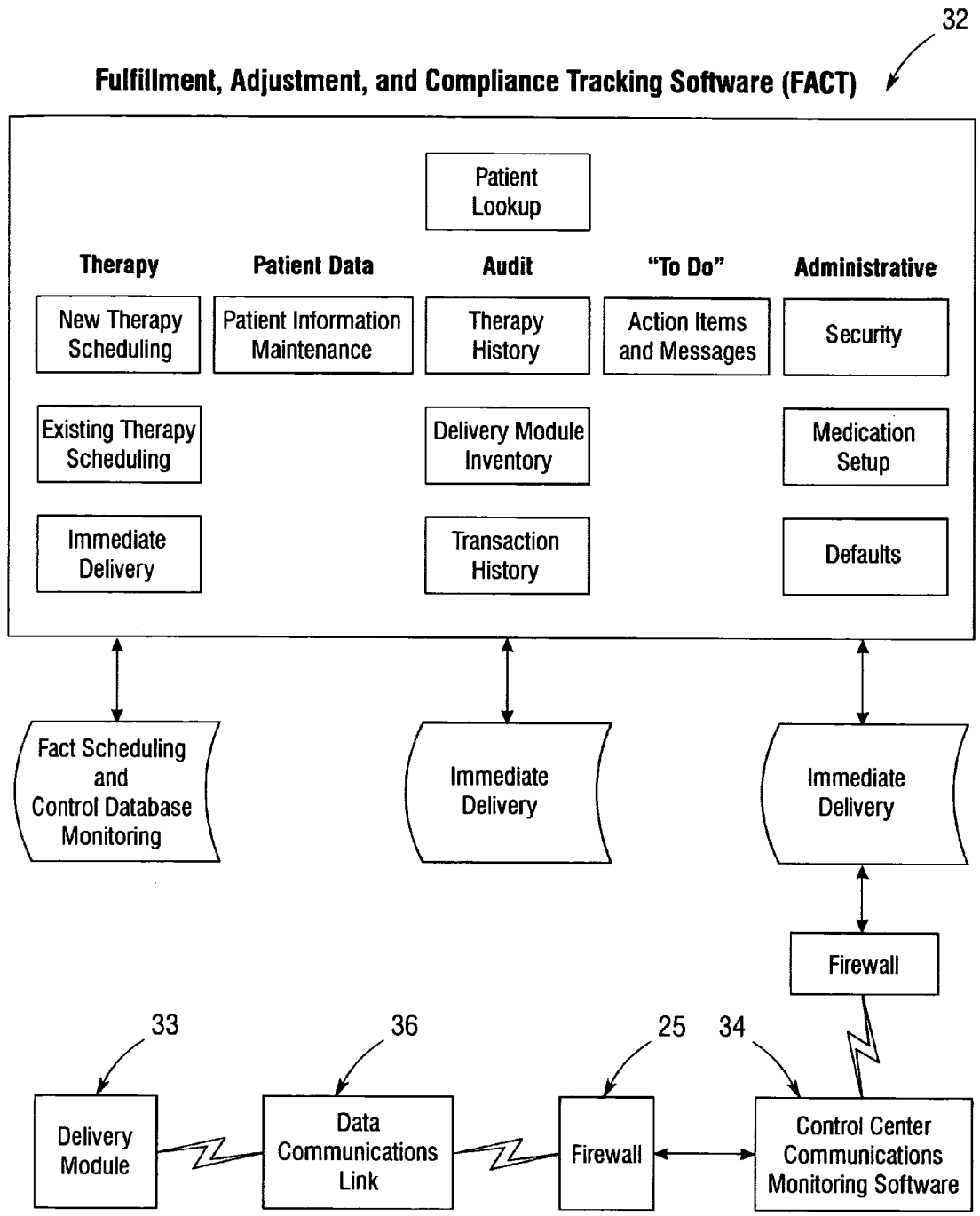
FIGS. 22-23 and 25-26 are flow charts illustrating the operations of the non-sequential medication delivery module and compliance system of the present invention.

In operation, a healthcare practitioner enters patient prescription information and dosage schedules using the Fulfillment, Adjustment and Compliance Tracking System (FACT™), or other clinical software application 32 (FIG. 22). Patient information is accessed by way of the software's user interface 100, which features a complement of menu-driven worksheets that appear on the practitioner's computer monitor. FIG. 29 is a worksheet showing a monthly therapy schedule for a patient, which is stored in memory. Other examples of worksheets which the health care provider uses to interact with the clinical software 32 are provided in FIGS. 27-28 and 30-31. All patient information, which includes, for example, prescription information, medication dosing schedules, dosage delivery criteria such as drug-drug interactions and food-drug interactions, and a history of dosage delivery results, is stored within the clinical software database 32. The clinical software database 32 utilizes the clinical facility's network security 34 policies and procedures to authenticate users and network access to patient information, in conformity with the Health Insurance Portability Accountability Act.

Just before a scheduled dosing time, the clinical software 32 transmits an encrypted signal to the control software 32 operating on a server located at the control center 101 to initiate delivery of a particular medication for a particular patient. The signal contains a command instruction set representing a prescribed medication regimen and dosing schedule for the patient, as well as a randomly generated Unit Identification Number (UIN) assigned to that patient's delivery module 33. Neither the patient's name nor any information identifying the patient are transmitted beyond the medical facility's firewall 34. Accordingly, only the clinical software 32 can correlate the prescribed regimen and dosing schedule, or delivery module 33, to the patient.

Following transmission, the signal is interpreted and authenticated by a control center 101 computer server. Utilizing the UIN, the server's control software 35 links each command instruction embedded within the signal to a specific delivery module 33. Next, the control software 35 utilizes a look up routine to correlate the instruction to a specific medication carrier 26 containing the desired unit dose package 27. This information, based on the encoded identifiers 29, 31 assigned to the medication carrier 26 and unit dose packages 27, is stored in the control software 35 database. The control software 35 ascertains the specific location within the delivery module 33 of the unit dose package 27 that is to be delivered to the patient in accordance with the programmed dosing schedule.

The control software 35 database specifies the vertical location (z-coordinate) of the medication carrier 26 as well as the row and column positions of the stall 28 containing such dose (y- and x-coordinates, respectively). In addition, the control software 35 database provides specific dose ejection parameters based on the internal configuration of the medication carrier 26 and the type of medication contained therein. This is accomplished using the stored electronic data which is communicated to the control center 101 computer server as the medication carriers 26 are loaded into the delivery module 33.

In the next step, the control software 35 reformats the signal into a proprietary protocol which includes a randomly generated communication's token and instructions for the delivery module 33 to drop the desired medication based on the x-, y- and z-coordinates of such medication. The instructions ensure that the correct medication, in an appropriate dosage form and amount, is delivered to the patient. The server transmits the reformatted signal to the controller located within the patient's delivery module 33 via radio frequency, or other suitable link. The controller interprets the command sent from the control center 101 server and sends confirmation thereto. This confirmation contains the communications token required for verification by the control server 101. In response, the control server 101 transmits a reconfirmation signal to the delivery module 33, authorizing the controller to drop the prescribed medication.

The module's 33 dose delivery sequence is activated upon receipt of the reconfirmation signal. The controller alerts the patient of the need to take the prescribed unit dose therapy 27 by way of the alarm, display 42 or other suitable visual, audible or other means. The controller concurrently establishes a window of time, relative to the alerting signal, during which the patient can input a delivery signal by, for example, depressing the drop key on the control panel 43. If the aural and visual signaling is ignored by the patient, the signaling will repeat every minute or more up to a programmed interval. The duration of the time window is set by the entered program or by a default value.

If the patient depresses the drop key 43 during the programmed time window, the controller, in cooperation with the drive motor 80, raises the storage elevator 47 to the correct vertical position (FIGS. 11 and 18) for accessing the storage bay 48 containing the unit dose package 27 to be delivered, in accordance with z-coordinate specified in the command instruction set. The position of the storage elevator 47 within the housing is determined by means of the motor-based encoder which relays positional information to the controller, in the form of electrical pulses, as the motor 80 rotates. Once the appropriate number of pulses is emitted, signaling that the storage elevator 47 has attained the correct position, the controller disengages the drive motor 80.

When the storage elevator 47 reaches the correct level for accessing the designated storage bay 48, the controller actuates the servo motor and pulley assembly 54 which controls horizontal movement in the y-direction (FIG. 19) so as to move a transport carriage 49 and integral medication carrier 26 housed within the storage bay 48 forward, away from the home position 99. An electronic code scanner 98 located within the storage elevator 47 reads location markers disposed along the outer edge of the carriage 49, which indicate the position of the carriage 49 and medication carrier 26 as they are advanced. This positional information is monitored by the controller through a feedback loop arrangement. Once the controller determines that an appropriate number of markers have been scanned, in accordance with the y-coordinate instruction received from the control server, the motor and pulley assembly 54 are disengaged. As the transport carriage 49 and carrier 26 are moved into proper position, the scanner 98 also reads an encoded identifier label 29 affixed to the upwardly oriented surface of the medication carrier 26, which contains the x-coordinate operational parameters.

At this point, the transport carriage 49 and medication carrier 26 have sufficiently cleared the opening of the storage elevator 47 such that the desired unit dose package 27 is positioned beneath the horizontal slide 86 of the ejector assembly 55. A control signal (FIGS. 16 and 20) is sent to the motor 87 responsible for movement about the x-axis so as to advance the slide-mounted receptacle 90 from a rest position 88 into an operative position 89 above the medication that is to be delivered. In this delivery ready position, the compacting edge 95 of the plunger 93 is suspended directly above the upwardly oriented, encoded 31 surface of the unit dose package 27.

In this orientation, the code scanner 92 suspended from the lower end of the actuator 91 is also positioned in proximity to the electronic identifier code 31 on the seal of the unit dose package 27. In instances where supplementary confirmation of delivery is desired, the scanner 92 reads the identifier code 31 and transmits verification to the controller that the selected dosage is the correct one, as a redundant check. The control software 35 layer links each command to a specific medication carrier 26 and unit dose package 27, the identification of which is scanned and verified at the time of loading the delivery module 33.

In the next step, a control signal is sent to the actuator 91 connected to the shaft 94 of the plunger 93. As this occurs, the shaft 94 is biased downward, whereby the compacting edge 95 contacts the encoded 31 surface of the unit dose package 27. This action causes the retaining means 30 of the affected stall 28 to release the unit dose package 27 contained therein. The ejected package 27 drops onto the ramp 96 situated beneath the ejector assembly 55, and thereafter slides into the rotatable guard 97 located at the bottom of the ramp 96. The guard 96 temporarily retains the ejected medication until each of the medications within the patient's regimen is expelled.

When the electronic code scanner 92 detects removal of the unit dose package 27, out of the medication carrier 26, a signal is sent to the controller, verifying that the prescribed dose is suitably removed from the carrier 26. In instances where visual identification is desirable, an electronic imaging device may be used to independently verify that the desired medication is suitably discharged from the carrier 26.

If additional unit dose packages 27 are scheduled to be expelled from the same medication carrier 26, e.g. in instances where multiple dosage strengths of the same medication are combined to obtain a correct dosage amount, the carrier 26 is again advanced in the y-direction, while the ejector assembly 55 is moved into the appropriate x-position. Once all of the prescribed medications have been ejected from the medication carrier 26, the transport carriage 49 and carrier 26 return to their home position 99 within the storage bay 48.

If a prescribed unit dose package 27 is contained in a different medication carrier 26, the storage elevator 47 is raised or lowered to the appropriate level, in accordance with the z-coordinate specified in the command instruction set. Thereafter, the transport carriage 49 and medication carrier 26 are moved forwardly, into the correct y-position, while the receptacle 90 of the ejector assembly 55 is moved in the x-direction. When the medication carrier 26 is in proper position, the plunger 93 pushes the dose 27 out of the carrier 26, causing the ejected dose 27 to fall onto the ramp 96. This sequence is repeated for each of the medications within the patient's regimen, in accordance with the instructions received from the control center 101 computer server. It should be understood that all of the medications for a particular dosage period are ejected in rapid succession, typically less than ten seconds per medication.

Once all the medications for the scheduled dosage time are expelled from their respective medication carriers 26, the controller activates the audible alarm, electronic display 42 or other suitable alert mechanism to notify the patient that medication is ready to be taken. Simultaneously, a control signal actuates the servo motor that is operatively coupled to the rotatable guard 97 at the base of the ramp 96. As the guard 97 rotates, the ejected, fully sealed unit dose packages 27 fall into the receiving area 47 for collection by the patient. At the same time, the electronic display 42 presents a description of the medical products placed into the receiving area 47, which may include, for example, the type, quantity and dosage of the delivered medical products.

In order to monitor compliance as well as maintain a complete audit trail of the patient's interaction with the delivery module 33, the module automatically transmits a signal to the control center 101 computer server, via radio frequency, or other communication link 36, once the dosage is discharged. The signal confirms that the prescribed dosage has been delivered to the patient within the scheduled dosing period. The transmission is date and time stamped in order to provide an accurate record of the transaction. The control software 35, which operates on the control center 101 server, receives and decodes the signal. Once the signal is authenticated, the control software 35 systematically updates the status of each unit dose package 27 delivered during the scheduled dosing period. The updated usage information is stored in the control software 35 database so as to provide precise inventory control and flawless delivery of the diverse medical products contained within the delivery module 33. The dosage administration transaction record is also stored in the control software 35 database, then formatted into an XML message stream and sent to the clinical software layer 32 in the succeeding polling cycle, using an encrypted Secure Socket Layer 25.

Every few minutes, the clinical software 32 checks for status updates sent to the clinical facility's data server. When the clinical software 32 receives the transaction record, the software 32 stores the information in the database which houses the patient's therapeutic regimen and dose delivery instructions entered by the healthcare practitioner. The transaction record provides, for example, an updated, complete inventory of the unit dose packages 27 contained within the patient's delivery module 33 as well as the date and time that the prescribed dosage was received by the patient. This information is directly provided to one or more computer stations 100 within the clinical facility, enabling an authorized healthcare practitioner to review the patient's dosage delivery results in real time. Once the dosage confirmation message is received from the control center server, signifying that the prescribed dosage has been delivered to a patient, the clinical software 32 initializes a routine to remove that particular dosage delivery event from the pending list.

If the patient fails to respond to the alarm generated by the delivery module 33 at a scheduled dosing time, e.g., by pressing the drop key 43 of the delivery module 33 at the end of the programmed time window, a routine is initialized which may include a call to the patient or a call to the patient's care provider, doctor, pharmacist or other designated individual. The delivery module 33 automatically transmits an alert to the control center 101 server, via radio frequency or other suitable communications link 36. Immediately thereafter, notification of the missed dosage is transmitted to the clinical facility's data server using the secure encryption method 25 as described above.

A further embodiment uses, for example, two time windows during which the patient may input the delivery signal, e.g., depress the drop key 43. In the first time window, the delivery module 33 generates an audible, visual or other alarm at a first intensity. If that first time window ends and the patient has not yet entered the delivery signal the module 33 increases the alarm level. The increased alarm level is continuous or, alternatively, steadily increases until the end of the second time window. Notification of the non-compliance action is transmitted to the control center 101 servers if the patient, at the end of the second time window, has still not responded to the alarm.

Delivery of the scheduled dosage does not occur unless the patient actuates the drop key 43 within the designated time interval. In this way, the present invention ensures that the patient receives the exact dose prescribed at the correct dosing time. This feature improves adherence and protects the patient from adverse drug interactions which may result from taking multiple doses of medication at unscheduled dosing times.

Patient dosage administration results are routed to and received by the clinical facility in real time. The clinical software 32 automatically alerts the healthcare practitioner of the non-compliance action by generating an alert message which is displayed on the practitioner's computer monitor (user interface 100). The practitioner can then take timely action by directly contacting the patient and/or directing an appropriate command back to the delivery module 33, or as otherwise described below.

After reviewing the notification of non-compliance, the patient's physician, pharmacist or other licensed healthcare practitioner retrieves and evaluates the patient's treatment regimen, which is stored within the clinical software 32 database and is accessed by way of the user interface 100. This information includes, but is not limited to, prescription information such as the name, type (brand or generic), potency strength and dosage form of a prescribed medical product, dosing schedules, dosage administration criteria such as drug-drug interactions and drug-food interactions, and the next pending dosage delivery event. The healthcare practitioner then determines whether the patient's medication regimen, dosing schedule, or both, should be modified to accommodate the missed dosage by, for example, entering an instruction that cancels, queues or modifies a prescribed dosage amount, using the appropriate worksheet 100.

This is accomplished, in part, through the use of electronic identifier codes 29, 31 which allow the precise location and contents of the prescription and non-prescription medications, pharmaceuticals, and nutraceuticals contained within a particular delivery module 33 to be known at all times, both prior to and during the dosage delivery process. This information is stored and monitored by the control center 101. A record of each dosing transaction, which includes an updated inventory of unused unit dose packages 27, is transmitted to the clinical facility immediately after each transaction occurs. The healthcare practitioner reviews the updated inventory listing which appears on his/her computer monitor (user interface 100). If an unscheduled dosage and/or schedule adjustment is deemed appropriate by the prescribing physician, the healthcare practitioner selects an alternate dosage or different medication from the list of prescribed therapies available to the patient and enters appropriate delivery criteria. The new dosage information is saved within the clinical software 32 database. The patient does not have to travel to a physician's office or to a pharmacy in order to obtain and fill a new prescription. There are no delays or interruptions in the continuity of treatment and compliance with the prescribed treatment regimen is addressed almost immediately.

In a similar fashion, the system of the present invention enables the healthcare practitioner to actively respond to an unexpected change in the health condition of a patient almost immediately. The invention is suited for situations where appropriate dosage amounts are evaluated on an ongoing basis, for example, through laboratory tests that change over time in accordance with the patient's needs. In these situations, the healthcare practitioner is able to remotely adjust the patient's dosage amount or deliver a different medication almost immediately, without the need for a new prescription. This is particularly important where narrow therapeutic index drugs are prescribed and over-medicating or under-medicating the patient can cause serious side effects and illness. The present system prevents the patient's condition from deteriorating since the patient is able to continue his/her course of treatment without potentially harmful interruptions.

Every few minutes, the clinical software 32 initializes a routine that monitors modifications to the database that houses the schedule and instructions entered by the healthcare practitioner. When the software 32 detects a dosage and/or schedule change, the information is conveyed to the URL of the control center 101 computer server using an encrypted Secure Socket Layer 36. As described previously, the information is formatted into an XML command instruction set that contains the Unit Internal Number (UIN) and other identifiers required for authentication by the control center 101 server. The control software 35 installed on the server authenticates and decodes instructions received from the clinical software 32. A reply signal is then sent to the clinical software 32, acknowledging receipt of such instructions. Utilizing the UIN, the control software 35 correlates the adjusted dosage delivery criteria to a particular delivery module 33. The control software 35 then references its database to determine the specific location, within the delivery module 33, of the unit dose package 27 that is to be delivered to the patient based on the then current inventory of unit dose packages 27 stored within the module 33. The delivery module 33 is able to expel the packages 27 non-sequentially, without being limited by a serial delivery restriction.

The control software 35 utilizes a look-up routine to retrieve the vertical location (z-coordinate) of the particular medication carrier 26 that contains the desired unit dose package 27, as well as the row and column positions of the stall 28 containing such dose (y- and x-coordinates, respectively). In addition, the look-up routine identifies specific dose ejection parameters based on the internal configuration of the medication carrier 26 and the type of medication contained therein. This is accomplished using the stored electronically coded identifiers 29, 31. The control software 35 simultaneously monitors the current time versus the scheduled drop time for the modified dosage. When the current time equals the scheduled drop time, the software 35 transmits a command signal to the delivery module 33 by means of radio frequency, or other suitable communications link 36. Included in the signal are instructions for the delivery module 33 to drop the modified dosage, based on the specified location coordinates.

When the command signal is received by the delivery module 33 to be activated, the module's controller decodes, verifies and loads the command signal into the controller execution queue by means of the logic program stored within the controller's memory. Immediately thereafter, the controller alerts the patient through visual, audible or other means, of the need to take the adjusted dosage. Once the patient responds to the alert generated by the delivery module 33, e.g., by articulating a prescribed verbal command or pressing the drop key 43 within the programmed time period, the dosage delivery sequence is initialized. Once the desired dosage has been delivered to the patient, confirmation and status information is sent to the control center 101 server. These results are immediately processed and conveyed to the clinical facility, enabling designated medical personnel to review the patient's dose delivery results in real time by way of the user interface 100. Hence, the feedback arrangement described herein permits the patient's medication regimen to be instantly adjusted and tailored to adapt to fluid medical conditions.

The healthcare practitioner can communicate with the patient at the time of dose delivery via telephone, email or by entering an appropriate command into his/her computer terminal. The command signal is processed by the control software 35 and thereafter transmitted to the patient's delivery module 33. Through this remote interface, which includes, for example, a keypad and/or speaker, the patient can be prompted to provide information or respond to questions.

While conventional pharmaceutical delivery systems provide a healthcare practitioner with data regarding a patient's health status, the present system allows a healthcare practitioner to actively respond to a change in a patient's health condition from a remote location. Each of the unit dose packages 27 contained within the delivery module 33 is separately encoded 31 and inventoried so as to be independently accessible and traceable. This allows the healthcare practitioner to deliver medication in non-consecutive order, on a dose by dose basis, and in a controlled and auditable fashion. In this manner, patient compliance with a prescribed regimen is precisely monitored. Moreover, dosage adjustments and other treatment decisions are made within parameters specified by a doctor in real time, simultaneous with the receipt of a communication regarding a change in a patient's health condition. This feature is particularly important given the overall increase in telehealth and telepharmacy based services.

As discussed above, the delivery module 33 of the exemplary embodiment can accommodate a plurality of medication carriers 26, each containing diverse therapeutic agents. For purposes of illustration, therefore, a typical carrier 26 loading operation is described below (FIGS. 7-10, 17 and 25a).

Loading of an empty or partially empty delivery module 33 is typically initiated by a patient, caregiver, or other authorized operator when a new supply of medication carriers 26 is received. The user simply depresses a load key 43 located on the front panel 41 of the housing, prompting the controller to transmit a load verification request to the control center 101 via radio frequency or other suitable transmission method 36. Once received by the control center 101, the load request signal is authenticated by the control software 35 and in most cases is accepted. The load verification request is denied in instances where a security password or other authorization is required to initiate the load operation, but is not entered by the operator.

In an alternative embodiment, the load operation is initialized by the control software 35. The control center 101 server transmits an encrypted load instruction, containing a randomly generated communications token, to the delivery module 33. Upon receipt thereof, the signal is decoded and verified for authenticity by the module's controller. If authentic, the controller sends a reply signal to the server, confirming receipt of the load instruction. Thereafter, the delivery module 33 generates an audible, visual or other alert in order to prompt the patient, or other operator, to depress the load key 43.

Once the operator activates the load key 43, the storage elevator 47 is immediately raised from its rest position in the lower section of the housing to a position operative for loading of a new medication carrier 26 into a storage bay 48. Movement of the storage elevator 47 to the appropriate level within the housing occurs by operation of the motor 80 and lead screw 81 assembly, through controller actuation. The storage elevator 47 is raised to a height at which the storage bay 48 to be loaded generally abuts the horizontal guide rails 57, 58 that extend along the side panels 38, 39 of the housing. In this position, the lower surface of the transport carriage 49 is situated slightly above the guide rails 57, 58 so that upon exiting the storage bay 48, the carriage 49 automatically rests against the guide rails. As discussed above, the storage elevator 47 is automatically moved to a correct position through operation of the encoder.

When the storage elevator 47 is properly positioned, the actuator 60 lowers the latch apparatus 59 to its unobtrusive position below the guide rail 57 so that the loading pathway is clear. The transport carriage 49 is advanced forwardly from its home position 99 within the storage bay 48 to a point at which the carriage 49 extends into the loading area of the housing. As the carriage 49 enters the loading area, its movement is detected by a sensor which relays positional information to the controller. A control signal is sent to the swivel bracket mounted actuator 72, wherein the actuator 72 distends downward so as to achieve contact with the upper surface of the carriage 49. Simultaneous therewith, the swivel bracket 65 pivots downwardly, causing the drive wheels 70, 71 to be lowered onto the upper surface of the carriage 49. The drive wheels 70, 71, through operation of the motor 73 and pulley assembly 74, rotate outwardly so as to move the carriage 49 along the guide rails 57, 58 in a further frontward direction.

When the front edges of the transport carriage 49 come into contact with the front panel 41 of the housing so as to be flush therewith, i.e. the prime position, the controller temporarily disengages the motor 73 so that frontward movement of the carriage 49 ceases. The distended actuator 72 moves upward to its original, raised position, simultaneously causing the swivel bracket 65 and drive wheels 70, 71 to pivot upwardly so as to release contact with the carriage 49. In this position, the carriage 26 abuts the insertion/retrieval slot 45 configured in the front panel 41 of the housing. The transport carriage 49 is now in position to receive an incoming medication carrier 26. Because the delivery module 33 is capable of accessing and delivering the patient's dosages in random sequence, the medication carriers 26 need not be loaded into the delivery module 33 in any particular order. This overcomes a significant drawback associated with prior art devices in that medication must be loaded in the order in which it is to be delivered.

At this point, the operator is prompted through audible, visual or other means, to open the handle equipped loading door 44 in order to insert a new medication carrier 26 into the insertion/retrieval slot 45, preferably with the medications facing downward. The controller determines whether a medication carrier 26 has been placed in the slot 45 by monitoring the sensor. When the sensor detects that a medication carrier 26 has been fully inserted, i.e. that peripheral edges of the medication carrier 26 extend sufficiently into the loading area (e.g. three inches or other predetermined distance) so as to activate a limit switch, the controller signals the drive wheels 70, 71 to distend and rotate in a reverse, or inward, direction and correspondingly advance the medication carrier 26 through the insertion/retrieval slot 45, into the awaiting carriage 49.

When the sensor detects that the medication carrier 26 is fully entrenched in the carriage 49, the actuator 60 causes the latch apparatus 59 to resume its original, indexed position above the guide rail 57 so as to secure the carriage 49 in place on the guide rails 57, 58 for transport by the drive wheels 70, 71. As the medication carrier 26 and carriage 49 move rearward, toward the empty storage bay 48, an electronic scanner 98 located in proximity to the medication carrier 26 is actuated in response to a control signal. The scanner 98 reads the encoded identifier 29 label attached to the upwardly oriented surface of the medication carrier 26, which identifies the carrier's serial number. The scanner 98 also records the specific storage bay 48 in which the medication carrier 26 is to be stored. Immediately thereafter, the scanner 98 retrieved information is communicated to the computers servers housed at the control center 101.

Once the medication carrier 26 and transport carriage 49 approach the opening to the storage bay 48, the motor and pulley assembly 54 causes the spur gears 53 mounted about the opening of the storage bay 48 to rotate, effecting rearward movement of the carriage 49 into the home position 99. The motor 73 attached to the swivel bracket 65 is then disengaged so that the drive wheels 70, 71 stop rotating. When this occurs, the distended actuator 72, moves upward to its original, raised position, simultaneously causing the swivel bracket 65 to pivot upwardly so as to be locked into its initial position.

Almost immediately thereafter, the storage elevator 47 is raised or lowered to a different position, i.e. level, operative for loading a second medication carrier 26. At this point, the operator is prompted to insert another medication carrier 26 into the insertion/retrieval slot 45. Each new carrier 26 is loaded in similar fashion, with the carriage 49 being advanced to receive and transport an incoming carrier 26 to the storage elevator 47, until all the medication carriers 26 are present in the delivery module 33. The operator is then alerted through audible, visual or other means, that the loading operation is complete. The entire process occurs very rapidly, generally within three minutes.

As described above, an electronic scanner 98 such as a bar code reader, optical recognition reader or radio frequency identification tag reader scans the electronic identifier codes 29 imprinted on the exposed surface of each medication carrier 26 as the carrier advances toward the storage elevator 47, and images the specific location of the carrier 26 therein. This information is provided to the control center 101 computer servers for later retrieval. Once the loading operation is complete, each of the scanned medication carriers 26 is temporarily removed from its storage bay 48, in turn. The scanner 98 locates and reads the electronic identifier codes 31 imprinted on the seal of each unit dose package 27 within the carrier 26 and images the specific storage bay 47 in which the unit dose package 27 is stored. The controller then transmits the scanner retrieved information to the control center 101, where it is correlated with the encoded data previously entered into the control software 35 database. In this manner, the precise location and contents of each unit dose and unit-of-issue package 27 contained within a particular delivery module 33 are stored within the control software layer 35 such that each dose 27 can be accurately tracked from the time of manufacture to the time of delivery to a patient. This stored data enables a healthcare practitioner to remotely select and deliver an appropriate therapy to a patient, as described above.

Figure 25A:
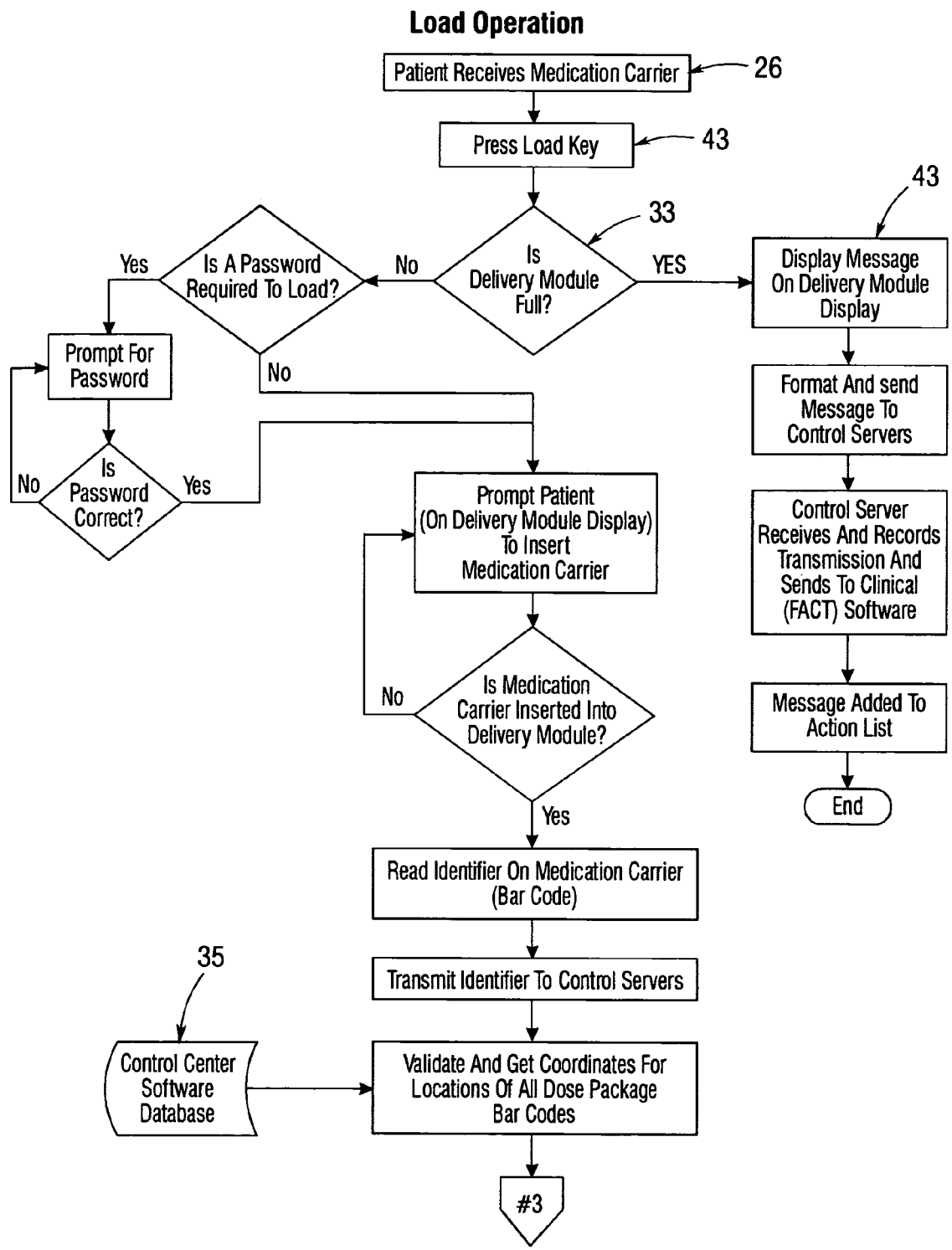
Figure 25B:
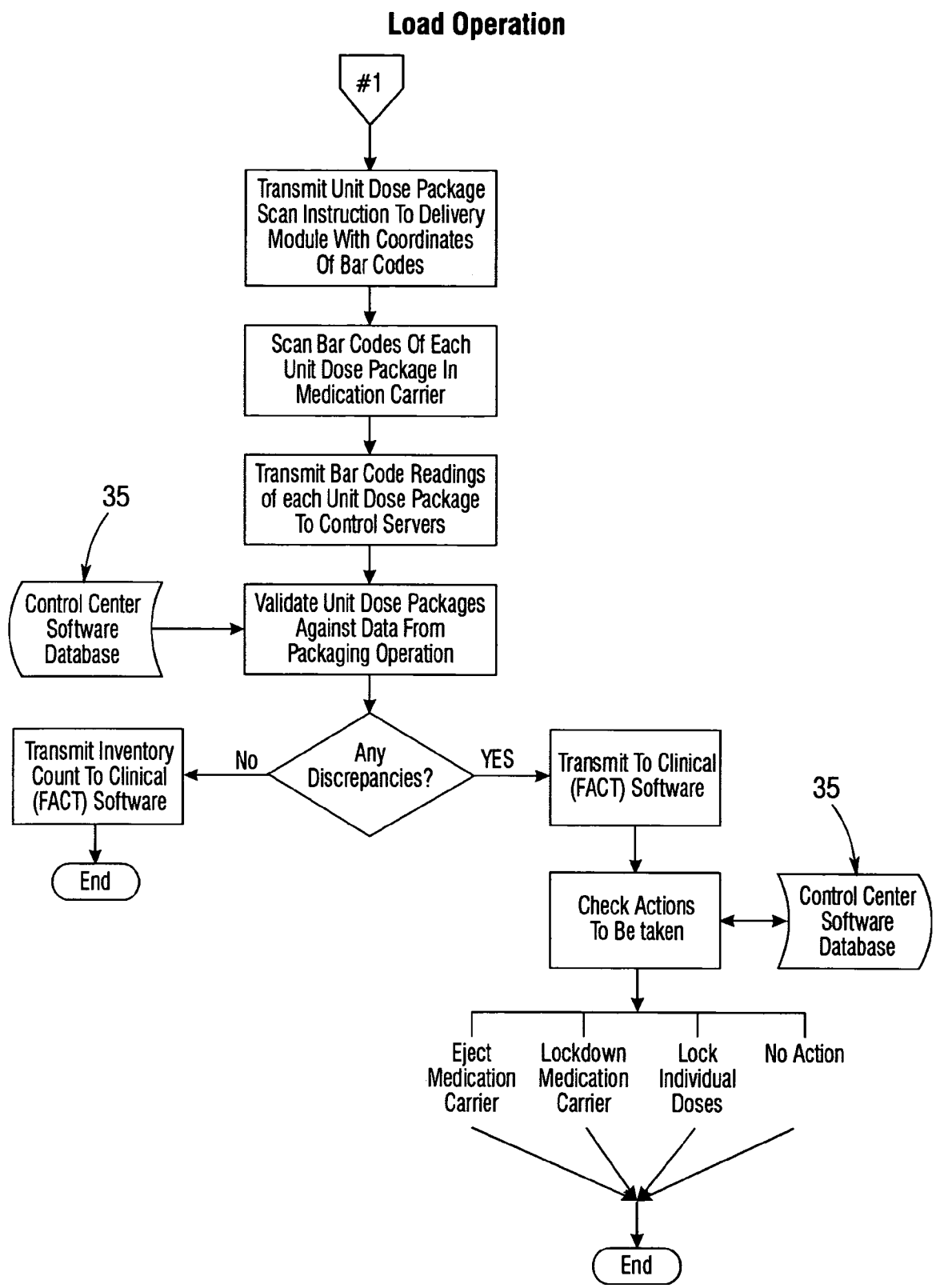
Figure 25C:
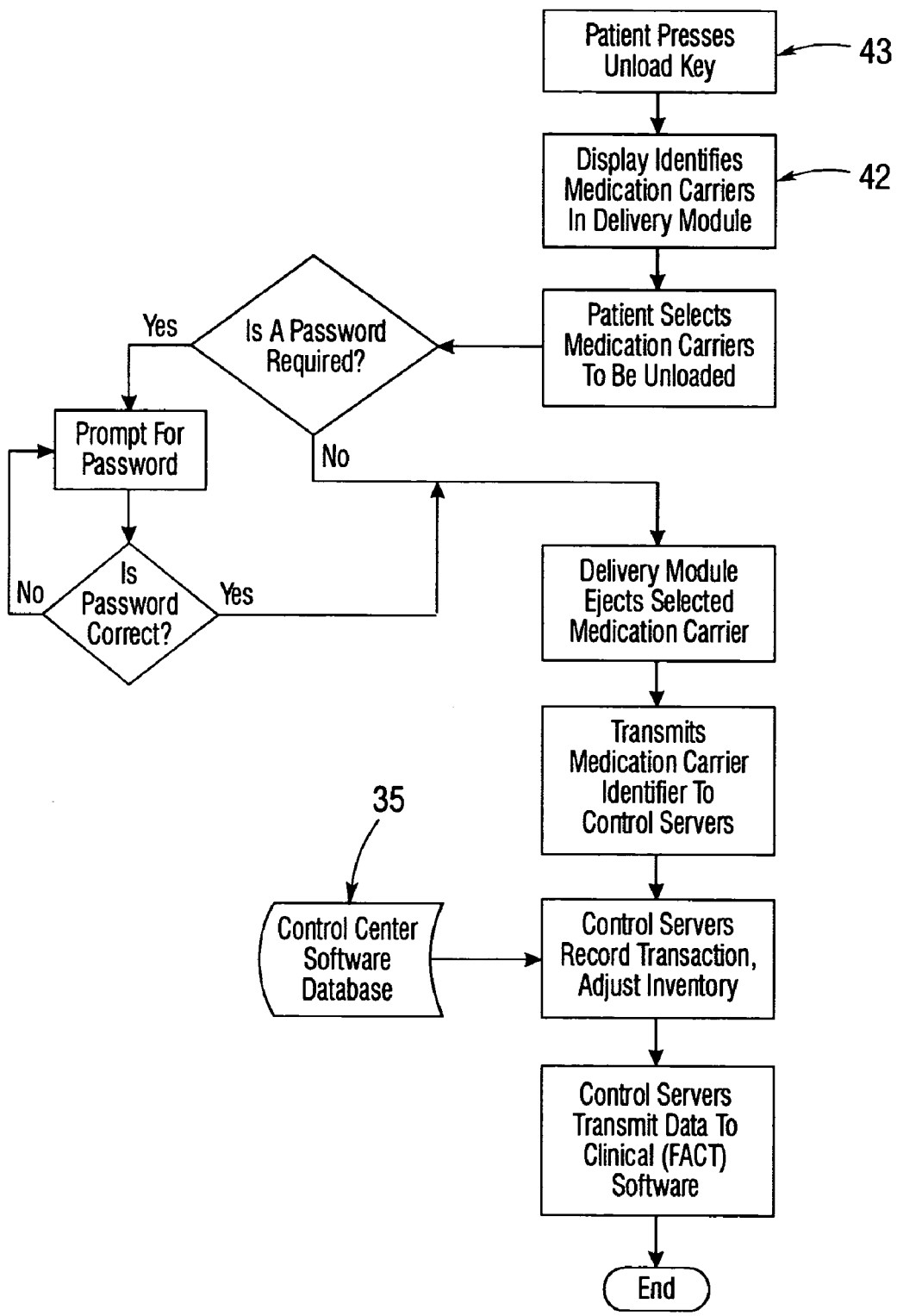

FIG. 25b illustrates a typical unloading operation. Medication carriers 26 are typically unloaded by a patient, caregiver, or other authorized operator when the patient's supply of medication is depleted. The operator simply presses the "unload" key 43 located on the front panel 41 of the housing, prompting the controller to transmit a verification request signal to the control center 101 server. Once received by the server, the signal is authenticated 25 by the control software 35 and thereafter authorized, once the control center 101 database verifies that a preselected number of stalls 28 of one or more medication carriers 26 is empty. Information necessary for verification of the request is stored in the server database, which maintains a continuously updated record of the location and status of each unit dose package 27 within the delivery module 33 through the use of electronically coded identifiers 29, 31. In this manner, the control center 101 is able to account for each unit dose package 27 at all times.

In an alternative embodiment, the unload operation originates from the control software layer 35. The control center 101 server transmits an encrypted 25 unload instruction to the delivery module 33 when the patient's medication supply falls below a predetermined level, as reflected by the server database. The signal is decoded and verified for authenticity by the delivery module 33 controller. If authentic, the controller sends a reply signal to the server, confirming receipt of the unload instruction. Thereafter, the delivery module 33 generates an audible, visual or other alert in order to prompt the patient, or other operator, to depress the unload key 43.

Once the operator activates the unload key 43, the storage elevator 47 is immediately raised from its rest position to a position operative for removal of a depleted medication carrier 26 from a storage bay 48. Thereafter, the transport carriage 49 and medication carrier 26 are ushered into the loading area of the housing in the manner described above. When the front edges of the carriage 49 come into contact with the front panel 41 of the housing so as to be flush therewith, i.e. the prime position, frontward movement of the carriage 49 ceases. The drive rollers 70, 71, however, continue to rotate outwardly, moving the depleted medication carrier 26 out of the carriage 49 and into the insertion/retrieval slot 45. A sensor is located to monitor movement of the outgoing medication carrier 26 through the insertion/retrieval slot 45.

Once the front edges of the medication carrier 26 have cleared the front panel 41 of the housing so as to protrude approximately three inches (or other distance suitable for manual retrieval of the carrier 26 by an operator), the controller briefly disengages the motor 73, preventing further rotation of the drive wheels 70, 71. The depleted medication carrier 26 is now in position to be removed by the operator. At this point, the operator is prompted, through audio, visual or other means, to open the handle equipped loading door 44 in order to retrieve the medication carrier 26 from the insertion/retrieval slot 45.

When the sensor detects that the depleted medication carrier 26 has been removed, the controller signals the motor 73 to rotate the drive wheels 70, 71 in a reverse direction, that is, inwardly, so as to move the transport carriage 49 in a rearward direction toward the empty storage bay 48. Once the carriage 49 reaches its home position 99, the motor 73 is disengaged so that the drive wheels 70, 71 stop rotating. When this occurs, the bracket actuator 72 moves upward to its original, raised position, simultaneously causing the swivel bracket 65 to pivot upwardly into its initial position. At such time, the latch apparatus 59 resumes its indexed orientation adjacent the guide rail 57.

The storage elevator 47 is then raised or lowered to unload the next empty medication carrier 26. Each storage bay 48 is vacated in similar fashion until all the depleted carriers 26 have been removed from the delivery module 33. It should be understood that unloading of the medication carriers 26 occurs in rapid succession, with the storage elevator 47 being correctly positioned for removal of a depleted carrier 26 from a corresponding storage bay 48 virtually simultaneously with the ejection of a carrier 26 through the insertion/retrieval slot 45. With the operator in position to receive each ejected carrier 26, the entire process can take as little as three minutes.

Once all the empty medication carriers 26 have been removed from the delivery module 33, the control center 101 servers transmit a load signal to the controller of the empty module 33. The operator is then notified, through audio, visual or other means, that the module 33 is ready for refilling. At such time, the operator simply depresses the load key 43 located on the front panel 41 of the housing, and thereafter, opens the loading door 44 in order to insert a new medication carrier 26 into the insertion/retrieval slot 45.

The present invention is a fully integrated, real-time, non-sequential, medication management and compliance system that ensures accurate delivery of both custom packaged and commercially available sealed unit dose and unit-of-issue therapeutic products to patients. Importantly, the invention fosters patient compliance with a prescribed treatment regimen by, for example, protecting the patient from adverse drug reactions and ensuring that the patient remains within recommended therapeutic levels.

Furthermore, because the delivery of medication occurs on a unit dosage basis, the patient avoids purchasing an unnecessary number of doses and only purchases the number of units required for the prescribed regimen. This is a tremendous advantage over existing systems, in which prescriptions are normally filled in standard thirty day or sixty day allotments. The present invention reduces the incidence of medication waste by supplying only necessary doses to the patient rather than an aggregate number of doses, which are ultimately discarded. A further advantage to the patient is that each unit dose package remains completely sealed until the point of administration to avoid the medication contamination and degradation problems which plague remote medication delivery systems known in the art.

In the event of a change in the health condition of the patient or other situation requiring a dosage adjustment, other medications and doses having higher or lower strengths are immediately available to the patient, eliminating the need to travel to a physician's office and/or to a pharmacy to obtain the requisite medication. This feature is particularly important with respect to mobility impaired patients. In addition, patient expenses are reduced since the new dosage is already on hand and need not be purchased.

Healthcare practitioners such as physicians and pharmacists also benefit from the present invention. The system enables a provider to treat a greater number of patients with better control of high risk patients, including patients with cognitive, visual, and/or auditory impairments who require more frequent monitoring. The invention allows the healthcare practitioner to rectify a patient's failure to take a scheduled dosage in minutes. In addition, the invention reduces the number of unreimbursable medical services, which include, for example, telephone calls to and from the patient. Also, the invention eliminates the need to write a new prescription every time a dosage needs to be adjusted. The healthcare practitioner makes proper dose adjustments in a prompt and timely fashion, all duly recorded, without any disruption to the patient's course of treatment. This is a significant advantage over existing systems, which allow a remotely based healthcare practitioner to communicate a change in medication or dosage amount to a patient but do not enable the practitioner to remotely change a prescribed dosage in real time.

As previously mentioned, with existing dispensing systems, there is no accurate way to inventory pharmaceuticals and/or to audit patient compliance or consumption of the products. This is due, in part, to the fact that the pharmaceuticals are dispensed in a lot, whereby not every pill or dose is separately identifiable and traceable. In the present invention, medication delivery is accomplished on a unit dosage basis wherein each dose is inventoried with its own electronically coded identifier, allowing a healthcare practitioner to accurately monitor patient compliance with a prescribed treatment regimen. The system enables the healthcare practitioner to remotely manage and deliver individual unit dose packages of prescription and non-prescription medications, medical supplies, diagnostic materials, pharmaceuticals and nutraceuticals to a patient, non-consecutively, without being limited by a sequential delivery restriction. Such unit doses may include, for example, solid orally consumed doses, liquid orally consumed doses, and injection devices containing doses that are administered directly into the body, wherein the doses may comprise a single compound or several compounds.

Managed care providers and other third party payors realize significant advantages from the integrated, non-sequential, remote medication management and compliance system described herein. The invention provides a platform for the control and electronic billing of healthcare products distributed to one or more remote locations on consignment. In this regard, consignment medications may be immediately billed upon dispensing, significantly reducing inventory costs associated with medications that are billed and reimbursed at the time of consumption and providing pharmaceutical companies with a competitive advantage.

Notably, the invention reduces the incidence of medication waste by eliminating the need for a patient to discard remaining doses or obtain a new prescription in the event of a dosage adjustment. This increases the likelihood that a patient will receive a required treatment, reducing the incidence of emergency room visits and hospital admissions occasioned by non-adherence to a prescribed drug regimen. In addition, visits to healthcare providers such as physicians and pharmacists are reduced, significantly decreasing provider related costs.

While the invention has been particularly shown and described with reference to preferred embodiments thereof, it will be understood by those skilled in the art that various alterations in form and detail may be made therein without departing from the spirit and scope of the invention. In particular, while the invention illustrated by the Figures shows a specific size and shape of the delivery module, these parameters can vary considerably and are not limited by the preferred embodiments described herein and depicted in the Figures.

Additionally, while this application generally addresses use of the secure data communication process to deploy communications to and from a delivery module based in a patient's home while protecting patient privacy, the use of such process is by no means limited to this application. The data communication process described herein can be adapted for use in a variety of applications where secure data transmission is desirable (e.g. in conjunction with a patient monitoring system).

What is claimed is:

1. An apparatus for storing and delivering individual doses of therapeutic products, comprising:
   a controller;
   a housing for storing at least one medication carrier, each of the at least one medication carrier comprising a plurality of sealed unit dose packages that each comprise an individual dose of a therapeutic product, each of the at least one medication carrier also comprising an identifier on a surface thereof enabling ones of the plurality of sealed unit dose packages to be remotely and non-consecutively accessed within each of the at least one medication carrier prior to removal from the housing;
   a detectable signal generator, in communication with the controller, operative to provide a detectable signal to prompt a user to request a therapeutic dose; and
   a delivery assembly, in communication with the controller, for removing a sealed unit dose package from a known location in the housing out of the housing for retrieval by the user,
   wherein the controller instructs the detectable signal generator to provide the detectable signal and wherein the controller, in response to input from the user responding to the detectable signal, provides a delivery signal causing the delivery assembly to remove the sealed unit dose package.

2. The apparatus of claim 1, further comprising:
   an electronic reader for reading the identifier and verifying delivery of the sealed unit dose package to the user.

3. The apparatus of claim 1, wherein the controller is in communication with a communications network and outputs a time-stamped notification signal to the communications network, indicative of user compliance or non-compliance.

4. The apparatus of claim 1, further comprising:
   a device for modulating the internal temperature of the apparatus.

5. The apparatus of claim 1, wherein said therapeutic product comprises a medication, pharmaceutical, nutraceutical, diagnostic material, solid dose, liquid dose or injection device comprising doses.

6. The apparatus of claim 1, wherein said identifier comprises one or more of a bar code and a radio frequency identification tag.

7. The apparatus of claim 1, wherein the identifier comprises information regarding the therapeutic product within the unit dose package.

8. The apparatus of claim 7, wherein the information regarding the therapeutic product includes a serial number, manufacturer's lot number, expiration date or a combination thereof.

9. The apparatus of claim 1, wherein said housing includes one or more bays that each comprise a slider for moving the sealed unit dose package in a medication carrier of the at least one medication carrier into the vicinity of an ejector for removal of said package out of the housing.

10. The apparatus of claim 1, further comprising:
    an alert mechanism, in communication with the controller, operative to provide an indication of delivery of the sealed unit dose package to the user.

11. A method for storing and delivering individual doses of therapeutic products in an apparatus comprising a controller and a housing for storing at least one medication carrier, each of the at least one medication carrier comprising a plurality of sealed unit dose packages that each comprise an individual dose of a therapeutic product, the method comprising:
    providing, by a detectable signal generator in communication with the controller and in response to an instruction received from the controller, a detectable signal to prompt a user to request a therapeutic dose;
    receiving, by the controller, an input from a user in response to the detectable signal;
    providing, by the controller to a delivery assembly in response to the input, a delivery signal; and
    removing, by the delivery assembly in response to the delivery signal, a sealed unit dose package from a known location in the housing out of the housing for retrieval by the user,
    wherein each of the at least one medication carrier comprises an identifier on a surface thereof enabling ones of the plurality of sealed unit dose packages to be remotely and non-consecutively accessed within each of the at least one medication carrier prior to removal from the housing.

12. The method of claim 11, further comprising:
    reading, by an electronic reader in communication with the controller, the identifier and verifying delivery of the sealed unit dose package to the user.

13. The method of claim 12, wherein reading the identifier further comprises reading one or more of a bar code and a radio frequency identification tag.

14. The method of claim 11, further comprising:
    providing, by the controller via a communication network, a time-stamped notification signal indicative of user compliance or non-compliance.

15. The method of clam 11, wherein said therapeutic product comprises a medication, pharmaceutical, nutraceutical, diagnostic material, solid dose, liquid dose or injection device comprising doses.

16. The method of claim 11, wherein the identifier comprises information regarding the therapeutic product within the unit dose package.

17. The method of claim 16, wherein the information regarding the therapeutic product includes a serial number, manufacturer's lot number, expiration date or a combination thereof.

18. The method of claim 11, wherein said housing includes one or more bays that each comprise a slider and wherein removing the sealed unit dose package further comprises moving, via the slider, the sealed unit dose package in a medication carrier of the at least one medication carrier into the vicinity of an ejector for removal of said package out of the housing.

19. The method of claim 11, further comprising:
providing, by an alert mechanism in communication with the controller, an indication of delivery of the sealed unit dose package to the user.

* * * * *